US009662265B2

(12) United States Patent
Ooi et al.

(10) Patent No.: US 9,662,265 B2
(45) Date of Patent: May 30, 2017

(54) SYSTEMS AND METHODS FOR IMPROVING SENSORY EYE DOMINANCE, BINOCULAR IMBALANCE, AND/OR STEREOPSIS IN A SUBJECT

(71) Applicants: University of Louisville, Louisville, KY (US); Salus University, Elkins Park, PA (US)

(72) Inventors: Teng Leng Ooi, Upper Arlington, OH (US); Zijiang He, Louisville, KY (US)

(73) Assignees: University of Louisville, Louisville, KY (US); Salus University, Elkins Park, PA (US)

( * ) Notice: Subject to any disclaimer, the term of this patent is extended or adjusted under 35 U.S.C. 154(b) by 0 days.

(21) Appl. No.: 14/895,766

(22) PCT Filed: Jun. 3, 2014

(86) PCT No.: PCT/US2014/040725
§ 371 (c)(1),
(2) Date: Dec. 3, 2015

(87) PCT Pub. No.: WO2014/197489
PCT Pub. Date: Dec. 11, 2014

(65) Prior Publication Data
US 2016/0128893 A1    May 12, 2016

Related U.S. Application Data

(60) Provisional application No. 61/830,411, filed on Jun. 3, 2013.

(51) Int. Cl.
*A61B 3/02* (2006.01)
*A61H 5/00* (2006.01)
(Continued)

(52) U.S. Cl.
CPC ............. *A61H 5/005* (2013.01); *A61B 3/032* (2013.01); *A61B 3/08* (2013.01)

(58) Field of Classification Search
CPC ......... A61B 3/005; A61B 3/022; A61B 3/024; A61B 3/032; A61B 3/08; A61H 5/005;
(Continued)

(56) References Cited

U.S. PATENT DOCUMENTS

| 7,946,707 | B1 * | 5/2011 | McDonald, II | A61B 3/032 351/203 |
| 2012/0179076 | A1 * | 7/2012 | Bavelier | A61H 5/005 601/37 |
| 2013/0100402 | A1 * | 4/2013 | Ooi | A61B 3/10 351/203 |

OTHER PUBLICATIONS

Xu et al., "A binocular perimetry study of the causes and implications of sensory eye dominance", Vision Research, Dec. 2011, vol. 51, No. 23-24, 2386-2397.
(Continued)

*Primary Examiner* — Mohammed Hasan
*Assistant Examiner* — Rahman Abdur
(74) *Attorney, Agent, or Firm* — Fox Rothschild LLP

(57) ABSTRACT

The present invention relates to systems and methods for providing a Push-Pull perceptual learning technique to a subject demonstrating sensory eye dominance (SED), amblyopia, poor stereopsis, and the like. More specifically, the weak eye of the subject is forced to become dominant, while visualization in the strong eye is suppressed over the course of a treatment regimen. Such systems and methods are shown herein to result in a perceptual learning and a reduction of interocular imbalance or SED, as well as an improvement in the visual characteristics typically associated with amblyopia, poor stereopsis and similar visual deficiencies.

40 Claims, 44 Drawing Sheets

(51) Int. Cl.
*A61B 3/032* (2006.01)
*A61B 3/08* (2006.01)

(58) Field of Classification Search
CPC .............. A61H 5/05; A61H 2201/5043; A63F 2300/301
USPC ................ 351/201, 203, 209, 246, 239, 243
See application file for complete search history.

(56) References Cited

OTHER PUBLICATIONS

Xu et al., "Effectively reducing sensory eye dominance with a push-pull perceptual learning protocol", Current Biology Oct. 26, 2010: 20(20): 1864-1868.

\* cited by examiner

FIGURE 1A  Strong Eye          Weak Eye
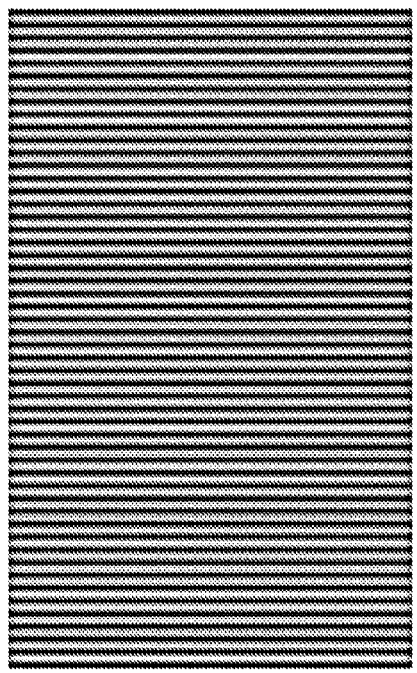 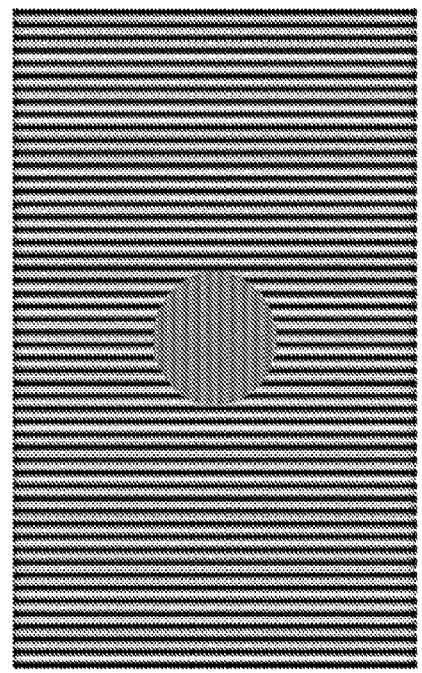
FIGURE 1B  Strong Eye          Weak Eye
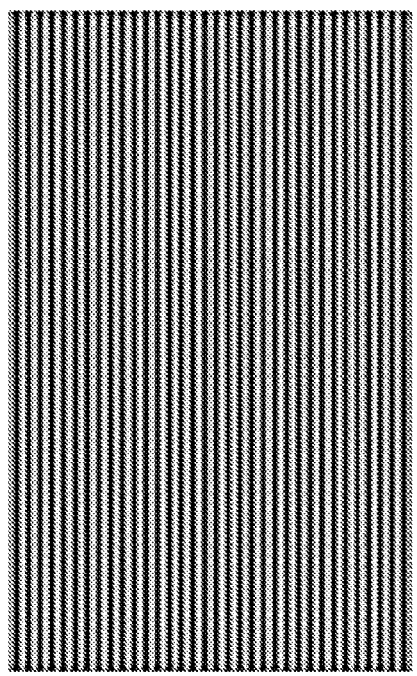 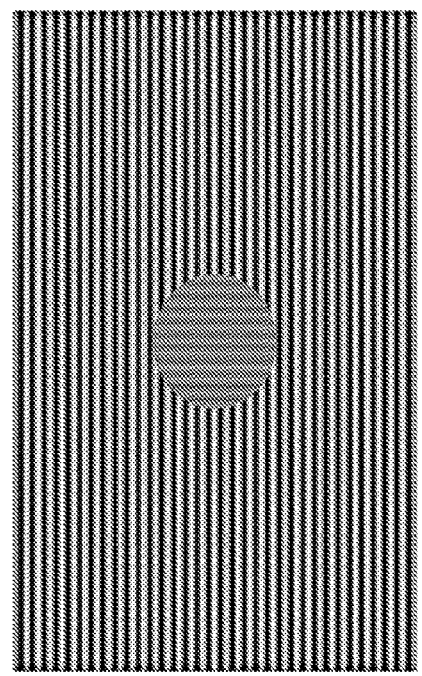

Note:
Same contrast in cat and mice
Cat has reinforcement boundary contour

Note:
Reinforcement boundary contours
of different thickness in cat and mice

| 2-Sample t-Test (MBC in WE) | | | |
|---|---|---|---|
| | t | df | p |
| H | -2.88 | 6 | 0.028 |
| V | -3.936 | 6 | 0.008 |

| 2-Sample t-Test (MBC in WE) | | | |
|---|---|---|---|
| | t | df | p |
| H | -2.658 | 6 | 0.038 |
| V | -2.012 | 6 | 0.091 |

| 2-Sample t-Test (MBC in WE) | | | |
|---|---|---|---|
| | t | df | p |
| H | -0.823 | 6 | 0.442 |
| V | -4.509 | 6 | 0.004 |

| 2-Sample t-Test (MBC in WE) | | | |
|---|---|---|---|
| | t | df | p |
| H | 2.919 | 6 | 0.027 |
| V | 3.669 | 6 | 0.01 |

FIGURE 4A    LE tested
LE (weak eye)     RE (strong eye)
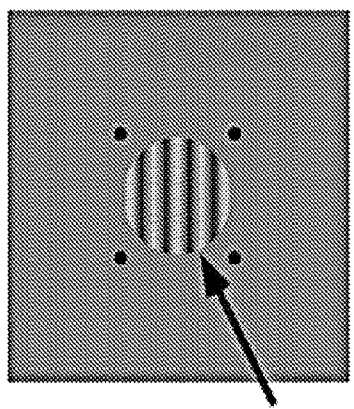 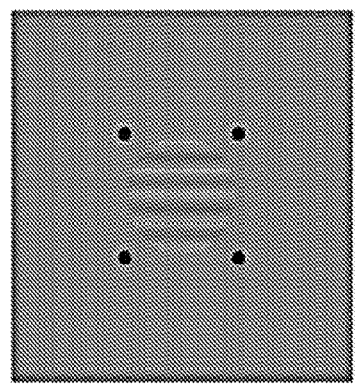
LE balance contrast
FIGURE 4B    RE tested
LE (weak eye)     RE (strong eye)
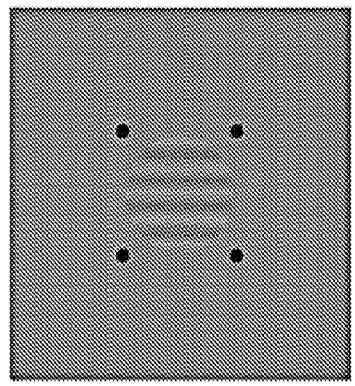 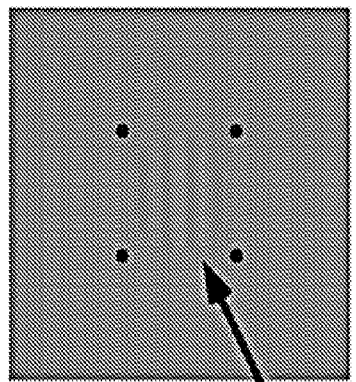
RE balance contrast
Relative SED = difference between RE balance contrast and LE balance contrast Note:

Reinforcement boundary contours in weak eye

A phase-shifted region in the strong eye corresponds to the cat in weak eye; during the training only the weak eye's cat is perceived

Average of fovea and parafoveal locations

All locations ANOVA w/Repeated Measures:

|  | Pre | Post | Retention |
|---|---|---|---|
| Fovea | 0.27 | 0.02 | 0.05 |
| [2, 0] | 0.34 | 0.19 | 0.11 |
| [2, 90] | 0.08 | 0.00 | 0.05 |
| [2, 180] | 0.41 | 0.32 | 0.28 |
| [2, 270] | 0.32 | 0.26 | 0.19 |

$F(2, 8) = 11.943$, $p = 0.004$
Contrasts:
Pre vs. Post: $F(1, 4) = 13.386$, $p = 0.022$
Pre vs. Retention: $F(1, 4) = 16.544$, $p = 0.015$
Post vs. Retention: $F(1, 4) = 0.697$, $p = 0.451$ Stereo reaction times at fovea and parafoveal locations
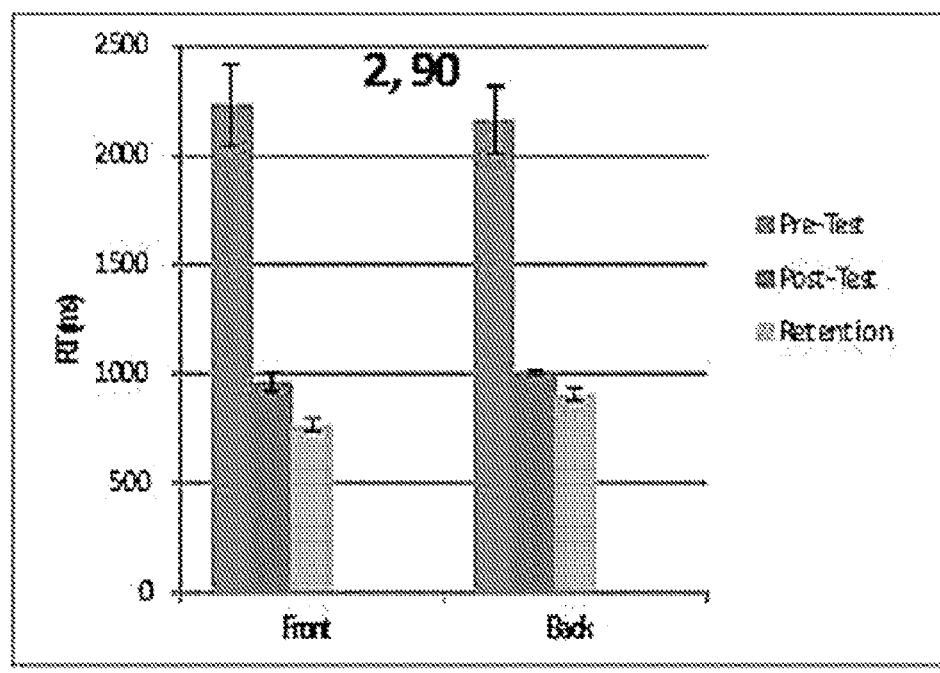
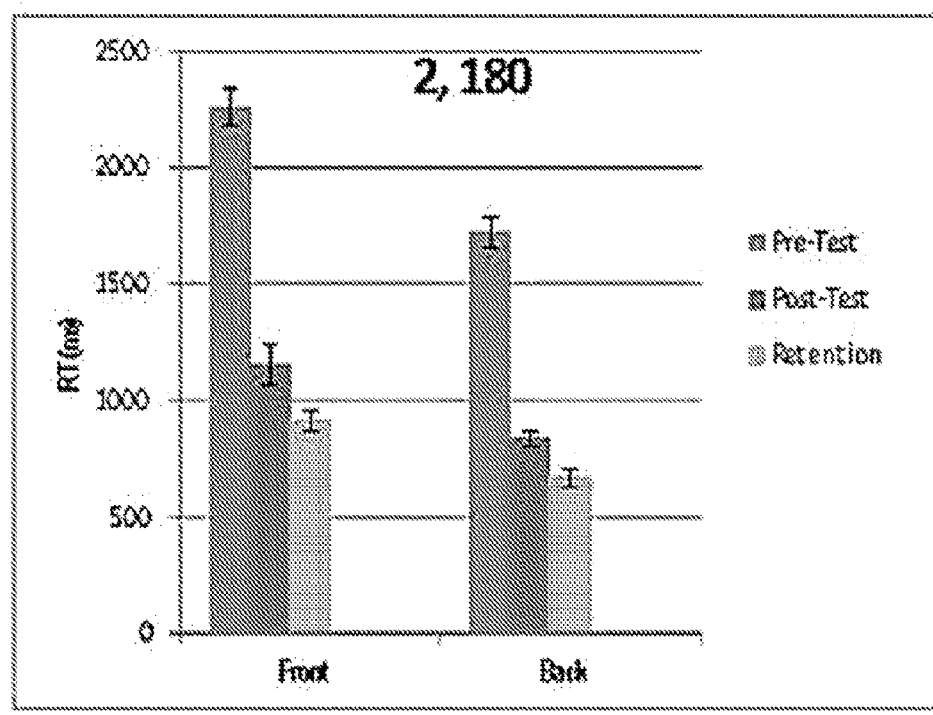
FIGURE 18

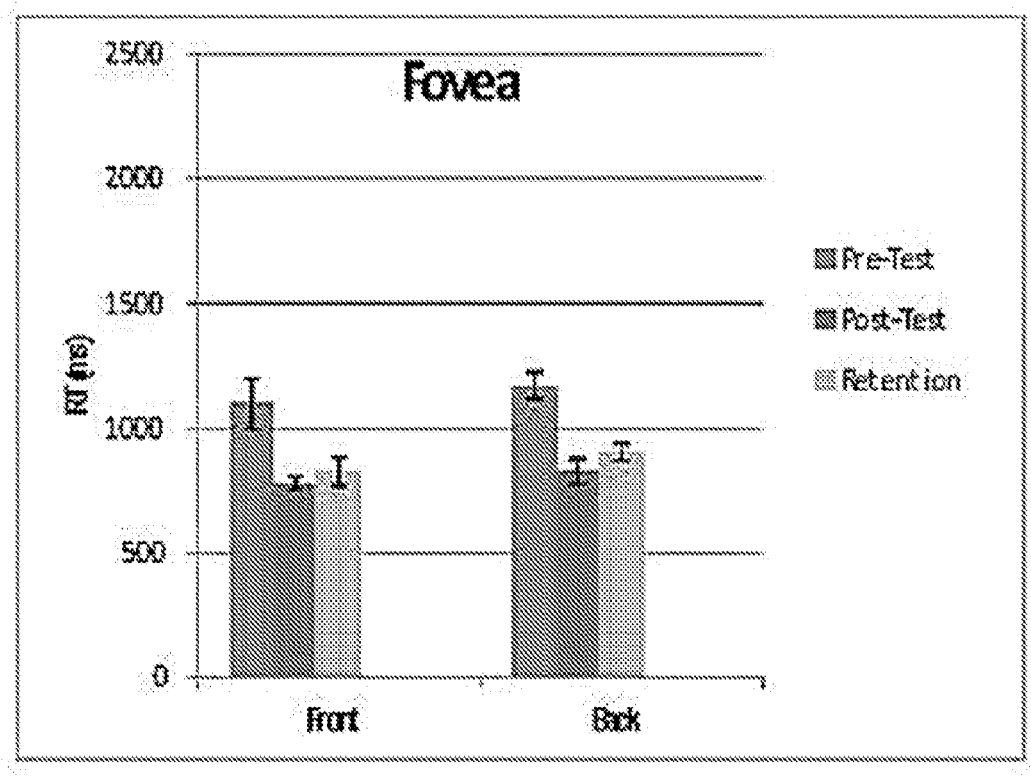
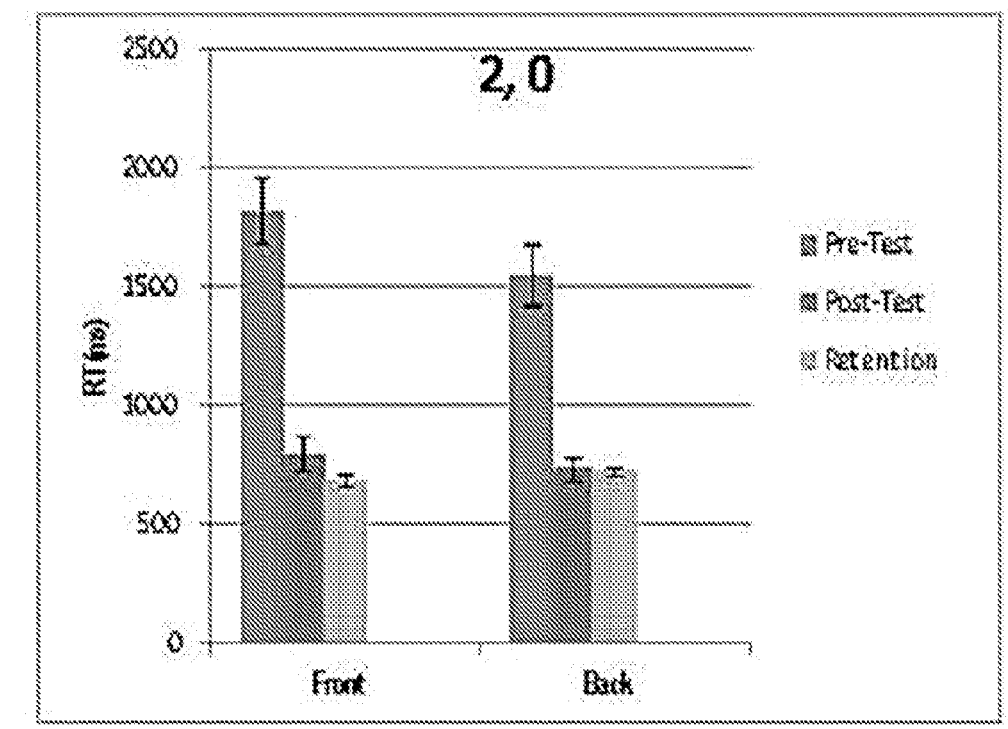
FIGURE 18 Cont'd

| Location | Stats (2-Sample t-tests) | | Front Post-Test | Front Retention | Back Post-Test | Back Retention |
|---|---|---|---|---|---|---|
| Fovea | Pre-Test | t | 3.064 | 2.370 | 4.755 | 4.190 |
| | | df | 6 | 6 | 6 | 6 |
| | | p | 0.022 | 0.055 | 0.003 | 0.006 |
| | Post-Test | t | | -0.714 | | -1.338 |
| | | df | | 6 | | 6 |
| | | p | | 0.502 | | 0.229 |
| 2, 0 | Pre-Test | t | 6.525 | 8.02 | 6.000 | 6.428 |
| | | df | 6 | 6 | 6 | 6 |
| | | p | 0.001 | <0.001 | 0.001 | 0.001 |
| | Post-Test | t | | 1.513 | | 0.207 |
| | | df | | 6 | | 6 |
| | | p | | 0.181 | | 0.843 |
| 2, 90 | Pre-Test | t | 6.639 | 7.799 | 7.424 | 7.975 |
| | | df | 6 | 6 | 6 | 6 |
| | | p | 0.001 | <0.001 | <0.001 | <0.001 |
| | Post-Test | t | | 3.717 | | 3.231 |
| | | df | | 6 | | 6 |
| | | p | | 0.01 | | 0.018 |
| 2, 180 | Pre-Test | t | 9.285 | 14.729 | 12.312 | 13.841 |
| | | df | 6 | 6 | 6 | 6 |
| | | p | <0.001 | <0.001 | <0.001 | <0.001 |
| | Post-Test | t | | 2.483 | | 3.428 |
| | | df | | 6 | | 6 |
| | | p | | 0.048 | | 0.014 |
| 2, 270 | Pre-Test | t | 12.147 | 11.941 | 10.527 | 9.835 |
| | | df | 6 | 6 | 6 | 6 |
| | | p | <0.001 | <0.001 | <0.001 | <0.001 |
| | Post-Test | t | | 0.012 | | -1.749 |
| | | df | | 6 | | 6 |
| | | p | | 0.991 | | 0.131 |

FIGURE 18 Cont'd

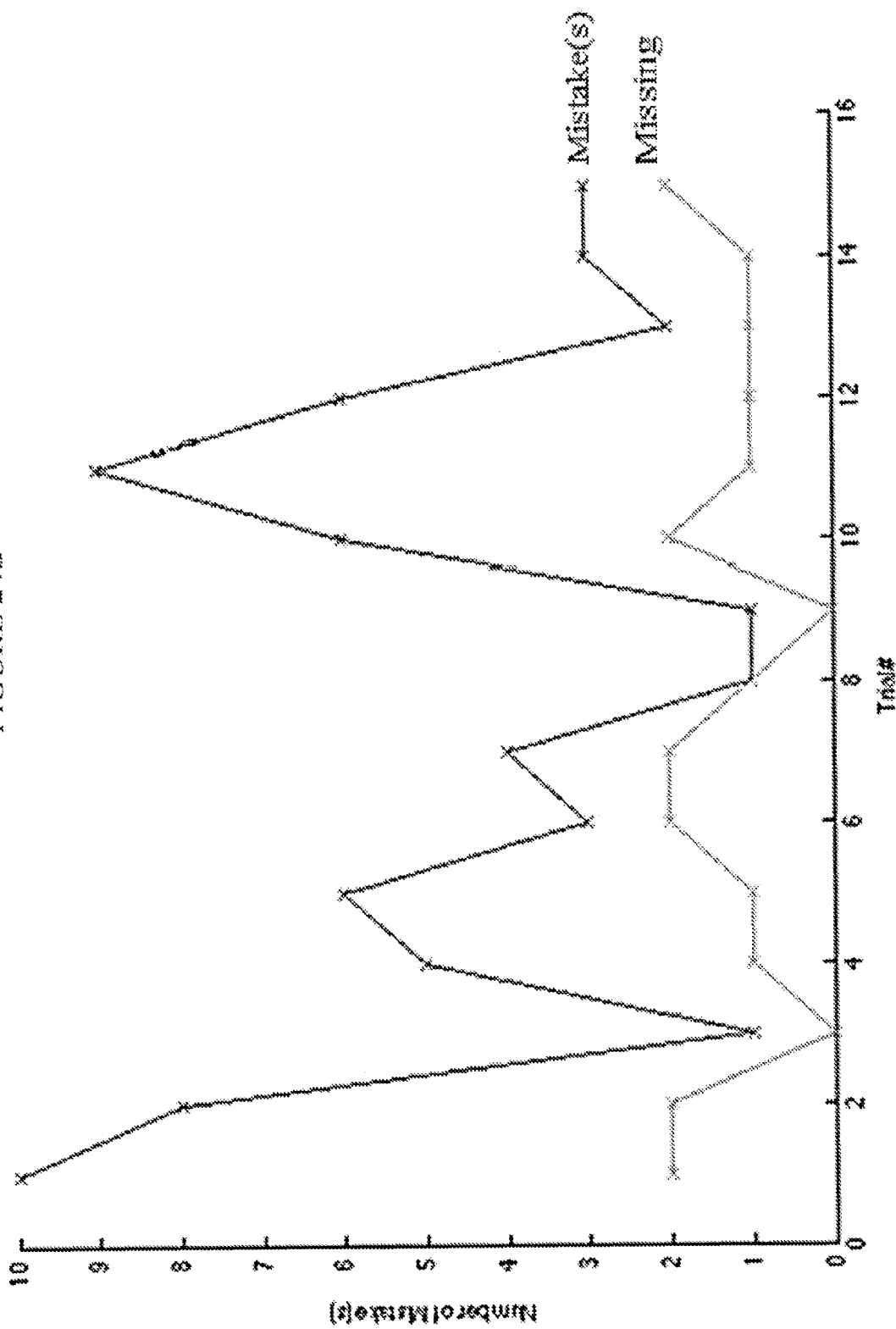

FIGURE 27
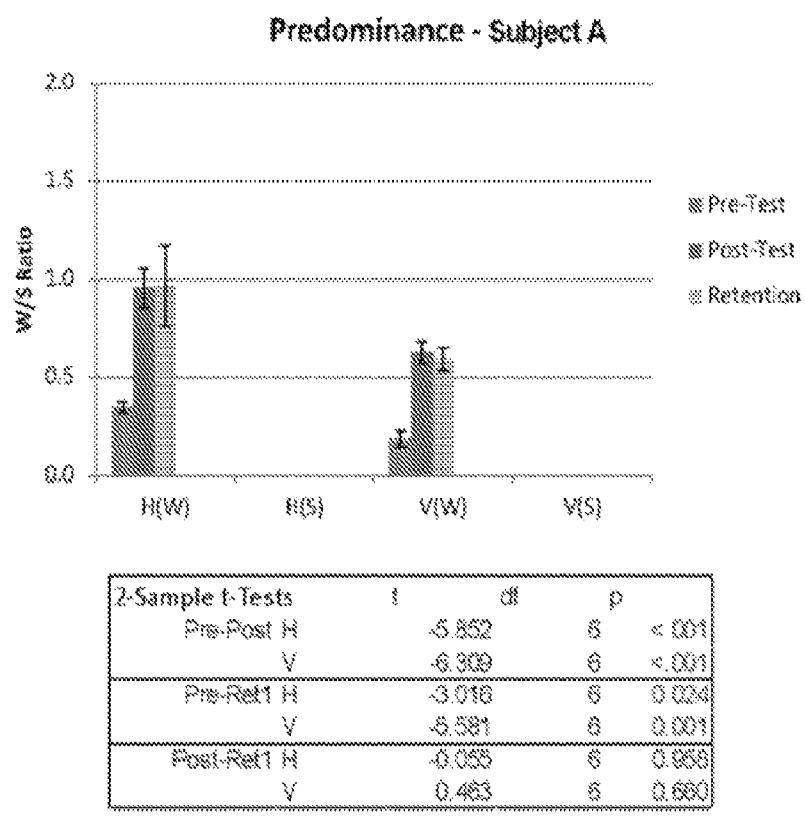
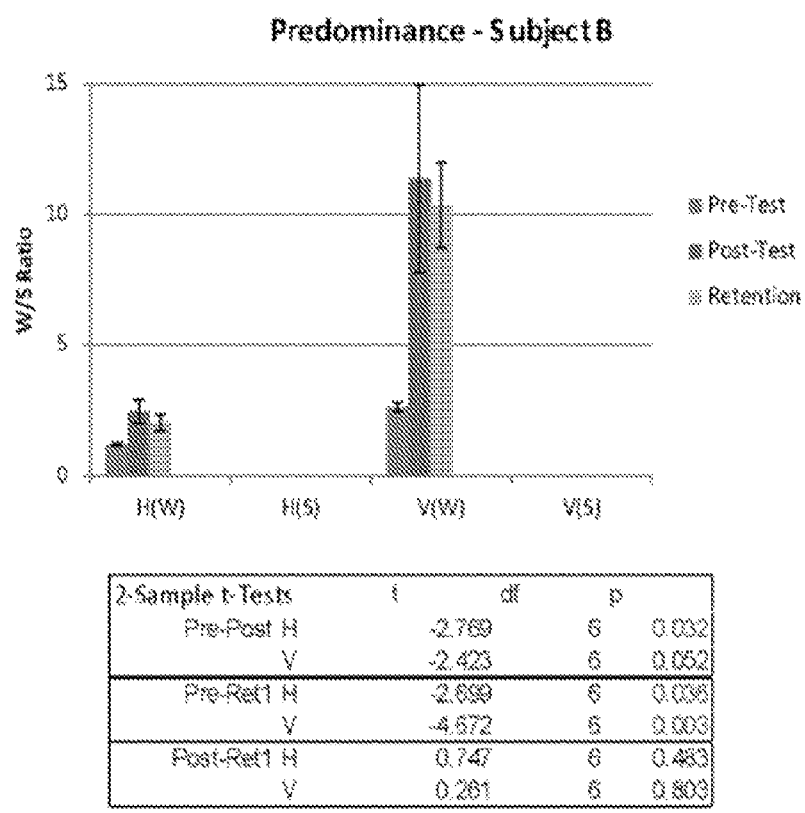

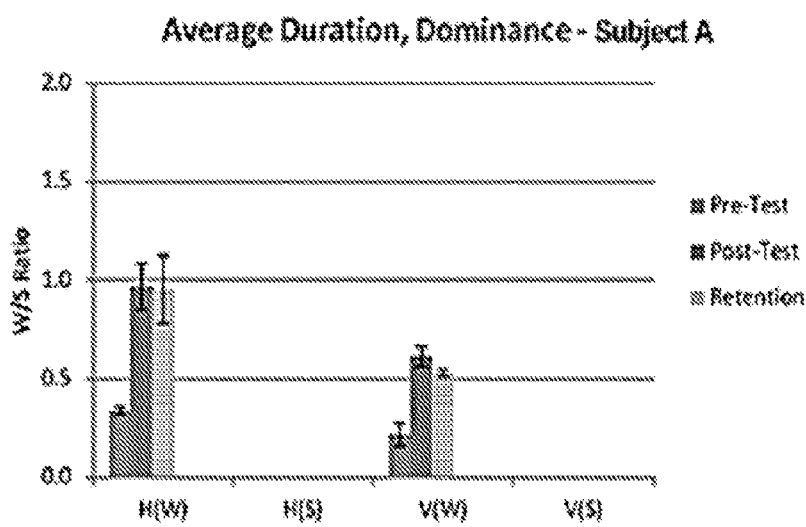
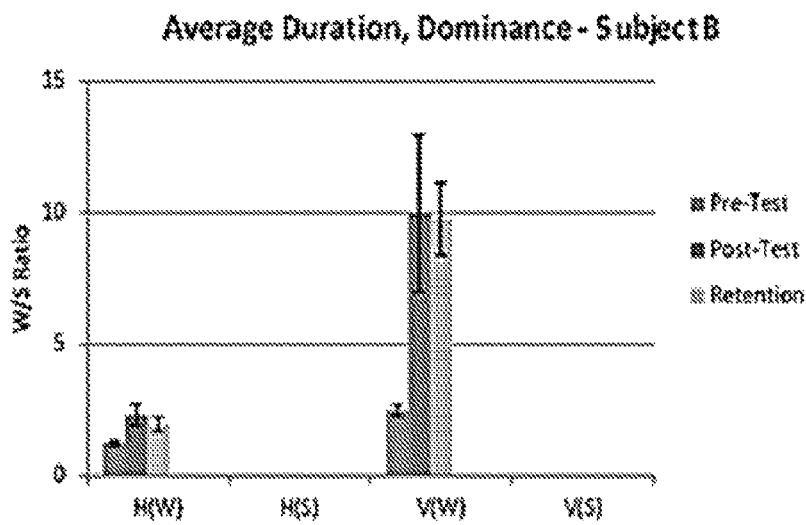
FIGURE 28

SYSTEMS AND METHODS FOR IMPROVING SENSORY EYE DOMINANCE, BINOCULAR IMBALANCE, AND/OR STEREOPSIS IN A SUBJECT

CROSS REFERENCES TO RELATED APPLICATIONS

This application is a U.S. national phase application of PCT International Application No. PCT/US2014/040725 filed Jun. 3, 2014, which claims priority to U.S. Provisional Patent Application No. 61/830,411, filed Jun. 3, 2013, the contents of each of which are incorporated herein by reference in their entirety.

FIELD OF THE INVENTION

The present invention relates to systems and methods for reducing or otherwise improving binocular imbalance, sensory eye dominance, amblyopia, and/or stereopsis threshold and/or response time in a subject by stimulating the subject's weak or non-dominant eye and inhibiting the strong or dominant eye.

BACKGROUND OF THE INVENTION

Binocular vision contributes to the visual ability of figure-ground segmentation and fine depth discrimination. Retinal images of 3-D visual scenes from the two eyes usually have the same mean contrast energy over time. This suggests that the binocular visual system is built to treat the inputs from the two eyes equally in order to achieve a high proficiency. Indeed, for a standard observer, stimuli with equal contrast in each eye induces superior binocular perception, as compared to stimuli with unequal contrast levels.

The interocular integration and inhibitory mechanisms that are part of the binocular neural network support a variety of binocular visual functions including summation, fusion, stereopsis and suppression. Both mechanisms work together, with the interocular inhibitory mechanism suppressing dissimilar images from one or both eyes, to achieve a coherent 3-D representation of the visual scene. Binocular visual processing is adversely affected, however, when an observer's eyes are not equally strong, i.e. one eye is dominant over the other and provides a larger weighted contribution to the binocular neural network. Indeed, human observers with a significant degree of unbalanced interocular inhibition, often called sensory eye dominance (SED), tend to have degraded binocular visual processing and reduced binocular depth perception.

The magnitude of SED varies in the population along a continuum. At one end, observers with minor SED have clinically normal stereoacuity. At the other end, however, observers with strong SED have little or no stereopsis. Examples of the latter include amblyopia and strabismus, which are also characterizable by a host of visual deficits related to contour integration, spatial and temporal vision, as well as those related to higher level visual functions.

There is a continuing need for establishing treatment methods and regimens that can correct SED, amblyopia, strabismus, and/or otherwise improve a patient's stereopsis and/or binocular imbalance. In particular, there is a need for a system, method, or protocol, that can reduce and/or correct binocular imbalance in a subject, improve the visual impairments associated with the dominance of one eye of a subject over the other, and/or otherwise improve a subject's ability to resolve the three-dimensional structure and/or depth perception relative to a given object. The present invention addresses at least these needs.

SUMMARY OF THE INVENTION

The present invention relates, in part, to systems and methods for providing a Push-Pull perceptual learning technique to a subject demonstrating SED, amblyopia, strabismus, and/or poor stereopsis. More specifically, perception is stimulated in the subject's weak or non-dominant eye, which is then taken through a series of tasks that require interactive feedback and/or manipulation of the images by the subject. In the meantime, the strong or dominant eye is perceptually suppressed. Such systems and methods are surprisingly and unexpectedly shown herein to result in a perceptual learning, a reduction of interocular imbalance, and/or an improvement in stereopsis.

In certain non-limiting embodiments, the present invention includes a computer implemented method for reducing sensory eye dominance, amblyopia, and/or poor stereopsis in a subject comprising: (a) communicating to a subject via a processor and imaging system a series of visual stimuli where a plurality of first visual stimuli are presented to a non-dominant eye of a subject and at least one second visual stimuli is presented to a dominant eye of the subject, wherein visualization of the first visual stimuli by the non-dominant eye is preferred; (b) providing to the subject a set of visual characteristics that match at least one of the plurality of first visual stimuli; (c) instructing the subject to identify, by actuation of a controller, at least one of the first visual stimuli having said set of visual characteristics; and (d) determining, via the processor and after identification by the subject, if the subject correctly identified the first visual stimuli having said set of visual characteristics.

In certain aspects the plurality of first visual stimuli include a plurality of grating discs, which may be presented in one or more of a variety of orientations and with one or more of a variety of features. By way of non-limiting example, the grating discs may be presented against a grating background and are oriented at an angle from greater than about 0 degrees to less than about 180 degrees relative to the background and/or as a phase shift from the grating background by an amount from greater than about 0 degrees to less than about 180 degrees. The grating discs may optionally include a boundary contour line and/or any one or more of the other visual features discussed herein. In certain embodiments, at least two of the grating discs are oriented (e.g. angled and/or phase shifted) the same, and in other embodiments, only two of the grating discs are oriented the same.

In further alternative embodiments, the grating background is vertically oriented and the series of first visual stimuli are phase shifted from the grating background by an amount from greater than about 0 degrees to less than about 180 degrees with an optional contour ring substantially surrounding each stimulus's perimeter. Each of the first visual stimuli may be at unique phase shifts, relative to the grating background. In certain aspects, at least two of the first visual stimuli are at the same phase shift and at least one visual stimulus is at a unique phase shift, relative to the grating background. In further aspects, one portion of each grating disc is provided at a first phase shift and a second portion of each disc is provided at a second phase shift relative to the first portion. A portion of at least one grating disc may be optionally removed so as to give the appearance of a hole in the disc.

In further alternative embodiments, the grating background is horizontally oriented and the series of first visual stimuli are angled from the grating background by an amount from greater than about 0 degrees to less than about 180 degrees with an optional contour ring substantially surrounding each stimulus's perimeter. Each of the first visual stimuli may be at unique angles, relative to the grating background. In certain aspects, at least two of the first visual stimuli are at the same angle and at least one visual stimulus is at a unique angle, relative to the grating background. In further aspects, one portion of each grating disc is provided at a first angle and a second portion of each disc is provided at a second angle relative to the first portion. A portion of at least one grating disc may be optionally removed so as to give the appearance of a hole in the disc.

The second visual stimuli may include a grating background, which may be parallel to the grating background presented to the non-dominant eye with the first visual stimuli. The second visual stimuli may optionally include one or more grating discs, which may be presented against a grating background and are optionally phase shifted from the grating background by an amount from greater than about 0 degrees to less than about 180 degrees.

Using one or more of the foregoing, the user receives instructions from the system to identify one or more of the visual stimuli presented to the non-dominant eye. In certain embodiments, at least two of the grating discs presented within the first visual stimuli are the same and at least one of the grating discs is different, wherein the subject actuates the controller to move one of the same grating discs to contact the other grating discs. In certain embodiments of the foregoing, one of the first discs is a primary grating disc and may be controlled by the user with the controller such that the user identifies the first visual stimulus having said set of visual characteristics by contacting it with the primary disc. At least one additional visual feature may distinguish the primary disc from the remaining discs of the first visual stimuli such that the primary disc may be identified by the subject.

In other embodiments, the subject is presented with a series of grating discs where at least two discs are different. The subject actuates the controller to identify the grating disc having the set of visual characteristics provided to the subject. In further embodiments, the subject is presented with a series of grating discs where at least two discs are different and actuates a first portion of the controller if the grating disc having the set of visual characteristics provided to the subject is present or actuates a second portion of the controller if the grating disc having the set of visual characteristics provided to the subject is not present. In such an embodiment, the reaction time between presentation and actuation also (or alternatively) may be measured.

In even further embodiments, the plurality of first visual stimuli comprises a first series of grating discs are presented to the subject, and then removed. A second series of discs are then presented where the second series comprises more discs than the first series and optionally includes the first series of discs. The subject is then instructed to actuate the controller to identify if the first series of grating discs is present.

In any of the foregoing, the first visual stimuli and the second visual stimuli may be presented as separate images. In certain alternative embodiments, however, the first stimuli and the second stimuli are presented as a single image, wherein a first filter on the non-dominant eye facilitates presentation of the first stimuli to that eye and a second filter on the dominant eye facilitates presentation of the second stimuli to that eye.

The present invention also relates to systems for reducing sensory eye dominance or amblyopia in a subject. In one embodiment, the system may include (a) a visualization element adaptable to present a plurality of first visual stimuli to a non-dominant eye of a subject and at least one second visual stimuli to a dominant eye of a subject; (b) a controller for actuation by the subject in response to the presentation of the first and second visual stimuli; and (c) a non-transient storage medium coupled to the visualization element that controls the presentation of the first visual stimuli and second visual stimuli to the subject such that visualization in the non-dominant eye of the subject is stimulated and visualization in the dominant eye is inhibited, wherein the non-transient storage medium receives a signal from the controller upon actuation by the subject.

Additional embodiments and advantages will be readily apparent to one of skill in the art on the basis of the disclosure provided herein.

BRIEF DESCRIPTION OF THE FIGURES

FIG. 1A provides a binocular rivalry stimulus with a vertical disc surrounded by an orthogonal grating half-image in the weak (or non-dominant) eye and the same orthogonal grating half-image in the strong (or dominant) eye; and FIG. 1B illustrates a variant of the binocular rivalry stimulus where the orientation of the disc grating is horizontal while the surrounding grating is vertical.

FIG. 4 illustrates binocular rivalry stimulus for measuring SED, where in FIG. 4A the weak eye is tested with a variable contrast vertical grating while the strong eye views a fixed contrast horizontal grating. During the experiment, the subject responded to his/her percept, horizontal or vertical, by pressing the appropriate key. If he/she saw a mixture of the two gratings, he/she would respond to the predominant orientation perceived. A QUEST procedure was used to adjust the vertical grating contrast according to the subject's response. That is, the grating contrast was adjusted gradually after each trial until, the point of equality, where the subject obtained an equal chance of seeing the two gratings (equal predominance) was reached. The contrast obtained provides the balance contrast for the eye that viewed the variable contrast vertical grating, in this case, the weak eye. In FIG. 4B the gratings between the two eyes were switched to obtain the balance contrast for the strong eye. The difference between the LE and RE mean balance contrast values is defined as the SED.

FIG. 27 illustrates improved ability of the weak eye to see the grating disc of the binocular rivalry stimulus (increased weak to strong eye predominance ratio) after training for subjects A and B. The improvement is long lasting as evidenced by the retention data.

FIG. 28 illustrates improved ability of the weak eye to maintain the grating disc of the binocular rivalry stimulus in perception after training for subjects A and B. The improvement is long lasting as evidenced by the retention data.

DETAILED DESCRIPTION OF THE INVENTION

Figure 2A:
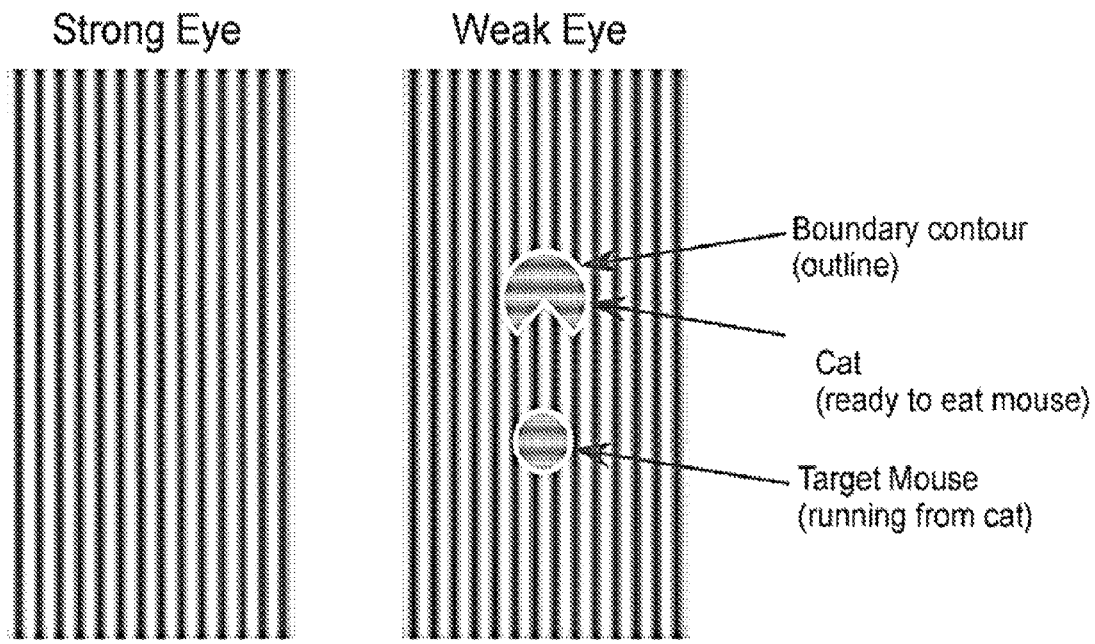
FIGS. 2A-F illustrate multiple embodiments of the "cat and mouse" embodiment of the present invention.

The present invention relates, in part, to systems and methods for providing a Push-Pull perceptual learning technique to a subject demonstrating SED, amblyopia, strabismus, and/or poor stereopsis. More specifically, the weak or non-dominant eye of the subject is forced, through increasing the boundary contour content of its image or through other means of enhancement such as attention cueing, to become dominant, while visualization in the strong or dominant eye is suppressed over the course of treatment. The non-dominant eye is then taken through a series of tasks that require interactive feedback and/or manipulation of the images by the subject, which in certain aspects uses video game concepts (e.g. scoring for reward and penalization, increased user interaction, quick visual and motor responses, and the like). Such systems and methods are surprisingly and unexpectedly shown herein to result in a perceptual learning, a reduction of interocular imbalance, and/or an improvement in stereopsis. In effect, they demonstrate a marked reduction in SED and amblyopia, an improvement in stereopsis, as well as the improvement of visual characteristics typically associated with such disorders.

Generally, the present method includes obtaining the attention of the non-dominant eye and maintaining that attention over the course of treatment. The attention can be obtained using a separate attention cue, or otherwise by the visual stimulus presented during the treatment. In either case, the visual stimuli presented to the non-dominant eye are preferred and perceived over any images simultaneously presented to the dominant eye. Applicants have shown herein that this combination of the stimulation of the non-dominant eye (the push) combined with the suppression of the dominant eye (the pull) is advantageous for improving visual defects associated with SED, amblyopia, poor stereopsis, or the like. Specifically, the pull component of the method stimulates the dominant eye, while denying its retinal image from being perceived. While not intending to be bound by theory, it is believed that this reduces the dominant eye's effectiveness in suppressing the non-dominant eye. Applicants have shown herein, that such a technique results in reduced binocular imbalance, and leads to improved stereopsis, improved binocular and monocular visual processing, and similar visual traits.

Prior to or in conjunction with the start of treatment, the visual attention of the observer must first be drawn to the non-dominant eye. In one embodiment, this may be optionally accomplished by presenting only the non-dominant eye with an attention cue. By way of non-limiting example, the attention cue may be an image presented only to the non-dominant eye or the manipulation of an image only in the non-dominant eye, such as flashing, jitter, contrast change, or the like. It may be provided for any amount of time that is effective to obtain the observer's attention, such as, but not limited to, less than 1 second or, alternatively, at various times during the course of a treatment or trial. Again, the attention cue is not limited to the foregoing and may be easily adapted into any alternative configuration designed to shift the observer's focus to the non-dominant eye. In alternative embodiments, however, the corrective visual stimuli, itself, acts to shift the observer's attention to the non-dominant eye. Thus, in such embodiments, a separate attention cue is unnecessary.

The visual stimuli used to correct interocular imbalance are provided to any of, each, or all of the foveal, parafoveal or peripheral retinal regions of the observer. In certain preferred embodiments, the stimuli are provided in two or more of these regions with the intent of simultaneous training (or retraining) of each portion of the eye. As used herein, the "foveal region" refers to the center of the retina up to about 1 degree from the foveal center. As used herein, the "parafoveal region" refers to the region surrounding the fovea from greater than about 1 degree to about 10 degrees from the foveal center; and the "peripheral region" refers to the retinal region outside of about 10 degrees from the foveal center.

Visual stimuli may include one isolated stimulus at the position of interest, but in certain preferred embodiments it may include a series of multiple presentations simultaneously at various positions in the field of vision, as discussed in greater detail below. The visual stimuli, which may be non-identical patterns, in certain embodiments, may include one or multiple grating discs optionally having a boundary contour line, where one disc is provided to the non-dominant eye and an optional second disc may be provided to the dominant eye. Again, the discs are specifically oriented or provided to the subject in a manner (or with visual characteristics) that maintains the perception of the observer's non-dominant eye, as discussed in greater detail below. In certain non-limiting embodiments, each disc is provided as a series of parallel lines extending from one end of the disc to the other and forming a circle or disc shaped object. The visual stimuli are not necessarily limited to such embodiments, however, and may include any larger, smaller, alternative shapes or alternative image types where perceptual preference is or would be given to the subject's non-dominant eye, as opposed to any image presented to the dominant eye. Such alternative images, in certain preferred embodiments, should be adaptable for use in accordance with the teachings herein.

Visual stimuli may be provided against a solid background, but in certain preferred embodiments, are provided against a grating background, which facilitates the user's perception with the non-dominant eye. With the former, the blank background may be gray or subdued background or any other color (such as a light color) where the visual stimulus may be detectable. With the latter, a grating background having substantially the same orientation is presented to each eye of the observer. In certain embodiments, the grating background is provided as a series of black and/or gray bars aligned in parallel at a distance similar to the grating discs. In further embodiments, the bars are aligned to be substantially vertical or horizontal, though in certain embodiments the bars may be presented at an oblique or diagonal direction.

The following provides a series of embodiments of training protocols that are or may be adapted using video game concepts, i.e. the use of a processor, visualization screen, and a controller or other actuator where the user interacts with the images presented on the screen. In certain aspects, the interaction dictates or may dictate the progression of the protocol. These embodiments are not intended to be limited to the invention and variations thereof are provided or may be otherwise readily apparent. The present invention may include any one or combination of these embodiments during the course of treatment.

A. Matching of Primary and Secondary Stimuli (the Cat and Mouse Embodiment)

In one non-limiting embodiment of the invention, the user matches a primary stimulus with a secondary stimulus that may move throughout the user's field of vision. The background to both a dominant eye (or strong eye) and non-dominant eye (or weak eye) may be provided as a horizontal or vertical grating, though in alternative embodiments the grating may be provided at a diagonal or oblique angle. The visualized stimuli (e.g. grating discs) presented to the non-dominant eye are preferably, though not exclusively, at an oblique or orthogonal orientation relative to the background grating and may be optionally outlined with a boundary contour line. An illustration of such embodiments are provided in FIGS. 2A and 2B. In certain alternative embodiments, however, the grating discs may be phase shifted relative to the background grating.

In certain aspects, the visual stimuli presented to the non-dominant eye are a series of grating discs, which may be randomly spaced throughout the user's field of vision. The orientation of the grating of each disc is largely unique relative to the background grating and to the other discs presented. One of the grating discs is identified as a primary stimulus (or "cat") and the remaining discs are secondary stimuli (or "mice"). The primary stimulus has an orientation that is the same as at least one (in certain embodiments only one) of the secondary stimuli, i.e. it is dissimilar in orientation to the remaining secondary stimuli.

Figure 2B:
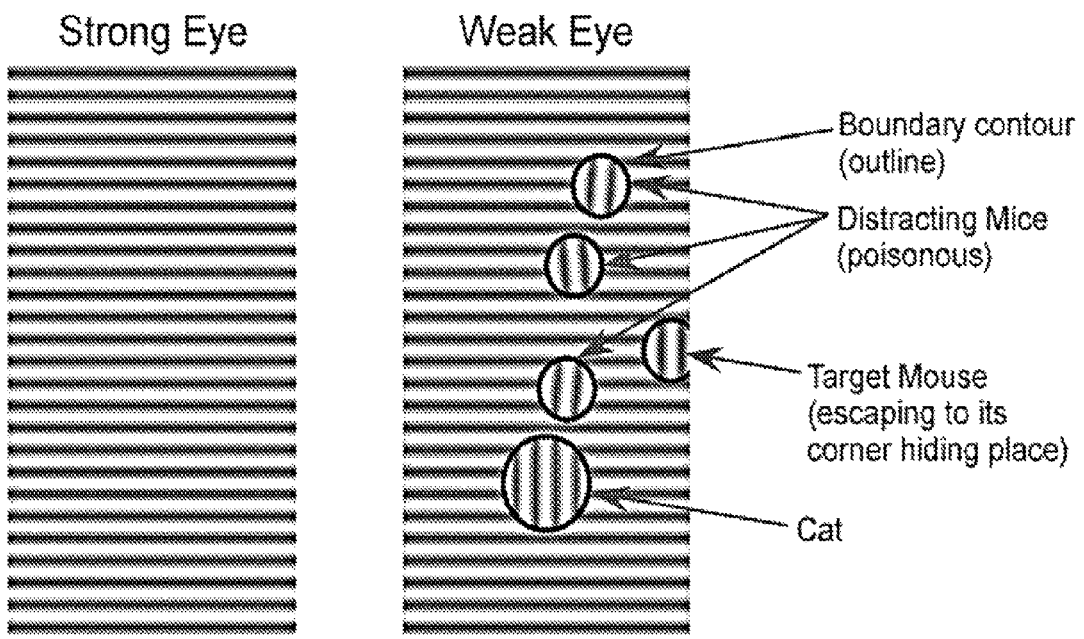
Figure 2C:
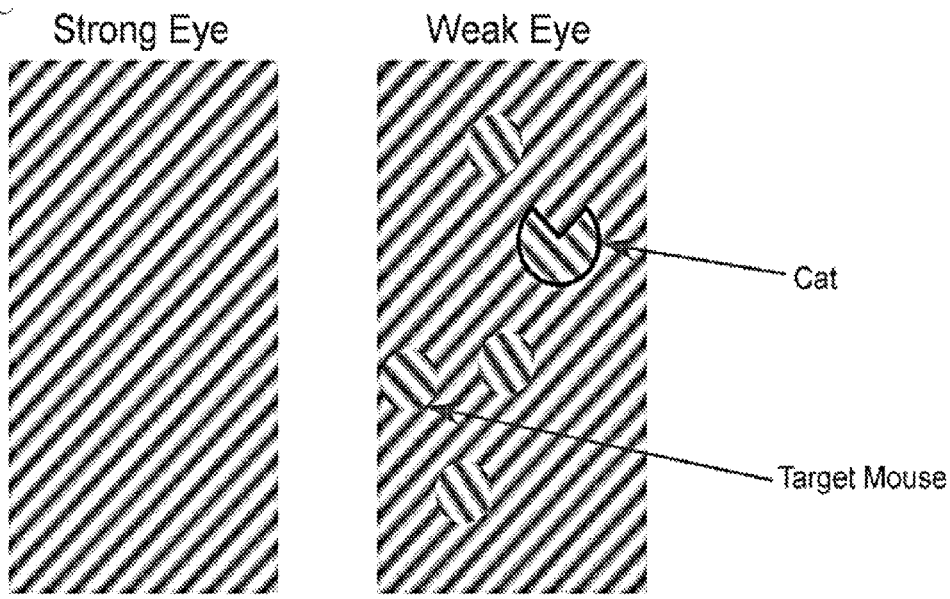
Figure 2D:
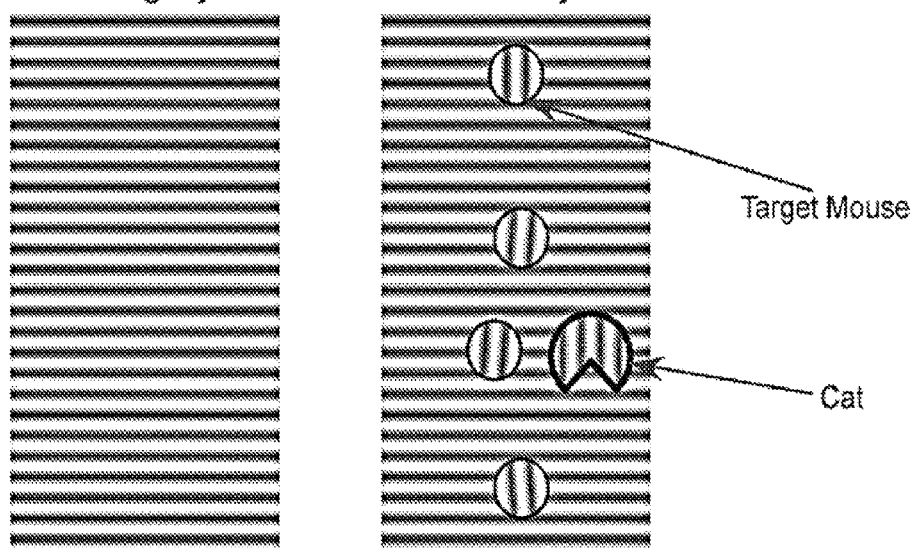
Figure 2E:
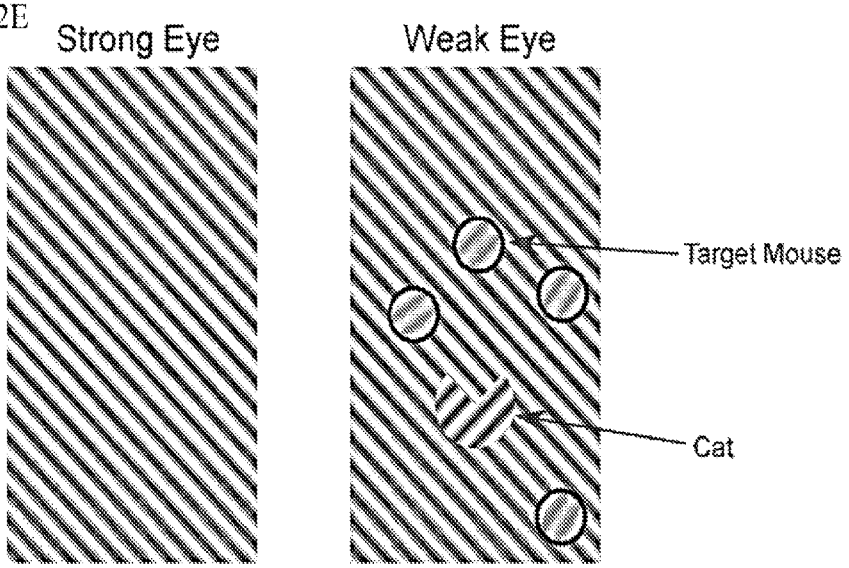
Figure 25:
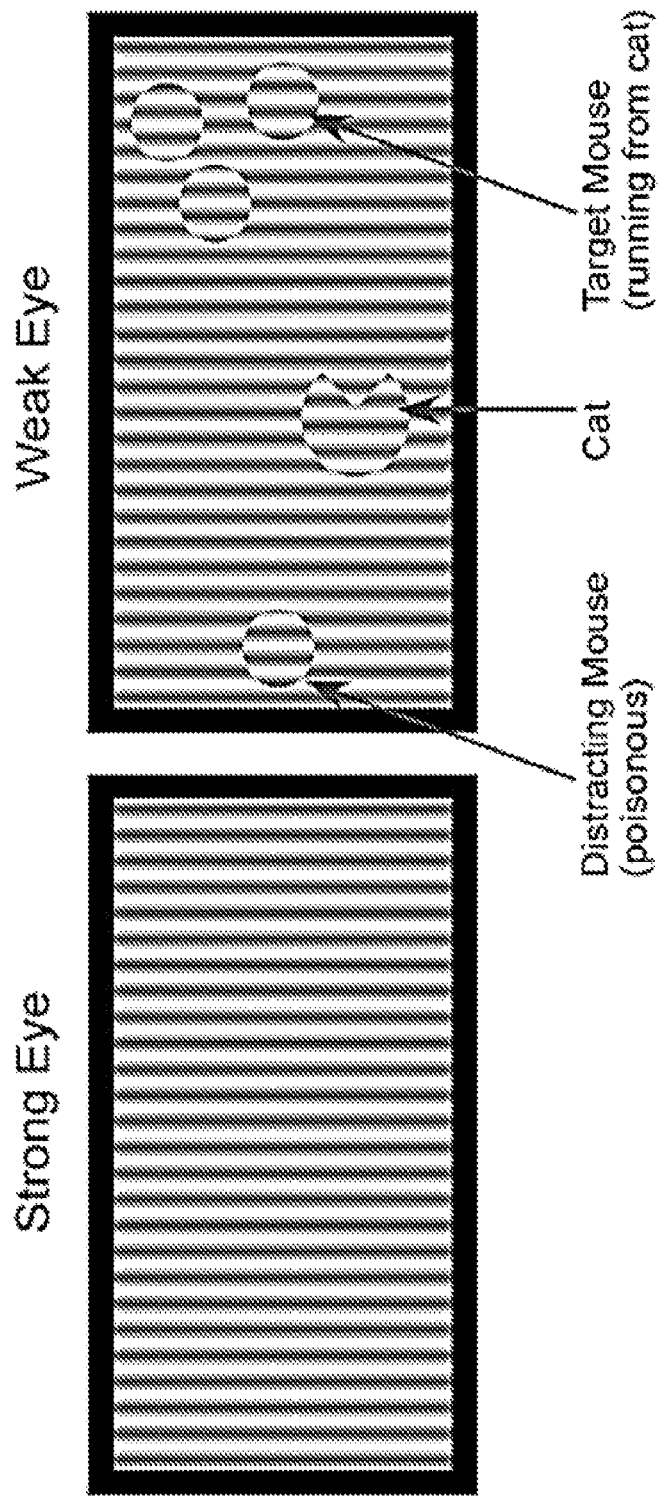
FIG. 25 illustrates an alternative "cat and mouse" embodiment of the present invention. In this embodiment, the cat and target mouse are phase-shifted relative to the vertical grating background so that they are perceived in a certain depth (front or back). The distracting mice are phase-shifted to be in the opposite depth (back or front).

Referring to FIGS. 2A-2F and 25, one or more of the series of features or characteristics may be used to signify the primary stimulus and the secondary stimuli. By way of non-limiting example, such features may include a marking, size variation, a notch, hole, boundary line, jitter, movement or other similar features that are communicated to the subject and suggest the particular uniqueness of that particular stimulus over the remaining stimuli. FIG. 2A provides one embodiment demonstrating a primary visual stimulus (identified as the "cat") that is larger than the secondary visual stimulus (identified as the "mouse") and has a notch or portion removed from it. Both stimuli also have a white boundary contour line to distinguish them from the background. FIG. 2B illustrates a larger primary stimulus without a notch and both the primary and secondary stimuli have black contour lines. FIG. 2C illustrates a black contour line around and notch within the primary stimuli only, secondary stimuli contains no boundary line. FIG. 2D illustrates black contour lines around each stimuli with the primary stimuli having a thicker line. FIG. 2E illustrates a contour boundary line around the secondary stimuli and only a notched primary stimuli (no boundary). FIG. 25 provides the stimuli as being phase shifted with the primary stimulus being larger and having a notch.

One or a combination of the foregoing identification markers may be used to make perception of the images easier or more difficult for the user. One of skill in the art would readily appreciate that the more distinguishing features in the non-dominant eye's stimuli, the greater the ease of identification and the fewer or less noticeable features the more difficult is the identification. Such a manipulation may be used to alter the challenge to the user, making it more or less difficult during treatment.

In certain embodiments, at least one primary stimulus and at least one secondary stimulus is presented to the non-dominant eye. In further embodiments, at least one primary stimulus is present in conjunction with two or more secondary stimuli, again, where at least one secondary stimulus has an orientation matching the primary stimulus. While the number of primary and secondary stimuli is not considered limiting to the invention, in certain embodiments, at least one (and in certain embodiments only one) primary stimulus is presented and from about 2 to about 100 secondary stimuli may be presented; from about 2 to about 50 secondary stimuli may be presented; or from about 2 to about 25 secondary stimuli may be presented during the course of a given trial.

Figure 8:
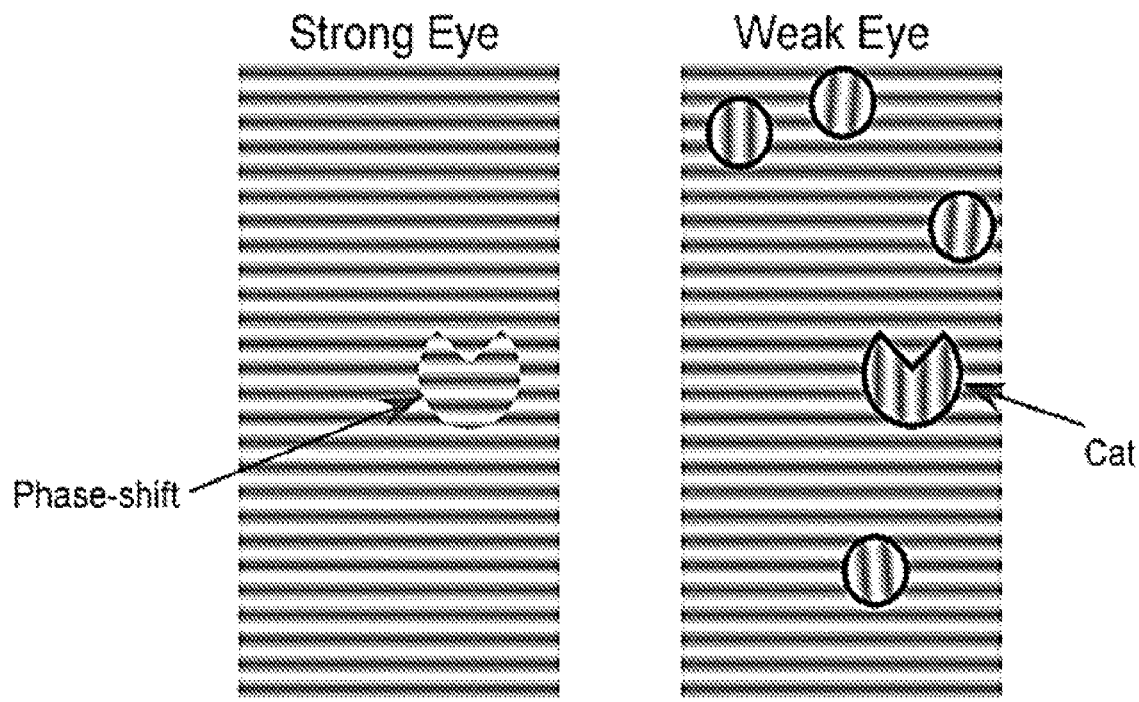
FIG. 8 illustrates a variant of the "cat and mouse" embodiment for a subject who is capable of binocular fusion. The difficulty was increased by adding weak boundary contours to the strong eye. This was done by phase-shifting selected areas of the grating in the strong eye that corresponded to the cat grating seen by the weak eye.

During the trial, visual stimulus presented to the dominant eye may be solely the background grating, but may also include one or more grating discs that are optionally outlined and are co-planar with the background. In certain embodiments, such images, when presented, may be indicated by a phase shift from the background grating in any amount between about 0° to 180° (as illustrated in FIG. 8). Preferably, however, one or more phase shifted discs are only presented to a subject able to fuse the images provided to both eyes. To this end, if the user is unable to fuse such images, then the dominant eye typically receives only the background grating. If the user is able to fuse such images, then the user may receive only the background image, or may receive the background image with one or more phase shifted discs. In certain preferred embodiments, grating discs are only provided to the dominant eye when the image provided to the non-dominant eye is substantially orthogonal or otherwise angled relative to the background such that the image in the non-dominant eye is preferred.

Once the subject is presented with the series of images, he or she uses a controller to manipulate the primary stimulus such that it moves closer to and, ultimately, contacts (or "eats") the secondary stimulus. If the user contacts the correct secondary stimulus (i.e. the stimulus that has the same orientation as the primary one) then a positive feedback is awarded. If the user contacts the incorrect secondary stimulus (i.e. the stimulus that does not have the same orientation as the primary one), then a negative feedback is provided. While not intending to be limiting to the invention in any way, such an embodiment is referred to in the examples as a "cat and mouse game" where the object is for the cat (the primary stimulus) to catch the target mouse (the secondary stimulus having the same orientation as the primary stimulus) while avoiding the poisonous mice (the secondary stimuli having a different orientation than the primary stimulus).

As suggested above, the orientation and features of the discs may be varied to alter the challenge in the treatment. Examples of variation include the size of the stimuli, the orientation of the stimuli (orthogonal, oblique, or phase shifted relative to the background), size of a contour boundary ring surrounding the stimuli, the addition of a flashing component to a disc, disc contrast, stimulus size, mean luminance intensity, jitter, and combinations thereof, wherein one or more of these variations make distinguishing from among the secondary stimuli more or less difficult. Changes, for example, may be in contrast of the visual stimuli and/or mean luminance intensity, which in certain embodiments may or may not be detectable by the subject. In other embodiments, the change may be the addition of one or more signal enhancers, such as but not limited to, the addition of a contour ring to the visual stimuli, the addition of visual stimulus jitter, the addition of visual stimulus counterphase motion, or the like. As used herein, the term "jitter" refers to the small magnitudes of displacement of the visual stimulus in organized or random directions. The level of displacement, direction of movement and/or frequency of motion may be any level such that jitter may be observed by a subject. In certain non-limiting embodiments, the displacement may be at, about, or within 0.1°. They may occur at a speed of at, about or within 4°/sec and/or at a frequency of at, about, or within 5 Hz. As used herein the term, "counterphase motion" refers to the movements of the grating inside each disc stimulus in a back-and-forth direction. The level of such movements, e.g. speed and frequency, may be any amount such that the counterphase motion may be observed by a subject. In certain non-limiting embodiments, the counterphase motion may occur at a speed of at, about, or within 4°/sec and/or at, about or within a frequency of 5 Hz. Such augmentations may be detectable, and in certain embodiments reportable, by the observer.

In addition (or alternatively) portions of one or more of the discs may be removed such that it appears to the observer that the disc has a hole. The instructions provided to the subject concerning the target stimulus will take into consideration such variable such that the user must evaluate each of them before determining which disc matches each criteria and which does not.

The position of each of the secondary stimuli in the subject's field of vision may be randomly altered during the course of treatment, i.e. during the game. In certain non-limiting aspects, the secondary stimuli may be moved in any direction and amount of time between continuous movement to movement about every 1 to about every 15 seconds, movement about every 1 to about every 10 seconds, movement about every 5 to about every 10 seconds. To this end, the user must track the movement of the targeted secondary stimulus and direct movement of the primary stimulus to its location. In certain aspects, the targeted secondary stimulus may be temporarily removed (or "hiding") from the field of vision of the user.

In further embodiments, the orientation of the primary and secondary stimuli presented may also change during the course of treatment. Such a change could result in a new targeted secondary stimulus, a new primary stimulus, or the targeted secondary stimulus and/or primary stimulus may remain the same.

The present embodiment may optionally include periodic testing to ensure the user's non-dominant eye is being preferred. During the course of a trial or treatment the user may be required to report (through verbal feedback or actuation of a portion of a controller) if he or she momentarily perceived the grating from the strong eye. To test reliability of such report, in certain aspects and referring to FIG. 2F, the primary and/or secondary stimuli may include, momentarily, a hole within the image or the perception of the background grating in some portion of the stimuli. Such a hole would give the perception of visualization by dominant eye and should elicit a response from the user, i.e. the report of seeing the orthogonal grating.

The treatment can include a single trial wherein, the user matches the primary stimuli to the secondary stimuli to end the treatment. In certain non-limiting embodiments, however, the treatment includes a series of trials where after the primary stimuli is matched to the secondary stimuli the first trial ends and a new trial begins, which may be easier or harder (based on a change of one or more variables discussed above and performance of the user in the preceding trial). The trials may continue until a certain predetermined number are complete or for a certain predetermined length of time. A subject's performance in each trial and/or treatment can be measured by the speed or efficiency of the completion of each trial. In certain embodiments, for example, the subject may be awarded points, or some other positive reinforcement, for contacting each of the primary stimuli with the secondary stimuli, where the number of points can be fix or varied based on one of any number of parameters (such as time of contact, distance covered, etc.). Points may be deducted (or some other negative reinforcement applied) if the primary stimuli contacts an incorrect secondary stimuli.

B. Identification of Stimuli from a Matrix

Figure 19:
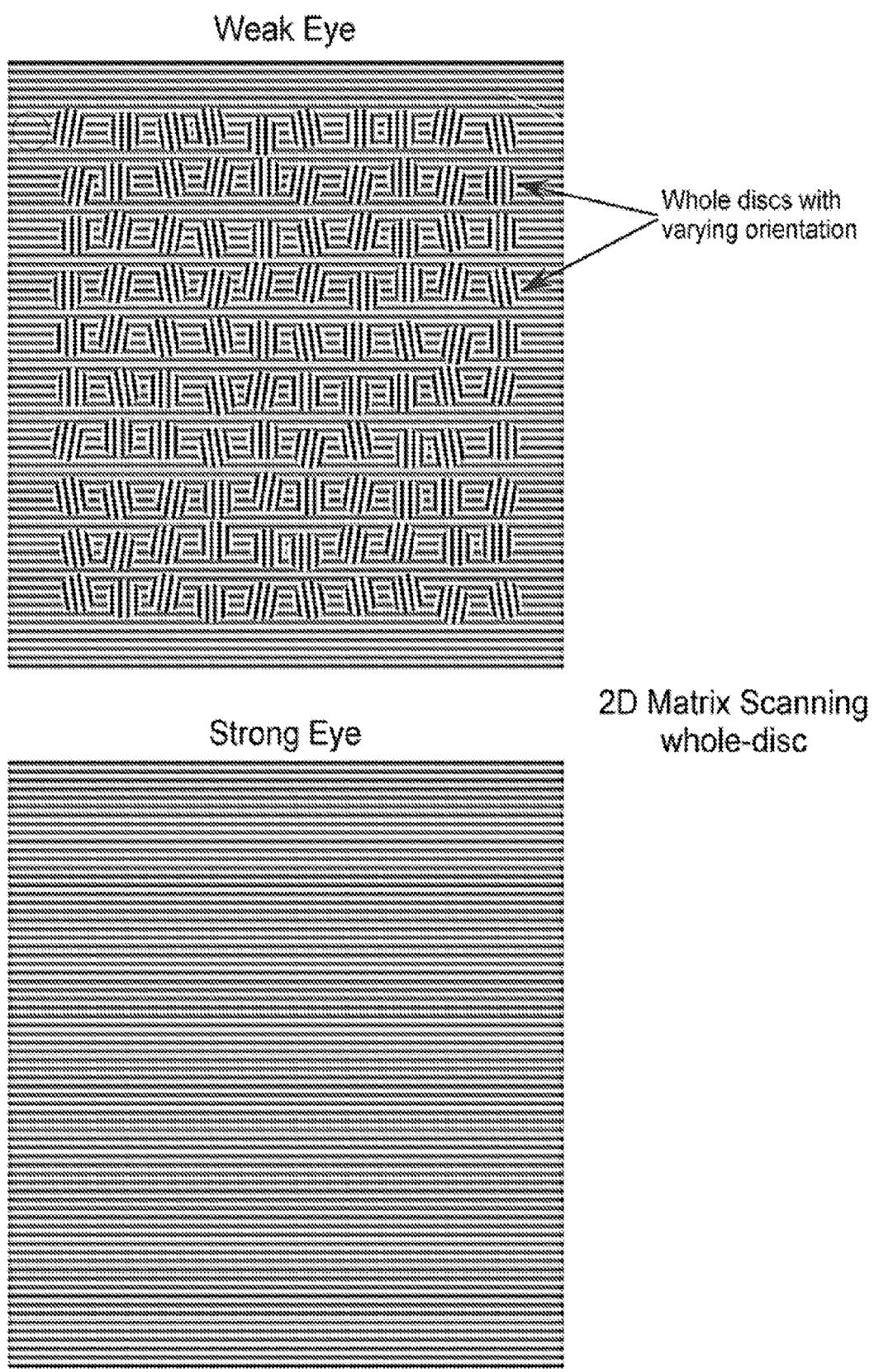
FIG. 19 provides another embodiment of a matrix of visual stimuli in accordance with the present invention. This embodiment is similar to FIG. 13 except that the markers were removed and instead of manipulating binocular disparity (phase-shift and slant), the disc orientation was manipulated. The subject's task was to select the target disc with a specific orientation (e.g., 90° from among 85° and 95° discs).

In another embodiment of the invention, the user identifies a targeted visual stimulus from among a matrix or series of dissimilar stimuli. The background to both the dominant eye and non-dominant eye is provided as a horizontal or vertical grating, though in certain aspects the background grating may be diagonal or at an oblique angle. Against this background, an optional series or matrix of markers (e.g. dots) are provided, which may be provided to both the dominant and non-dominant eyes. The visual stimuli are presented to the non-dominant eye between these markers (if present). Non-limiting examples where such markers are included are illustrated in FIGS. 12-15 and a non-limiting example where such markers are not included is illustrated in FIG. 19.

In certain aspects, the visual stimuli provided to the non-dominant eye are preferably, though not exclusively, a series or matrix of grating discs. The discs are, in certain aspects, provided at an oblique or orthogonal orientation relative to the background grating (as illustrated in FIG. 19) or are otherwise phase shifted from the background grating in any amount between greater than about 0° to less than about 180°.

In certain aspects of the foregoing embodiment, the orientation and/or features of the series or matrix of visual stimuli presented to the non-dominant eye are unique relative to each other and the background. That is, in certain aspects, most (if not all) visual stimuli has a unique angle, phase shift, and/or feature relative to the background gratings and relative to each other. To this end, in certain aspects no two visual stimuli are alike. In further embodiments, however, the matrix may include a wide variety of orientations and features where some of the stimuli are the same. While the stimuli may be arranged randomly, in certain embodiments, they are provided in a pattern or matrix, and in certain preferred embodiments they are approximately centered between four markers in the background (as illustrated in FIGS. 12-15) or are otherwise presented in a similar matrix organization (as illustrated in FIG. 19).

While the present invention is not limited to any particular number of visual stimuli presented, in certain preferred aspects, the matrix or series is defined by two or more discs. In certain embodiments, the matrix may be provided with between about 2 and about 1,000 discs; with between about 2 and about 500 discs; with between about 2 and about 100 discs. In certain embodiments the matrix is presented having an equal number of discs in each column and row, as illustrated in FIGS. 12-15 and 19.

The visual stimulus to the dominant eye may be solely the background (e.g. horizontal, vertical, or oblique/diagonal), but may optionally include one or more grating discs that is phase shifted from the background in any amount from greater than about 0° to less than about 180°. Preferably, however, one or more phase shifted discs are only presented to a subject able to fuse the images provided to both eyes and only if the images presented to the non-dominant eye are orthogonal or oblique to the background. To this end, if the user is unable to fuse such images, then the dominant eye typically receives only the background grating. If the user is able to fuse such images, then the user may receive only the background image, or may receive the background image with one or more phase shifted discs. In certain preferred embodiments, grating discs are only provided to the dominant eye when the image provided to the non-dominant eye is substantially orthogonal or otherwise angled relative to the background such that the image in the non-dominant eye is preferred.

Using video game concepts, the user is then instructed to scan the series or matrix, preferably (though not exclusively) in a certain order (e.g. top to bottom and left to right), to identify the disc(s) having a certain orientation, feature, or combination thereof. Using a controller the subject may manipulate a target cue (such as a hollow ring, X or some other feature viewed by the non-dominant eye) such that it moves closer to and, ultimately, contacts or overlaps with the stimulus desired. The user may optionally actuate a portion of the controller to indicate when the target cue is in the place desired or the action of contacting the disc with the target cue and leaving the cue in contact with the disc for a period of time to indicate the targeted disc. If the user contacts the correct stimulus (i.e. the stimulus that matches that from the instructions) then a positive feedback is awarded. If the user contacts an incorrect stimulus (i.e. a stimulus not having the same characteristics and features as the instructions), then a negative feedback is provided.

The orientation and features of the discs may be varied to increase challenge in the treatment. Examples of variation include width of a boundary contour ring surrounding the stimuli, the addition of a flashing component to a disc, disc contrast, stimulus size, mean luminance intensity, jitter, and combinations thereof, wherein one or more of these variations make distinguishing from among the secondary stimuli more difficult. For examples, the changes may be in contrast of the visual stimuli and/or mean luminance intensity, which in certain embodiments may or may not be detectable by the subject. In other embodiments, the change may be the addition of one or more signal enhancers, such as but not limited to, the addition of a contour ring to the visual stimuli, the addition of visual stimuli jitter, the addition of visual stimuli counterphase motion, or the like. As used herein, the term "jitter" refers to the small magnitudes of displacement of the visual stimuli in organized or random directions. The level of displacement, direction of movement and/or frequency of motion may be any level such that jitter may be observed by a subject. In certain non-limiting embodiments, the displacement may be at, about, or within 0.1°. They may occur at a speed of at, about or within 4°/sec and/or at a frequency of at, about, or within 5 Hz. As used herein the term, "counterphase motion" refers to the movements of the grating inside each disc stimulus in a back-and-forth direction. The level of such movements, e.g. speed and frequency, may be any amount such that the counterphase motion may be observed by a subject. In certain non-limiting embodiments, the counterphase motion may occur at a speed of at, about, or within 4°/sec and/or at, about or within a frequency of 5 Hz. Such augmentations may be detectable, and in certain embodiments reportable, by the observer.

Figure 12:
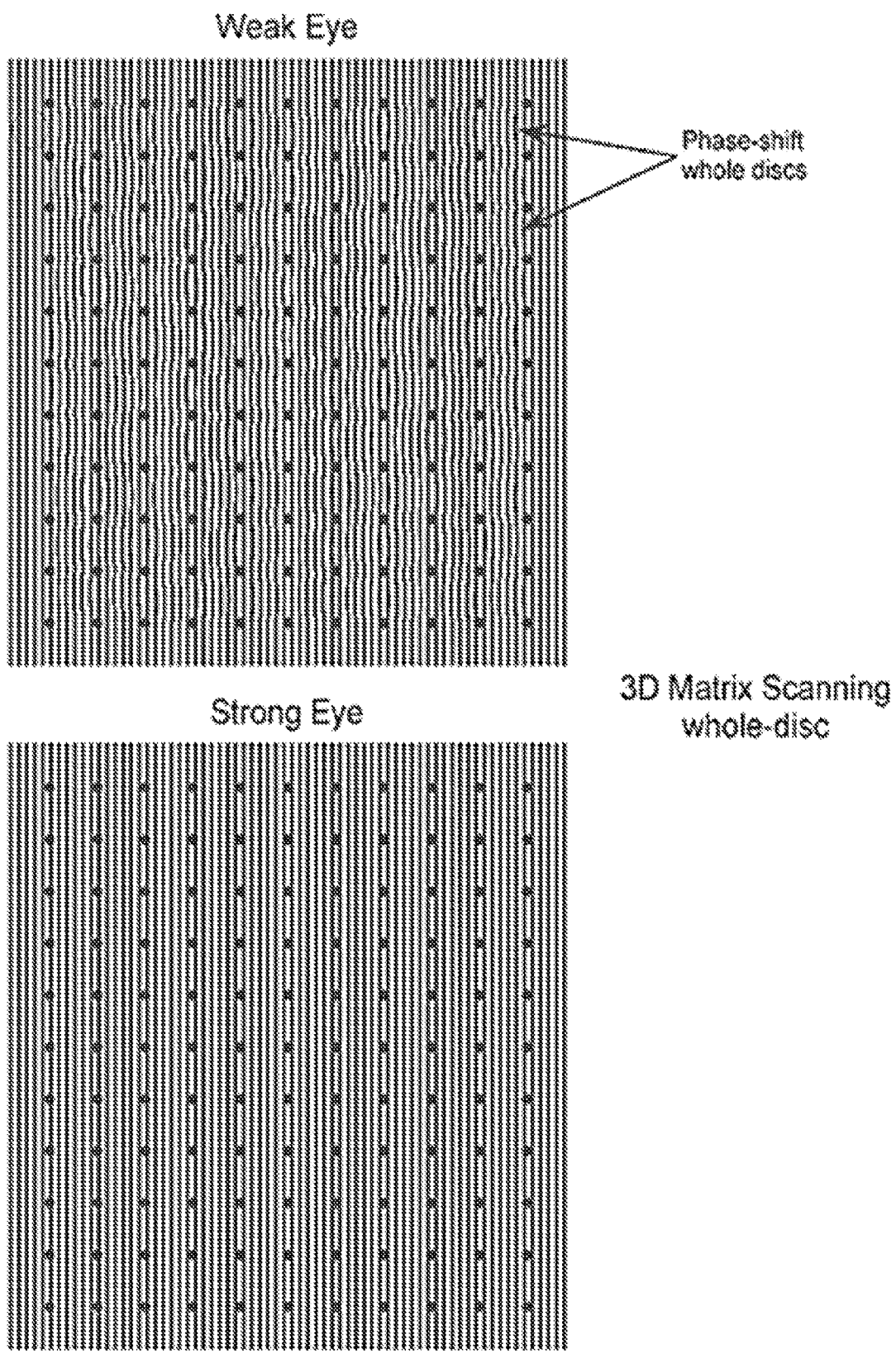
FIG. 12 provides one embodiment of a matrix of visual stimuli in accordance with the present invention. Presented to the weak eye were small circular disc areas that were phase-shifted relative to the larger vertical grating seen by the strong eye. Phase-shifting the grating leftward or rightward rendered a disc in either crossed or uncrossed binocular disparity and made it appear, respectively, as in front or behind the larger vertical grating background.
Figure 13:
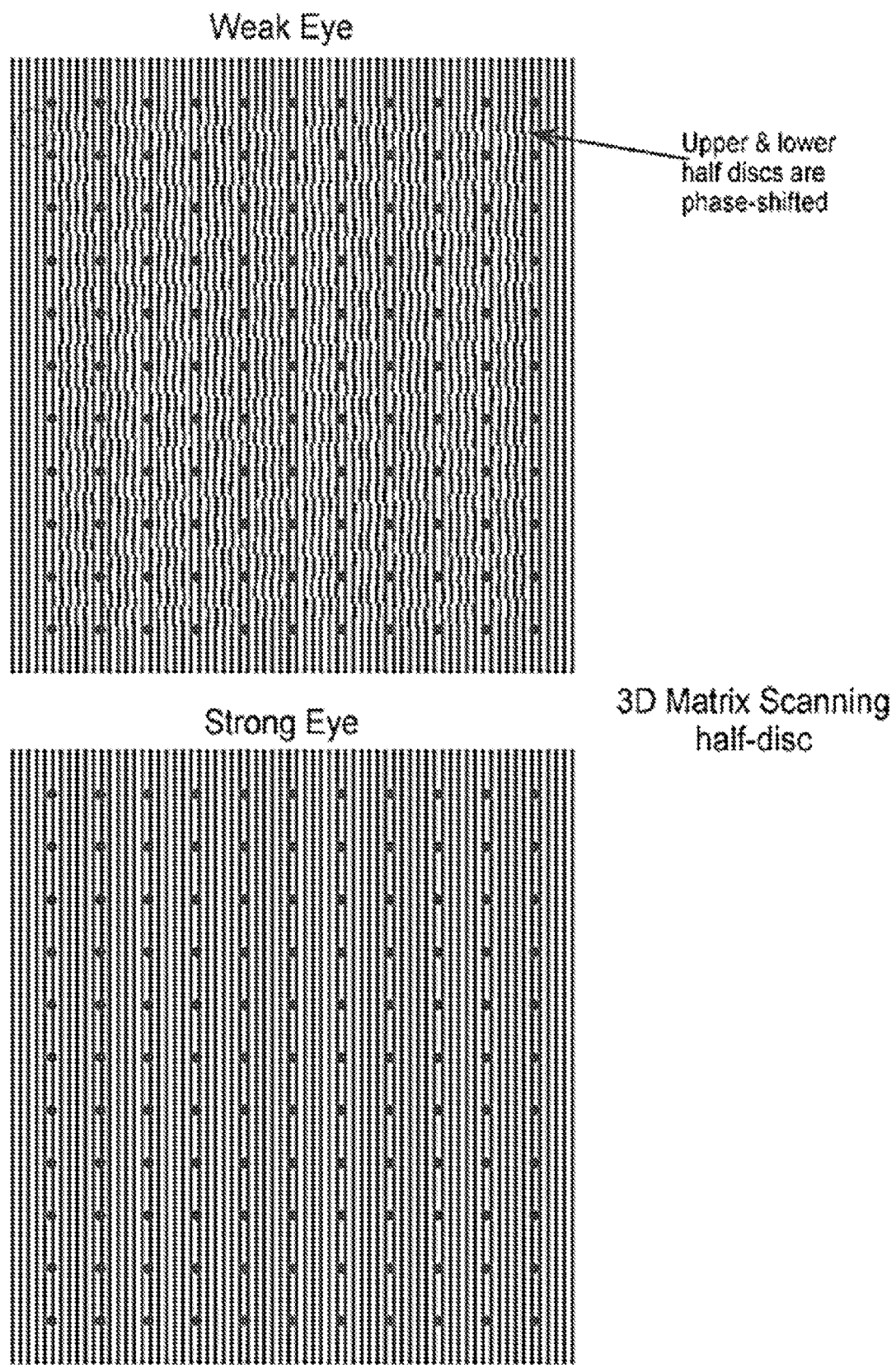
FIG. 13 provides another embodiment of a matrix of visual stimuli in accordance with the present invention. Rather than phase-shifting the entire disc as in FIG. 12, each disc was divided into upper and lower halves. Each half disc was laterally phase-shifted relative to its counterpart in opposite directions, rendering one half-disc to be seen in front and the other half-disc to be seen behind the larger vertical background.

In certain aspects, for example, the orientation of the visual stimuli is presented to provide a three dimensional visual effect. By way of non-limiting example, in certain aspects and as illustrated in FIG. 12, the visual stimuli presented to the non-dominant eye are phase shifted so as to appear in front of, or behind, the background grating. In alternative embodiments, and as illustrated in FIG. 13, an upper portion of the grating disc may be phase shifted (and optionally angled) relative to the background in one direction and the lower portion of the grating disc may be phase shifted (and optionally angled) in an opposing direction giving the effect of being in front of, or behind, the background. In other embodiments, and referring to FIG. 14, an upper portion of the disc may be angled, relative to the background, and the lower portion may be substantially orthogonal (or otherwise angled) relative to the upper portion giving the visual effect of being concave or convex. In addition (or alternatively), and referring to FIG. 15, portions of the disc may be removed such that it appears to the observer that the disc has a hole or some other distinguishing abnormality.

The instructions provided to the subject as to which of the discs is the target will take into consideration any one or more of the foregoing variables, orientations and features. The user is required to consider each of these features with each disc as (or before) he or she determines whether the disc or image matches the predetermined target.

The treatment can include a single trial where, the user aligns the target cue to the visual stimuli to end the treatment. In certain non-limiting embodiments, however, the treatment includes a series of trials where after the target cue is matched to one or all of the visual stimuli having the predetermined criteria a new trial begins, which may be easier or harder (based on a change of one or more variables discussed above). The trials may continue until a certain predetermined number are complete or for a certain predetermined length of time. A subject's performance in each trial and/or treatment can be measured by the speed or efficiency of the completion of each trial. In certain embodiments, for example, the subject may be awarded points, or some other positive reinforcement, for contacting each visual stimulus with the target cue, where the number of points can be fixed or varied based on one of any number of parameters (such as time of contact, distance covered, etc.). Points may be deducted (or some other negative reinforcement applied) if the target cue contacts an incorrect stimulus.

C. Reaction Time to Identification of Stimuli from a Matrix

Figure 21:
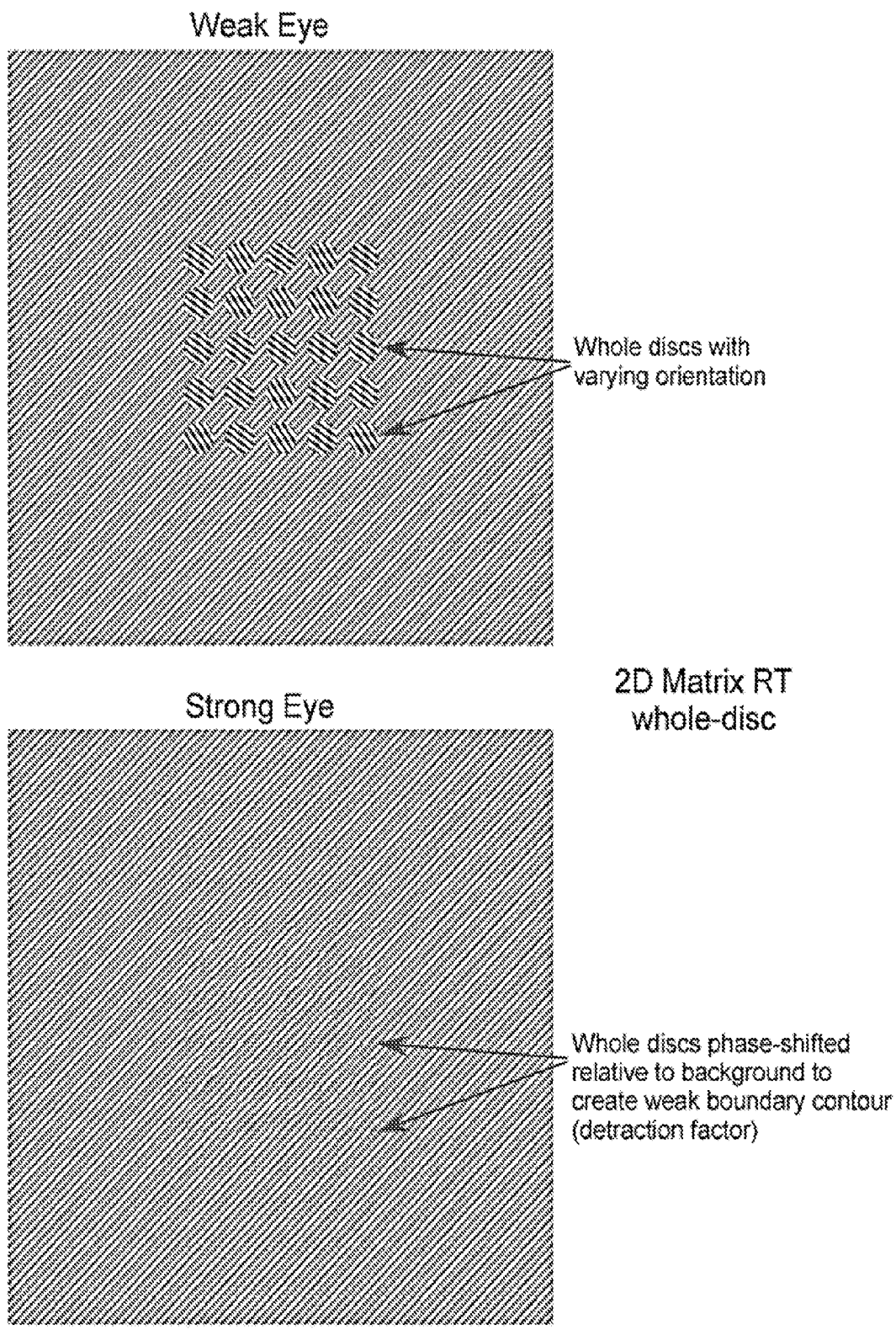
FIG. 21 provides one embodiment of a matrix of visual stimuli in accordance with the present invention which is used to measure response time in visual search. This embodiment was similar to that of FIG. 20, with two exceptions. One, the array of targets is smaller, e.g., 5×5. Two, an array could have one or more target discs, or no target disc at all. This was because the goal for the subject was to visually search, within a limited window of viewing duration (e.g., 2-10 seconds), whether the target(s) is (are) present or absent. The speed of search was recorded as the response time (RT). In this example, the stimulus seen by the strong eye's half-image has some boundary contours (detraction factor) to further challenge the weak eye to remain dominant.

In one variation of the foregoing, the user must identify a targeted visual stimulus from among a matrix of dissimilar stimuli, where the reaction time from the start of the trial to the user identification of the targeted visual stimulus is measured. Again, the background to both the dominant eye and non-dominant eye is provided as a horizontal or vertical grating, though in certain aspects the background grating may be diagonal or at an oblique angle (as illustrated in FIG. 21). Against this background, an optional series or matrix of markers (e.g. dots) are provided (as described above), which may be provided to both the dominant and non-dominant eyes. The visual stimuli (which may be provided as grating discs) are presented to the non-dominant eye between these markers (if present).

In certain preferred aspects, the series of grating discs presented to at least the non-dominant eye are such that many of the orientations of the grating discs are unique relative to each other. That is, in certain aspects, most (if not all) of the discs have a unique angle and/or phase shift relative to the background gratings and relative to each other. The discs may be arranged randomly or, in certain preferred embodiments, in a pattern or matrix. The user is then instructed to scan the arrangement, in certain embodiments in a certain order, to identify the disc(s) having a certain orientation, feature, or combination thereof.

While the present invention is not limited to any particular number of visual stimuli presented, in certain preferred aspects, the matrix or series is defined by two or more discs. In certain embodiments, the matrix may be provided with between about 2 and about 1,000 discs; with between about 2 and about 500 discs; with between about 2 and about 100 discs; with between about 2 and about 25 discs; or between about 2 and about 9 discs. In certain embodiments the matrix is presented having a equal number of discs in each column and row, as illustrated in FIG. 21.

The visual stimulus presented to the dominant eye during the trial may be solely the background grating or may also include one or more grating discs that are optionally outlined and are co-planar with the background. In certain embodiments, such images, when present, may be indicated by a phase shift from the background grating in any amount between about 0° to 180° (as illustrated in FIG. 8). Preferably, however, one or more phase shifted discs are only presented to a subject able to fuse the images provided to both eyes and only if the images presented to the non-dominant eye are orthogonal or oblique to the background. To this end, if the user is unable to fuse such images, then the dominant eye typically receives only the background grating. If the user is able to fuse such images, then the user may receive only the background image, or may receive the background image with one or more phase shifted discs. In certain preferred embodiments, grating discs are only provided to the dominant eye when the image provided to the non-dominant eye is substantially orthogonal or otherwise angled relative to the background such that the image in the non-dominant eye is preferred.

Once the series or matrix is presented, the subject then actuates a predetermined first portion of a controller, such as a button, key, joystick, or the like, if it is determined that the target stimulus is present. The subject may alternatively actuate a predetermined second portion of the controller if it is determined that the target stimulus is not present. If the user actuates the correct portion (i.e. makes a proper determination of whether the correct stimulus is present) then a positive feedback is awarded. If the user makes an incorrect determination, then a negative feedback is provided.

As with the above, the orientation and features of the discs may be varied to increase challenge in the treatment. Examples of variation include width of a boundary contour ring surrounding the stimuli, the addition of a flashing component to a disc, disc contrast, stimulus size, mean luminance intensity, jitter, and combinations thereof, wherein one or more of these variations make distinguishing from among the secondary stimuli more difficult. For examples, the changes may be in contrast of the visual stimuli and/or mean luminance intensity, which in certain embodiments may or may not be detectable by the subject. In other embodiments, the change may be the addition of one or more signal enhancers, such as but not limited to, the addition of a contour ring to the visual stimuli, the addition of visual stimuli jitter, the addition of visual stimuli counterphase motion, or the like. As used herein, the term "jitter" refers to the small magnitudes of displacement of the visual stimuli in organized or random directions. The level of displacement, direction of movement and/or frequency of motion may be any level such that jitter may be observed by a subject. In certain non-limiting embodiments, the displacement may be at, about, or within 0.1°. They may occur at a speed of at, about or within 4°/sec and/or at a frequency of at, about, or within 5 Hz. As used herein the term, "counterphase motion" refers to the movements of the grating inside each disc stimulus in a back-and-forth direction. The level of such movements, e.g. speed and frequency, may be any amount such that the counterphase motion may be observed by a subject. In certain non-limiting embodiments, the counterphase motion may occur at a speed of at, about, or within 4°/sec and/or at, about or within a frequency of 5 Hz. Such augmentations may be detectable, and in certain embodiments reportable, by the observer.

In certain aspects, for example, the orientation of the visual stimuli is presented to provide a three dimensional visual effect. By way of non-limiting example, in certain aspects an upper portion of the grating disc may be phase shifted (and optionally angled) relative to the background in one direction and the lower portion of the grating disc may be phase shifted (and optionally angled) in an opposing direction giving the effect of being in front of, or behind, the background. In other embodiments, and upper portion of the disc may be angled, relative to the background, and the lower portion may be substantially orthogonal to the upper portion giving the visual effect of being concave or convex. In addition (or alternatively) portions of the disc may be removed such that it appears to the observer that the disc has a hole or some other distinguishing abnormality.

The instructions provided to the subject as to which of the discs is the target will take into consideration any one or more of the foregoing variables, orientations and features. The user is required to consider each of these features with each disc as (or before) he or she determines whether the disc or image matches the predetermined target.

The treatment can include a single trial where, the user is presented with only one series of stimuli and makes only one determination of whether the targeted stimulus is present. In certain non-limiting embodiments, however, the treatment includes a series of trials where successive determinations are made by the subject on multiple series of stimuli. Each successive series may be easier or harder (based on a change of one or more variables discussed above and based on the subject's performance in the preceding trial). The trials may continue until a certain predetermined number are complete or for a certain predetermined length of time. A subject's performance in each trial and/or treatment can be measured by the speed or efficiency of the completion of each trial. In certain embodiments, for example, the subject may be awarded points, or some other positive reinforcement, for a correct determination, where the number of points can be fixed or varied based on one of any number of parameters (such as difficult of the series, time of determination, etc.). Points may be deducted (or some other negative reinforcement applied) if the subject makes an incorrect determination.

D. Identification of Stimuli from Memory

Figure 23:
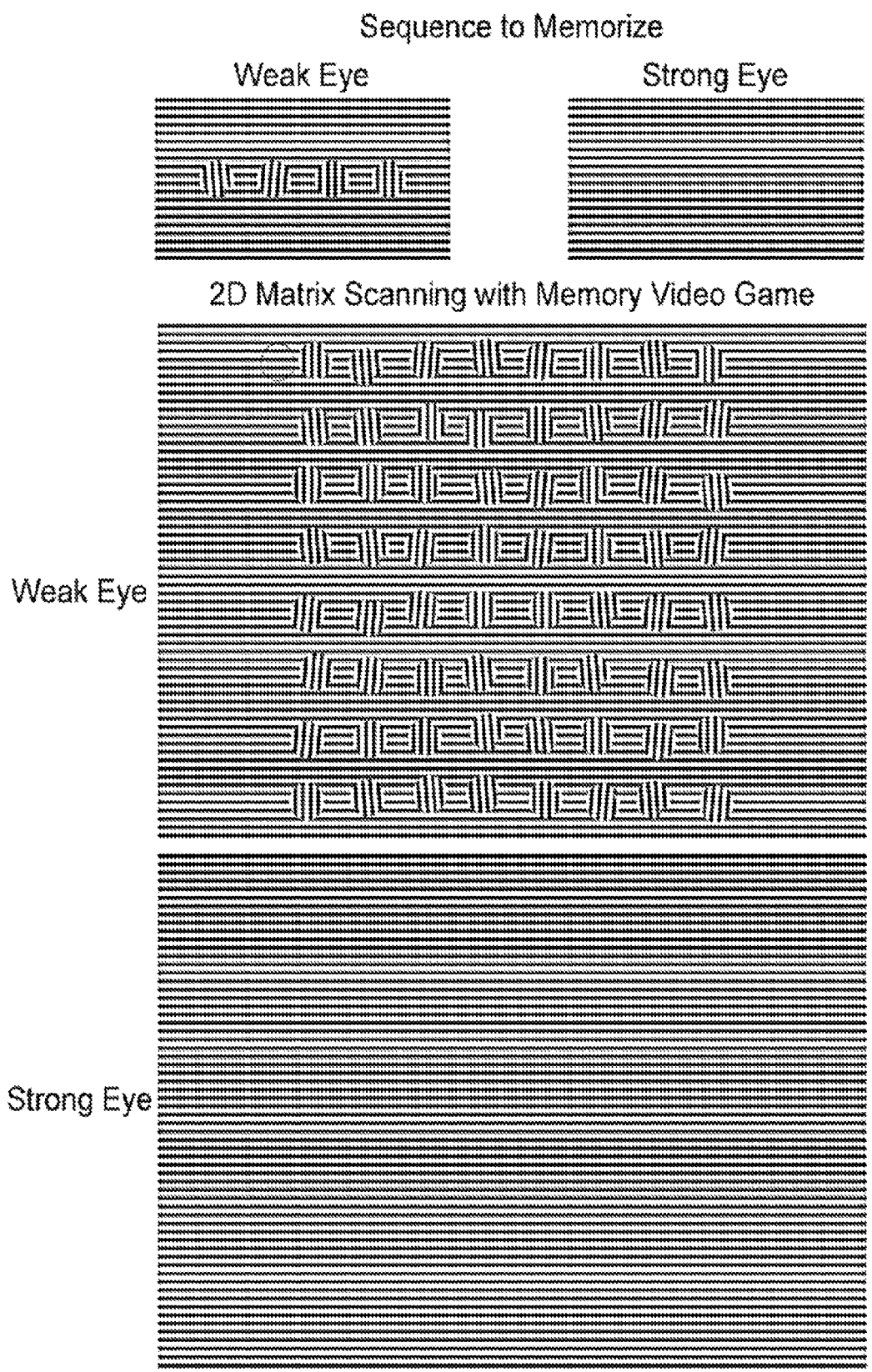
FIG. 23 provides one embodiment of a series of visual stimuli to be memorized by the observer (upper panel) and a matrix of visual stimuli containing the series memorized plus other distracting stimuli. The treatment was similar to that of FIG. 21, except that each trial was preceded by a specific sequence of targets to memorize. During the trial, the subject selected the targets based on the memorized sequence.
Figure 26:
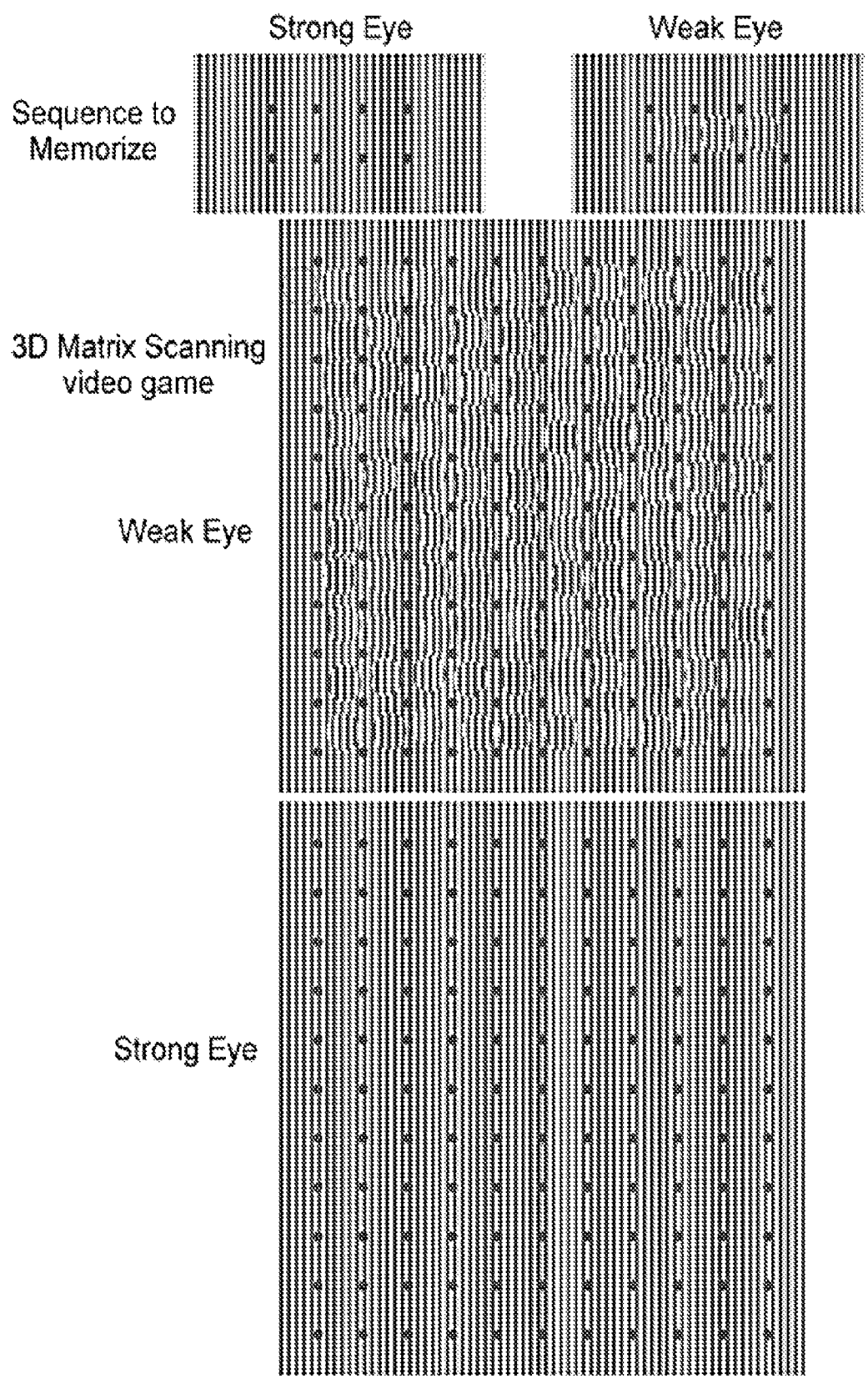
FIG. 26 provides another embodiment of a series of visual stimuli to be memorized by the observer (upper fields) and a matrix of visual stimuli containing the series to be memorized. The images are rendered 3-D by virtue of the phase-shift between the vertical grating discs and their background. Similar to the embodiment of FIG. 23 the subject's task is to select the targets from the memorized sequence.

In another variation of the foregoing, the user is asked to memorize a series of visual stimuli (such as a series of grating discs) then identify, from memory, if the same series is present in a matrix of grating discs. Again, the background to both the dominant eye and non-dominant eye is provided as a horizontal or vertical grating (as illustrated in FIGS. 23 and 26), though in certain aspects the background grating may be diagonal or at an oblique angle. Against this background, an optional series or matrix of markers are provided (as described above), which may be provided to both the dominant and non-dominant eyes. The visual stimuli are presented to the non-dominant eye between these markers (if present).

In certain preferred aspects, the first series of visual stimuli are presented to the non-dominant eye as a plurality of grating discs where the orientation and/or features of each in the series are unique relative to each other. In certain aspects, most (if not all) of the grating discs have a unique angle and/or phase shift relative to the background gratings and relative to each other. The discs may be arranged randomly or, in certain preferred embodiments, in a pattern or matrix. In certain embodiments, the first series is presented linearly. Though the number of the first visual stimuli presented is not limiting to the invention, in certain embodiments, the first series includes between about 2 and about 10 discs; between about 2 and about 5 discs; or between about 2 and about 4 discs.

While the present invention is also not limited to any particular number of visual stimuli presented in the matrix, in certain preferred aspects, the matrix is defined by two or more discs. In certain embodiments, the matrix may be provided with between about 2 and about 1,000 discs; with between about 2 and about 500 discs; with between about 2 and about 100 discs. In certain embodiments the matrix is presented having a equal number of discs in each column and row, as illustrated in FIG. 23. In further embodiments, the matrix includes the same, or preferably, a greater number of discs as the first series.

The visual stimulus presented to the dominant eye during the trial may be solely the background grating or may also include one or more grating discs that are optionally outlined and are co-planar with the background. In certain embodiments, such images, when present, may be indicated by a phase shift from the background grating in any amount between about 0° to 180°. Preferably, however, one or more phase shifted discs are only presented to a subject able to fuse the images provided to both eyes and only if the images presented to the non-dominant eye are orthogonal or oblique to the background. To this end, if the user is unable to fuse such images, then the dominant eye typically receives only the background grating. If the user is able to fuse such images, then the user may receive only the background image, or may receive the background image with one or more phase shifted discs. In certain preferred embodiments, grating discs are only provided to the dominant eye when the image provided to the non-dominant eye is substantially orthogonal or otherwise angled relative to the background such that the image in the non-dominant eye is preferred.

The user is then instructed to scan the arrangement and memorize each of the features and orientations of each disc in the series. The first series of visual stimuli is then removed and the user is presented with a second, larger, series or matrix of visual stimuli, such as a second plurality of grating discs. Again, many of the orientations and/or features of each disc in the series are unique relative to each other. That is, in certain aspects, most (if not all) of the grating discs stimuli has a unique angle and/or phase shift relative to the background gratings and relative to each other. The discs may be arranged randomly or, in certain embodiments, in a pattern or matrix. At least one portion of the second set of stimuli matches the first series of visual stimuli.

Using video game concepts, the user is then instructed to scan the series or matrix, preferably (though not exclusively) in a certain order (e.g. top to bottom and left to right), to identify the disc(s) forming the first series of visual stimuli. Using a controller the subject optionally manipulates a target cue (such as a ring, X or some other feature viewed by the non-dominant eye) such that it moves closer to and, ultimately, contacts or overlaps the stimuli identified, preferably in the order that they were presented. The user may optionally actuate a portion of the controller to indicate when the target cue is in the place desired. If the user contacts the correct stimulus (i.e. the stimulus matches that from the instructions) then a positive feedback is awarded. If the user contacts an incorrect stimulus (i.e. a stimulus not having the same characteristics and features as the instructions or not in the same order as the first series provided), then a negative feedback is provided.

In alternative embodiments, no target cue may be provided and the user may simply actuate a predetermined first portion of a controller, such as a button, key, joystick, or the like, if it is determined that the first series of stimuli is present in the second series. The subject may alternatively actuate a predetermined second portion of the controller if it is determined that the correct stimuli is not present. If the user actuates the correct portion (i.e. makes a proper determination of whether the correct stimuli is present) then a positive feedback is awarded. If the user makes an incorrect determination, then a negative feedback is provided.

The orientation and features of the discs may be varied to increase challenge in the treatment. Examples of variation include width of a boundary contour ring surrounding the stimuli, the addition of a flashing component to a disc, disc contrast, stimulus size, mean luminance intensity, jitter, and combination thereof, wherein one or more of these variations make distinguishing from among the secondary stimuli more difficult. For examples, the changes may be in contrast of the visual stimuli and/or mean luminance intensity, which in certain embodiments may or may not be detectable by the subject. In other embodiments, the change may be the addition of one or more signal enhancers, such as but not limited to, the addition of a contour ring to the visual stimuli, the addition of visual stimuli jitter, the addition of visual stimuli counterphase motion, or the like. As used herein, the term "jitter" refers to the small magnitudes of displacement of the visual stimuli in organized or random directions. The level of displacement, direction of movement and/or frequency of motion may be any level such that jitter may be observed by a subject. In certain non-limiting embodiments, the displacement may be at, about, or within 0.1°. They may occur at a speed of at, about or within 4°/sec and/or at a frequency of at, about, or within 5 Hz. As used herein the term, "counterphase motion" refers to the movements of the grating inside each disc stimulus in a back-and-forth direction. The level of such movements, e.g. speed and frequency, may be any amount such that the counterphase motion may be observed by a subject. In certain non-limiting embodiments, the counterphase motion may occur at a speed of at, about, or within 4°/sec and/or at, about or within a frequency of 5 Hz. Such augmentations may be detectable, and in certain embodiments reportable, by the observer.

In certain aspects, for example, the orientation of the visual stimuli is presented to provide a three dimensional visual effect. By way of non-limiting example, in certain aspects an upper portion of the grating disc may be phase shifted and/or angled (relative to the background) in one direction and the lower portion of the grating disc may be phase shifted and/or angled in an opposing direction giving the effect of being in front of, or behind, the background. In other embodiments, and upper portion of the disc may be angled, relative to the background, and the lower portion may be substantially orthogonal to the upper portion giving the visual effect of being concave or convex. In addition (or alternatively) portions of the disc may be removed such that it appears to the observer that the disc has a hole or some other distinguishing abnormality.

The instructions provided to the subject will take into consideration any one or more of the foregoing variables and features. The user is required consider each of these features with each disc as (or before) he or she determines whether the disc or image matches the predetermined criteria or instructions.

The treatment can include a single trial where, the user provides the order of one series of visual stimuli to end the treatment. In certain non-limiting embodiments, however, the treatment includes a series of trials where after a first series is presented and ordered, a second series is presented, which may be easier or harder (based on a change of one or more variables discussed above). The trials may continue until a certain predetermined number are complete or for a certain predetermined length of time. A subject's performance in each trial and/or treatment can be measured by the speed, efficiency, and accuracy of the completion of each trial. In certain embodiments, for example, the subject may be awarded points, or some other positive reinforcement, for the correct order, where the number of points can be fixed or varied based on one of any number of parameters (such as time to complete the trial, difficulty of the series, number of stimuli presented etc.). Points may be deducted (or some other negative reinforcement applied) if incorrect answer is given.

In any one of the foregoing embodiments, the trials or treatments, or adaptations thereof based on the disclosure provided herein, may be performed between 1-100 trials per session; 5-50 trials per session; 15-35 trials per session, or 20-25 trials per session per day over 7-15 days, or longer depending on the severity of the subject's condition. The duration of the treatment and number of trials are not limited to such amounts and will depend on the magnitude of the deficiency being corrected. To this end, the number of trials performed and length of the treatment may be of any amount to achieve the desired reduction of SED or otherwise to improve the visual characteristics associated with SED, amblyopia, poor stereopsis or the like.

The trials may be conducted on any system, particularly a computerized system, having hardware and software capabilities to provide such visual stimuli in accordance with the teachings herein. To this end, the present invention may include a computer program product/processor and a non-transient storage medium or process with a computer program stored thereon. The program is adapted, when loaded and executed on a computer, to perform the inventive method for reducing the deficiencies discussed herein and/or the associated visual characteristics provided. While not limited thereto, the program may be performed on any device having computer-based hardware capable of generating stereoscopic 3D displays or a 2D display that gives the appearance of a 3D image on a visual imaging display. Such devices include, but are not limited to, any device having one or more display screens (e.g. CRT, LCD, etc.) adapted to present each of the attention cues and/or visual stimuli in accordance with the teachings herein. In certain aspects, the device may be adapted for segregated viewing by each eye, i.e. the non-dominant eye views one screen, portion of a screen, or visual stimuli while the dominant eye views another. One example of such a device or a component of a device includes a halposcope or haploscopic mirror and/or prism system, where images presented on one or more screens are displayed only to the targeted eye using a mirror or system of mirrors and/or prisms.

In alternative embodiments, the dominant eye and non-dominant eye's images may be overlaid in a single image, wherein the two are provided with separate characteristics making them filterable such that they may be viewed by the targeted eye. By way of non-limiting example, the image intended for viewing by the dominant eye may be provided in one color (e.g. red) and the image for the non-dominant eye in a second color (e.g. green) Using filters, such as glasses having a green lens over the dominant eye and a red lens over the non-dominant eye, only the proper image is detected by the desired eye. That is, the green lens prevents the dominant eye from detecting the red portion of the image and the red lens prevents the non-dominant eye from detecting the green portion of the image. Thus, only one image is provided to the dominant eye and only one image is provided to the non-dominant eye. Additional devices, systems, and methods of providing separate images to the eyes of a patient will be readily apparent to one of skill in the art, based on the disclosure provided herein.

The device may also contain one or more features for observer or a subject's feedback. By way of non-limiting example, in certain aspects, the system or device may include a button, controller containing a series of buttons, joysticks or some other actuatable mechanism where, when subject feedback is requested during a trial, actuation of the mechanism serves to provide such feedback.

Prior to, during, and/or after the treatment, the extent of a subject's SED, stereopsis, or other visual deficiencies may be quantified using any standard technique for measuring binocular visual functions. Such measurements may be used to establish a baseline binocular vision, including interocular imbalance, and to track the progress of the subject through the treatment regimen. To this end, a preliminary measurement may be taken prior to treatment and compared against subsequent measurements taken before and/or after each course of treatment or periodically during the treatment process. Such information can also be used to determine whether additional or further courses of treatment are desirable, if the trials should be made harder or easier, and/or if the subject experiences relapse after the treatment is complete.

While any method of measuring such imbalances may be used, in certain non-limiting aspects SED and/or interocular imbalance is measured using a binocular rivalry stimulus with varying intensities or contrasts between half images. Generally, (and referring to FIGS. 4 and 5) a fixation target is provided to both eyes and then different stimuli are presented to both the dominant and non-dominant eyes where only one of the stimuli is detected. Sometimes, a mixture of both eyes' stimuli is detected. In either event, the observer chooses the predominant orientation seen. The contrast and/or intensities of the non-detected stimuli is then altered in a gradually increasing manner until each eye's stimulus has an equal chance to be seen. This test is performed for both eyes to establish a collective right eye and left eye balance contrasts.

Figure 5:
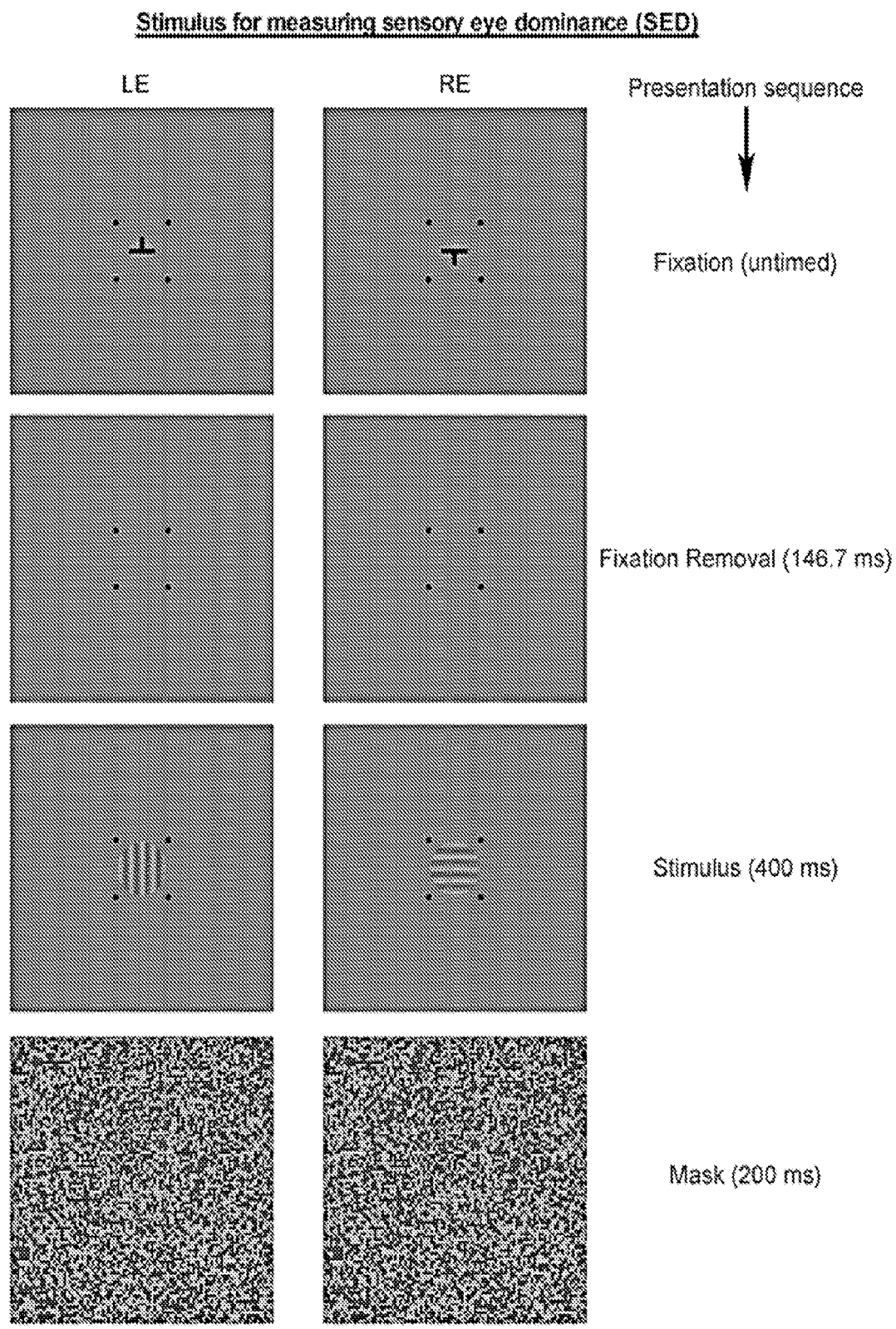
FIG. 5 illustrates one embodiment of the stimulus presentation sequence for the SED stimuli described in FIG. 4 and Examples 2 and 3.

The balance contrast may be measured in the foveal region of the eye and/or at varying degrees from the foveal region in the parafoveal and/or peripheral retinal regions. The stimuli are preferably, though not exclusively, provided as gratings against either a blank or grating background. Depending upon the type of background, the gratings may be parallel or at an angle to each other. By way of example, (and as illustrated in FIGS. 4 and 5) in certain embodiments the stimuli of each eye are orthogonally oriented such that the grating in one eye is approximately 90° to the other.

In one non-limiting embodiment, the balance contrast is measured in each eye. Specifically, the subject is presented with dichoptic orthogonal gratings against a blank backdrop (as defined above), where the first eye is focused on, typically horizontal, grating with a constant contrast. The contrast of the second grating is increased until the observer reports an equal chance of visualizing the constant contrast grating with the first eye and the variable contrast grating with the second eye. This establishes the balance contrast of the second eye. The technique then reversed to establish the balance contrast of the first eye, i.e. the second eye visualizes the constant contrast grating and the first eye the variable one. The eye with the higher balance contrast is considered the non-dominant eye.

In certain embodiments of the foregoing, the constant contrast grating is provided as a horizontal grating disc and the variable contrast grating as a vertical grating disc. The present invention is not limited to vertical and horizontal gratings and may be adapted to provided pairs of gratings with any angular orientation, where the two gratings are or may not be orthogonally oriented.

In another embodiment, more than one grating disc, e.g. a set of six grating discs arranged in concentric circles around the fovea, are presented to each eye. This measures the global balance contrast. The two sets of discs presented to the two eyes have orthogonal orientation and different colors. Balance contrast is obtained for each eye by adjusting either the intensity and/or contrast of the entire set of discs in one eye while the other eye views discs of fixed intensity and contrast.

An alternative measurement method similarly detects interocular imbalance. More specifically, a grating background is presented to each eye of the observer with a pair of dichoptic orthogonal grating discs within each field. The background is preferably provided to both eyes in the same orientation, which may be vertical, horizontal or oblique. The disc in a first eye is orthogonal to the background grating. The disc in the second eye is parallel to the background grating with a variable phase-shift (0-180 degrees) relative to the background. The phase shift of this latter grating is increasingly adjusted until the observer acknowledges an equal chance of seeing both discs. This establishes the balance phase shift of the second eye. The measurement is then reversed to determine the balance phase shift of the first eye, and the eye with the higher balance phase shift is considered the non-dominant eye.

In another non-limiting embodiment, the relative strengths of the two eyes are measured using a binocular rivalry tracking method. Specifically, referring to the stimuli shown in FIG. 1a, the subject views the orthogonally oriented dichoptic stimuli for an extended duration, e.g. 1 minute. He or she tracks, i.e. reports by selective key presses, whether he or she perceives more vertical or more horizontal grating within the disc area. This allows us to calculate the predominance of seeing the vertical disc by one eye (weak eye in this example). Then the stimuli in the two eyes are switched, so that the strong eye sees the vertical disc, and the strong eye's predominance is calculated. Finally, the ratio of predominance of the weak eye to strong eye is calculated, which provides a measure of sensory eye dominance. A ratio of unity indicates balanced eyes.

Figure 6:
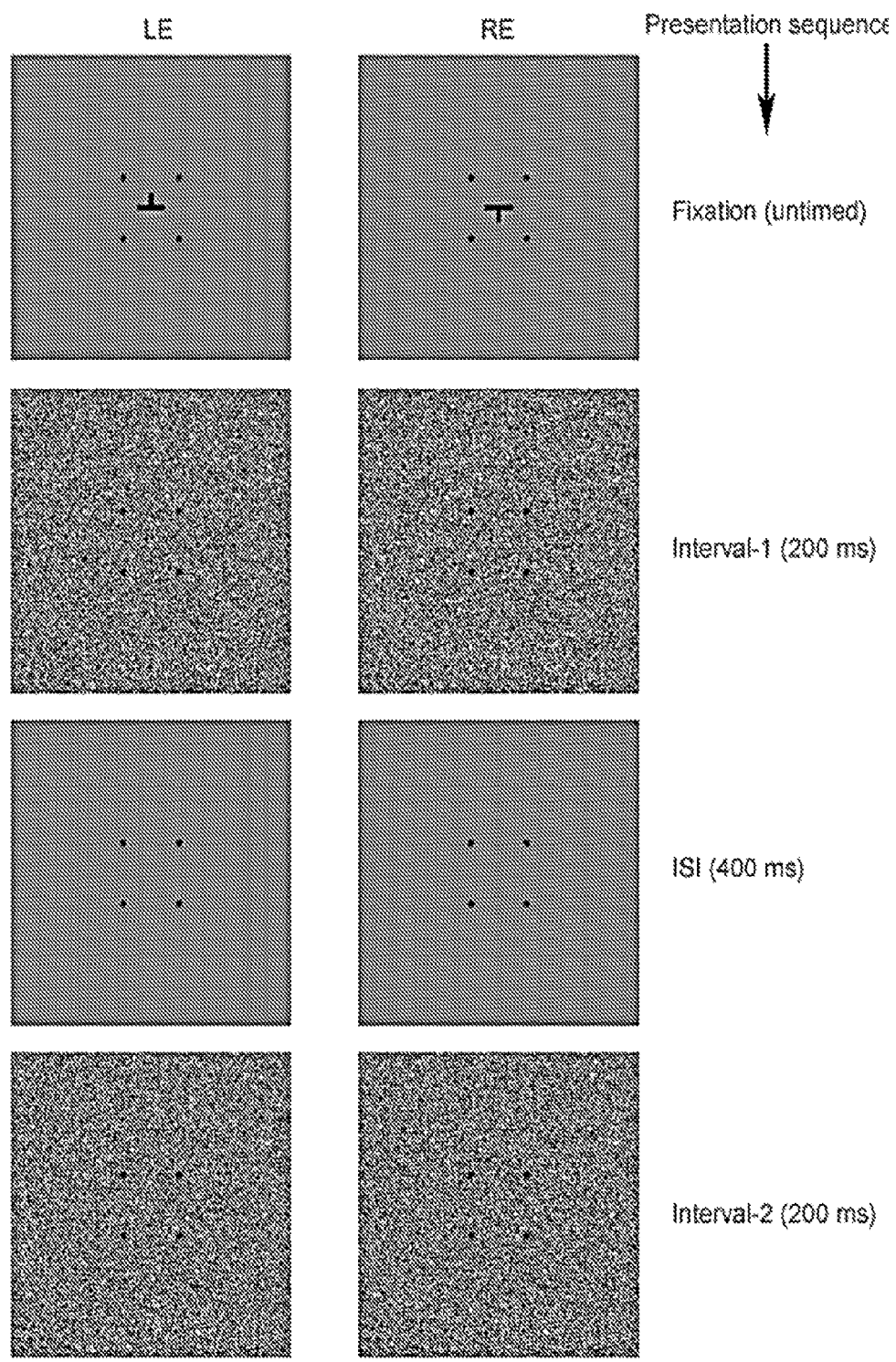
FIG. 6 illustrates one embodiment of the stimulus presentation sequence for measuring stereopsis threshold.
Figure 7:
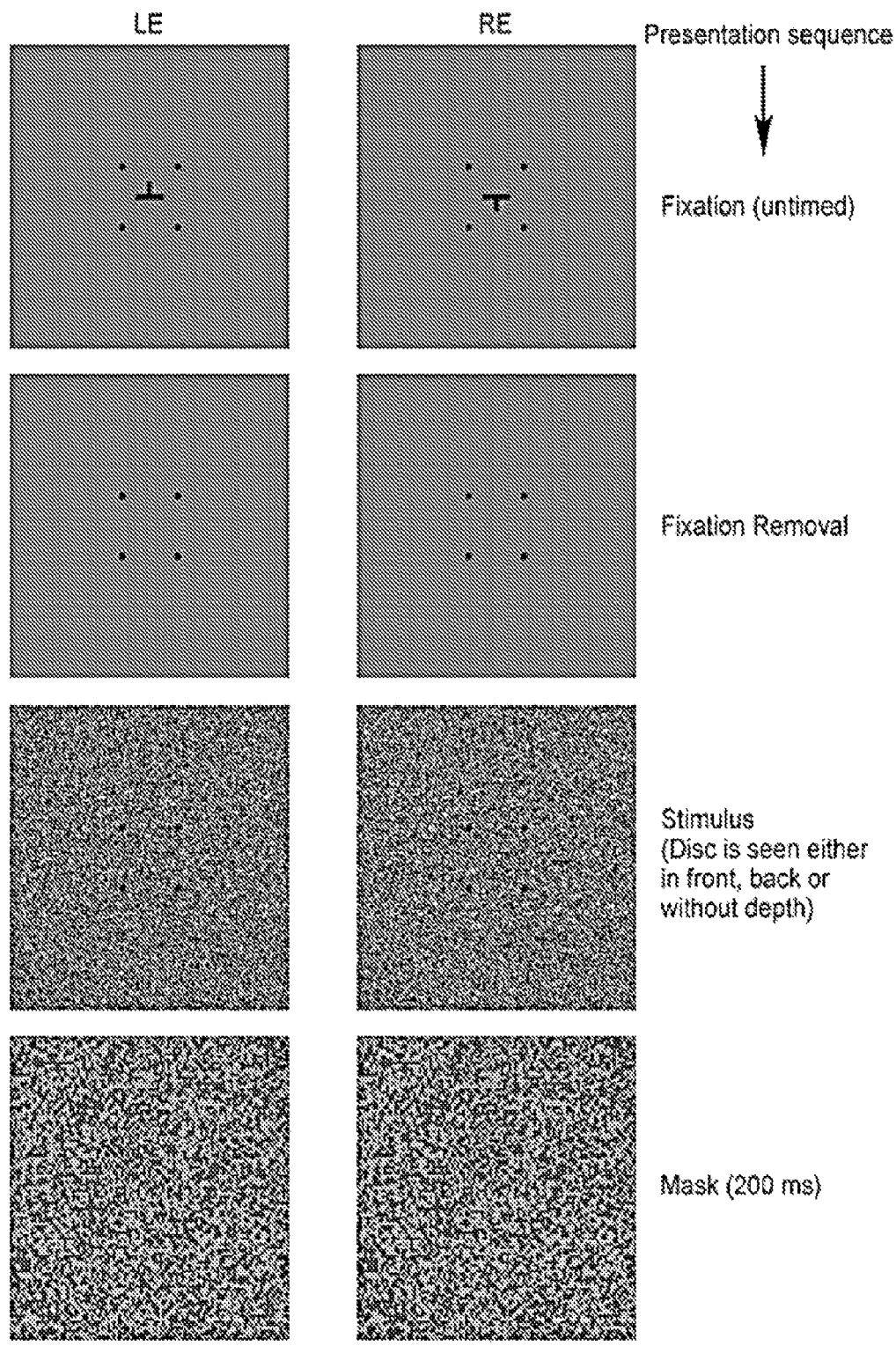
FIG. 7 illustrates one embodiment of the stimulus presentation sequence for measuring stereopsis response time.

In even further alternatives, a stereopsis profile of the subject may be established before, during and after testing. More specifically, and referring to FIG. 6, stereo threshold may be measured using the standard 2AFC method in combination with the staircase procedure. That is, the observer indicates whether a crossed-disparity disc was perceived at interval-1 or -2. Referring to FIG. 7, stereo response time was measured by presenting a disc with crossed disparity (front), uncrossed disparity (back) or zero disparity (flat) to the subject. The observer then responds to the seen depth as soon as possible by pressing the appropriate key on the computer keyboard or actuation of a controller (as provided herein).

SED balance, stereopsis measurements and the like may be taken in the foveal region)(0°) or at varying concentric locations therefrom in the parafoveal and peripheral retinal regions. In one aspect, such measurements are taken at a 2° eccentric retinal location at one position or concentrically throughout the visual field, i.e. 0°, 45°, 90°, 135°, 180°, 225°, 270°, 315° around the foveal region. In further embodiments, a localized map of SED, interocular imbalance and/or stereopsis can be obtained for each observer by taking such measurements at increasing eccentric retinal locations through the field of vision. By way of non-limiting example, such measurements may include concentrical measurements through the field vision at 1°, 2°, 4°, 8°, 10°, etc. from the foveal region. This map may be used as a basis for selecting locations that may be targeted for treatment, or otherwise to measure the effects of the treatment at a multitude of locations throughout the subject's field of vision.

The following are examples of the invention and are not to be construed as limiting.

EXAMPLES

Example 1: Training with the Two-Dimensional "Cat and Mouse" Embodiment for a Subject without Fusion Ability Due to Strabismus Observer:
A female in her twenties with constant esotropia and RE amblyopia participated in the study. She was last treated for amblyopia with the patching method more than 15 years ago. Her visual acuities were 20/80 (RE) and 20/15 (LE). She was not able to perceive stereopsis due to the lack of binocular fusion ability.

Procedures:
The observer's SED was measured in the foveal region using the binocular rivalry tracking method. As shown in FIG. 1, the stimulus comprised either a vertical disc (a) or horizontal disc (b) surrounded by an orthogonal grating half-image in one eye and the same orthogonal grating half-image in the other eye. The observer was tasked to respond to her instantaneous perception of the oriented grating within the disc area, over a stimulus viewing duration of 1 minute. By presenting the disc half-image to the weak eye, how often the weak eye sees the disc was measured to gauge its SED before and after the Push-Pull training using the cat and mouse embodiment of the present invention. An increased in the percentage of time in seeing the disc after the training would indicate reduced SED.

The basic design of the cat and mouse stimulus, as shown in FIG. 2a, comprised a homogeneous grating viewed by the strong eye and the same homogeneous grating plus small disc-like cat and mouse targets with an orthogonal orientation viewed by the weak eye. The cat and mouse targets were rendered in motion. The latter (mouse target) moved in semi-random speeds and directions. The trial required the subject to move the cat (a designated grating disc with a notch removed) to contact or "swallow" the mouse (another designated grating disc) whose orientation was the same as the cat's orientation. The cat and mouse targets had clearly defined boundary contours (outlines) that guaranteed their visibility for the entire duration (2 minutes per trial), i.e., dominance of the weak eye (push) and suppression of the strong eye (pull). The outline rings can be optionally flashed on/off by changing it from white ring to black ring throughout the trial. This enhances the dominance of the weak eye. The subject manipulated select keys on a computer keyboard to play.

FIG. 2b shows that the difficulty levels can be increased by: (i) adding distracting targets in the form of "poisonous" mice with slightly different orientations from the target mouse; (ii) having the target mouse escaping from view by running into its hiding; (iii) switching the orientation of the cat and mouse at random every 5-10 seconds to require the subject to catch a different mouse. Essentially, besides the primary training goal of reducing SED with the Push-Pull paradigm, the present invention also secondarily trains other visual tasks including orientation discrimination, transient attention acquisition, pursuit eye movement, eye-hand coordination, and quick responses.

A variety of enhancement factors can be used to guarantee the dominance of the weak eye. These include, but are not limited to: (a) adding boundary contours (rings) to the discs (cat and/or mice) (FIGS. 2b and 2c); (b) varying the thickness of the boundary contours (FIG. 2d); or (c) varying the contrast of the cat/mice (FIG. 2e). The examples in FIG. 2 are shown with grating sets of different orthogonal orientations, which could be used to train the various visual orientation channels (0°, 90°, 45°, 135°). The subject in the current Example was trained with a stimulus having 90° grating orientation (e.g., FIG. 2b).

Figure 2F:
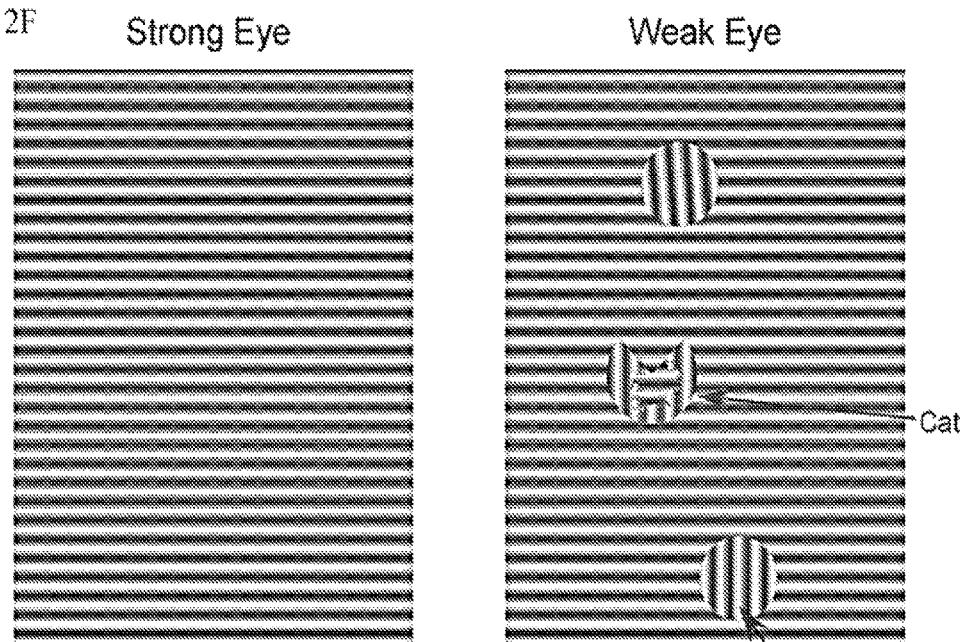
Figure 3A:
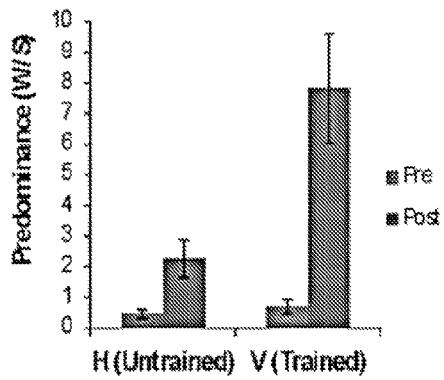
FIGS. 3A-D illustrate improved ability of the weak eye to see the grating disc of the binocular rivalry stimulus after training with the "cat and mouse" embodiment of the present invention, i.e. it indicates a reduction in SED.
Figure 3B:
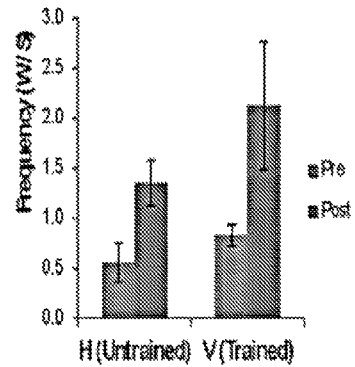
Figure 3C:
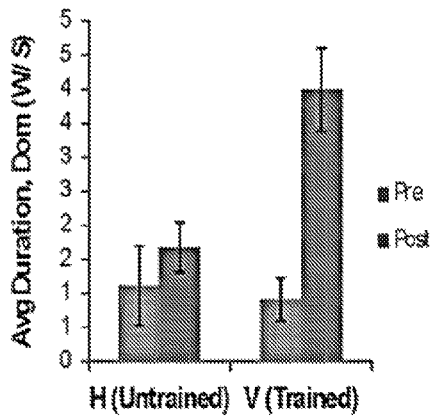
Figure 3D:
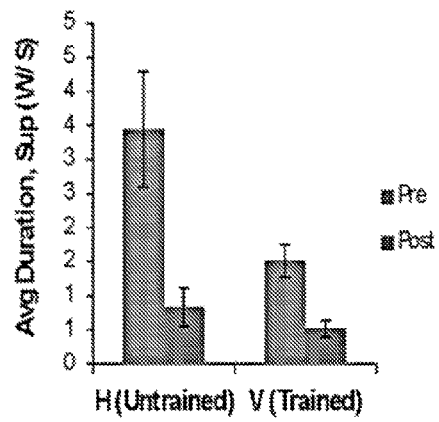

To ensure that the subject's weak eye was dominant, the subject was required to report if she momentarily perceived the orthogonal grating from the strong eye. But doing so required the subject to be reliable. To test her reliability, a catch trial was added, wherein the momentarily perception of the orthogonal grating from the strong eye was simulated by adding the stimulus in the cat. An example is shown in FIG. 2f. A report by the observer that this was detected suggests reliability in her visualization with the non-dominant eye over the dominant eye.

During each training session, multiple trials were played totaling up to 1.5 hours. The trials were scored in terms of the number of mice caught, and scores were deducted for catching the wrong mice. The images were provided on a computer screen where the images for the dominant eye and the non-dominant eye were overlaid and were each provided in either a red or green color. The subject viewed the computer screen using 3D glasses (red filter in RE and green in LE) such that the appropriate image was provided to the appropriate eye. The subject was trained over 14 sessions.

Results:

FIG. 3 depicts the change of SED as measured with the binocular rivalry tracking method. The ratio of the weak to strong eye's responses before and after the training was calculated. Vertical orientation was trained. Should the weak eye become stronger (i.e., reduced SED) after the training, its ability to dominate would be increased after the training. That is, the ratio should be higher after the training. Confirming this, FIG. 3a shows an increased predominance for seeing the disc in the trained (weak) eye. The increased predominance is due to increased frequency (FIG. 3b) and duration (FIG. 3c) of seeing the disc in the weak eye. In addition, the suppression duration of the weak eye is decreased after the training (FIG. 3d).

Example 2: Training with the Two-Dimensional Cat and Mouse Embodiment for a Subject with Fusion Ability Observer:

A female in her twenties with strong RE dominance participated in the study. Her visual acuities were 20/20 (RE) and 20/20 (LE).

Procedures:

The following tests were run to establish baselines in the foveal region before and after the training: SED, stereopsis threshold and stereopsis response time (RT). These test stimuli are shown, respectively, in FIGS. 4-5, 6 and 7 and are described above.

The cat and mouse embodiment of the present invention, as described in Example 1 above, was implemented during the training. In addition, because the subject was capable of binocular fusion, the difficulty was increased by adding weak boundary contours to the strong eye. This was done by phase-shifting selected areas of the grating in the strong eye that corresponded to the cat grating seen by the weak eye (FIG. 8). In an alternative embodiment, the phase-shifted boundary contour could be made to correspond to the mice rather than the cat, or to correspond to both the cat and mice. The phase-shifted boundary contours increased the stimulus strength of the strong eye and made it more likely for the strong eye to be dominant, which was contrary to the goal of the training. Therefore, the additional goal/challenge was for the subject to maintain dominance of the weak eye in the presence of the increased stimulus strength of the strong eye.

During each training session, multiple trials were played totaling up to 1.5 hour. The trial was scored in terms of the number of mice caught, and scores were deducted for catching the wrong mice. The images were provided on a computer screen where the images for the dominant eye and the non-dominant eye were overlaid and were each provided in either a red or green color. The subject viewed the computer screen using 3D glasses (green filter in RE and red in LE) such that the appropriate image was provided to the appropriate eye. The subject was trained over 20 sessions.

Figure 9:
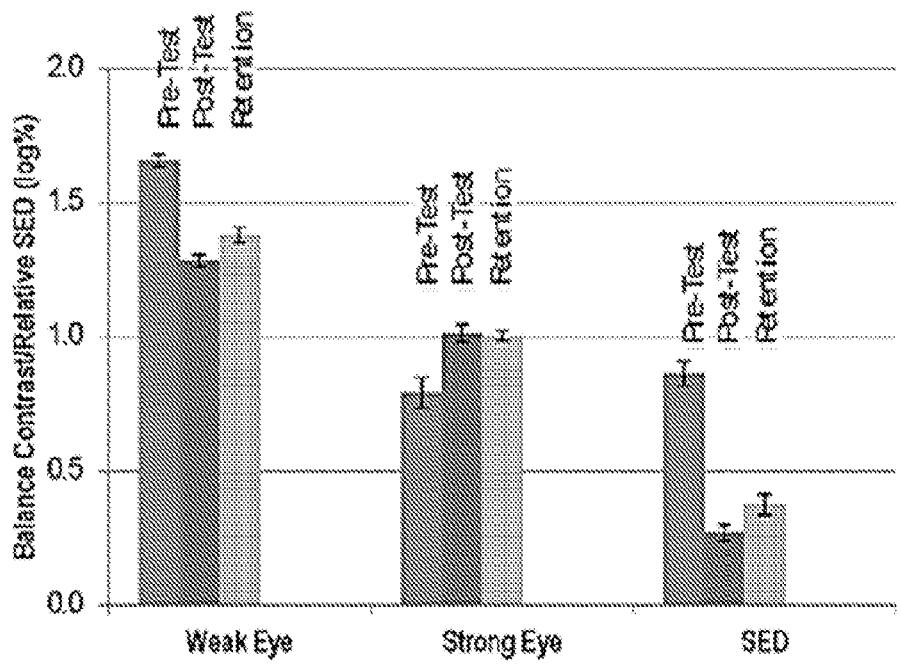
FIG. 9 demonstrates reduction in SED after training with the "cat and mouse" embodiment of the present invention. The SED remained at the reduced level when measured 2 months after the training ended. This indicates retention of the training effect.
Figure 10:
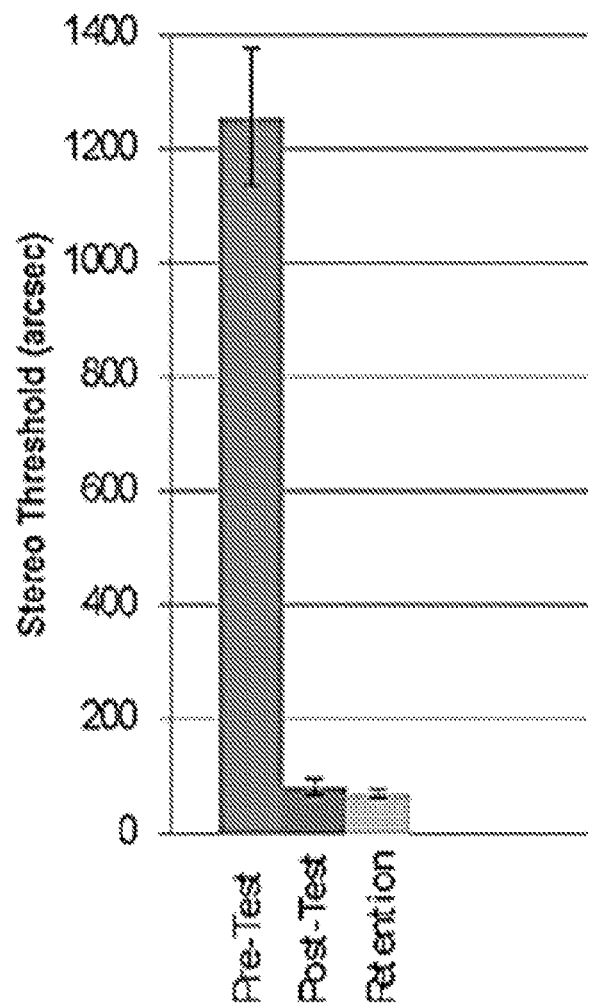
FIG. 10 demonstrates reduction in stereopsis threshold after training with the "cat and mouse" embodiment of the present invention. The threshold remained at the reduced level when measured 2 months after the training ended.
Figure 11:
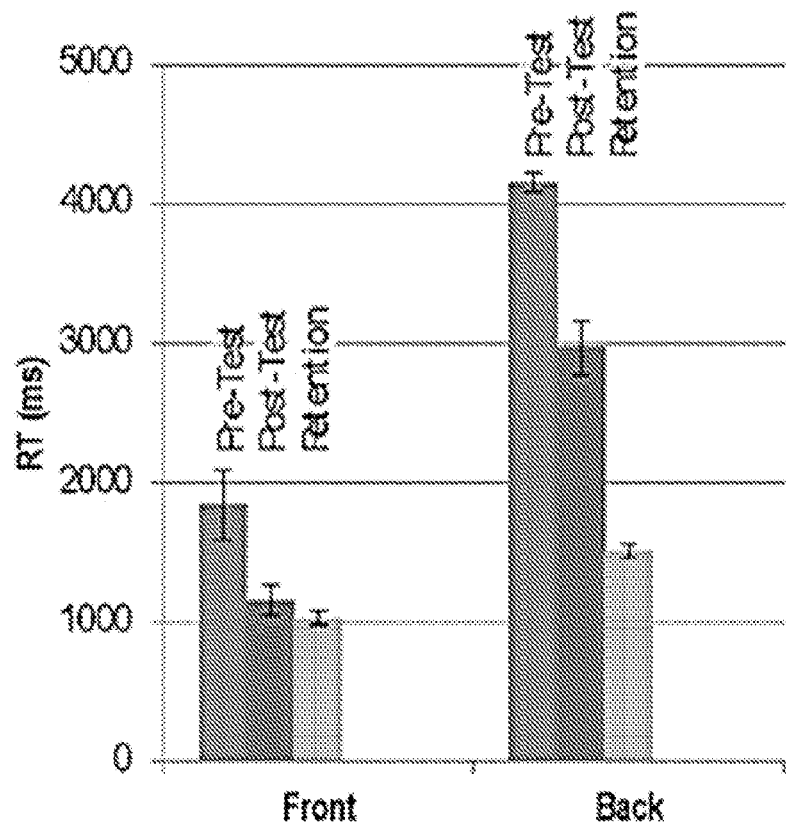
FIG. 11 demonstrates reduction in stereopsis response times after training with the "cat and mouse" embodiment of the present invention. The response times remained reduced when measured 2 months after the training ended.

Results:

Generally, the subject exhibited significant improvements in all the three measures tested. Specifically, FIG. 9 shows reduced SED after the training. This was due to a significant decrease in the weak eye's balance contrast and increased in the strong eye's balance contrast. FIGS. 10 and 11, respectively, show reduced stereopsis threshold and reduced response time to detect stereo stimuli in the back and front. All graphs also show that the improvements were retained when the subject was tested two months after the training was terminated.

Example 3: Training with the Three-Dimensional Matrix Scanning Embodiment for a Subject with Fusion Ability Observer:

A male subject in his thirties with mild RE dominance participated in the study. His visual acuities were 20/20 (RE) and 20/20 (LE).

Procedures:

The following tests were run to establish baselines in the foveal region before and after the training: SED, stereopsis threshold and stereopsis response time (RT). These test stimuli are shown, respectively, in FIGS. 4-5, 6 and 7. In addition, similar test stimuli were used to test four concentric, parafoveal retinal locations two degrees from the fovea [(2°, 0°), (2°, 90°), (2°, 180°), (2°, 270°)]. A characterization of these tests are provided above.

A series of three-dimensional matrix scanning embodiments of the present invention were implemented during the training phase. These included the following:

3-D matrix scanning whole-disc (FIG. 12). Here, small circular disc areas were phase-shifted relative to the larger vertical grating seen by the weak eye. Phase-shifting the grating leftward or rightward rendered a disc in either crossed or uncrossed binocular disparity and made it appear, respectively, as in front or behind the larger vertical grating background.

3-D matrix scanning half-disc (FIG. 13). Rather than phase-shifting the entire disc, each disc was divided into upper and lower halves. Each half disc was laterally phase-shifted relative to its counterpart in opposite directions, rendering one half-disc to be seen in front and the other half-disc to be seen behind the larger vertical background.

Figure 14:
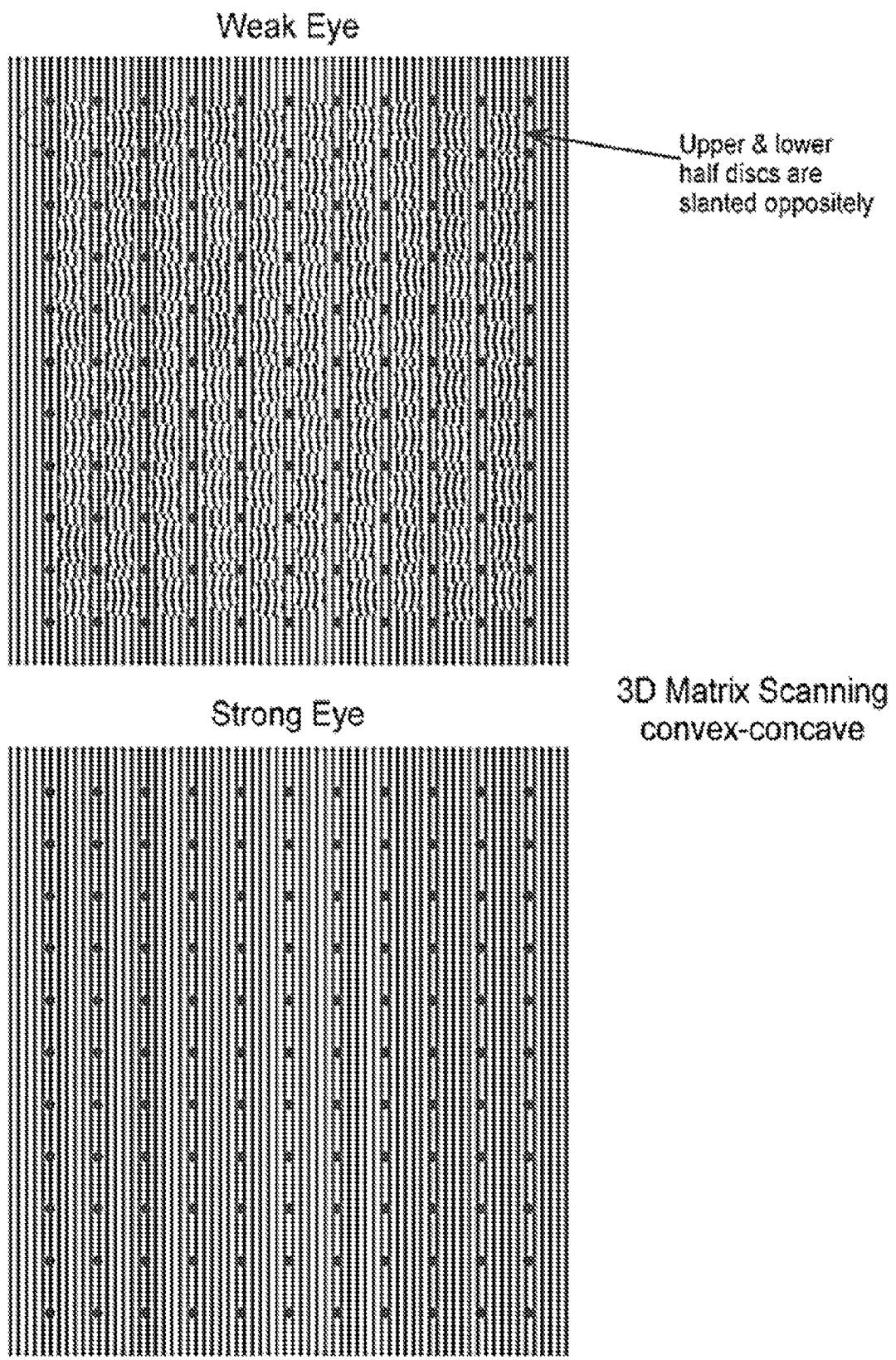
FIG. 14 provides another embodiment of a matrix of visual stimuli in accordance with the present invention. Each disc was divided into upper and lower half-discs. But instead of phase-shifting as in FIG. 13, the grating in one half-disc is slanted (rotated) up to ~15° from the vertical in an opposite direction relative to the other. Doing so created a gradient of binocular disparity rendering the entire disc to be seen either as a surface convex or concave toward the subject.

3-D matrix scanning convex-concave (FIG. 14). Each disc was divided into upper and lower half-discs. But instead of phase-shifting, the grating in one half-disc was slanted (rotated) up to ~15° from the vertical in an opposite direction relative to the other. Doing so created a gradient of binocular disparity rendering the entire disc to be seen either as a surface convex or concave toward the subject.

Figure 15:
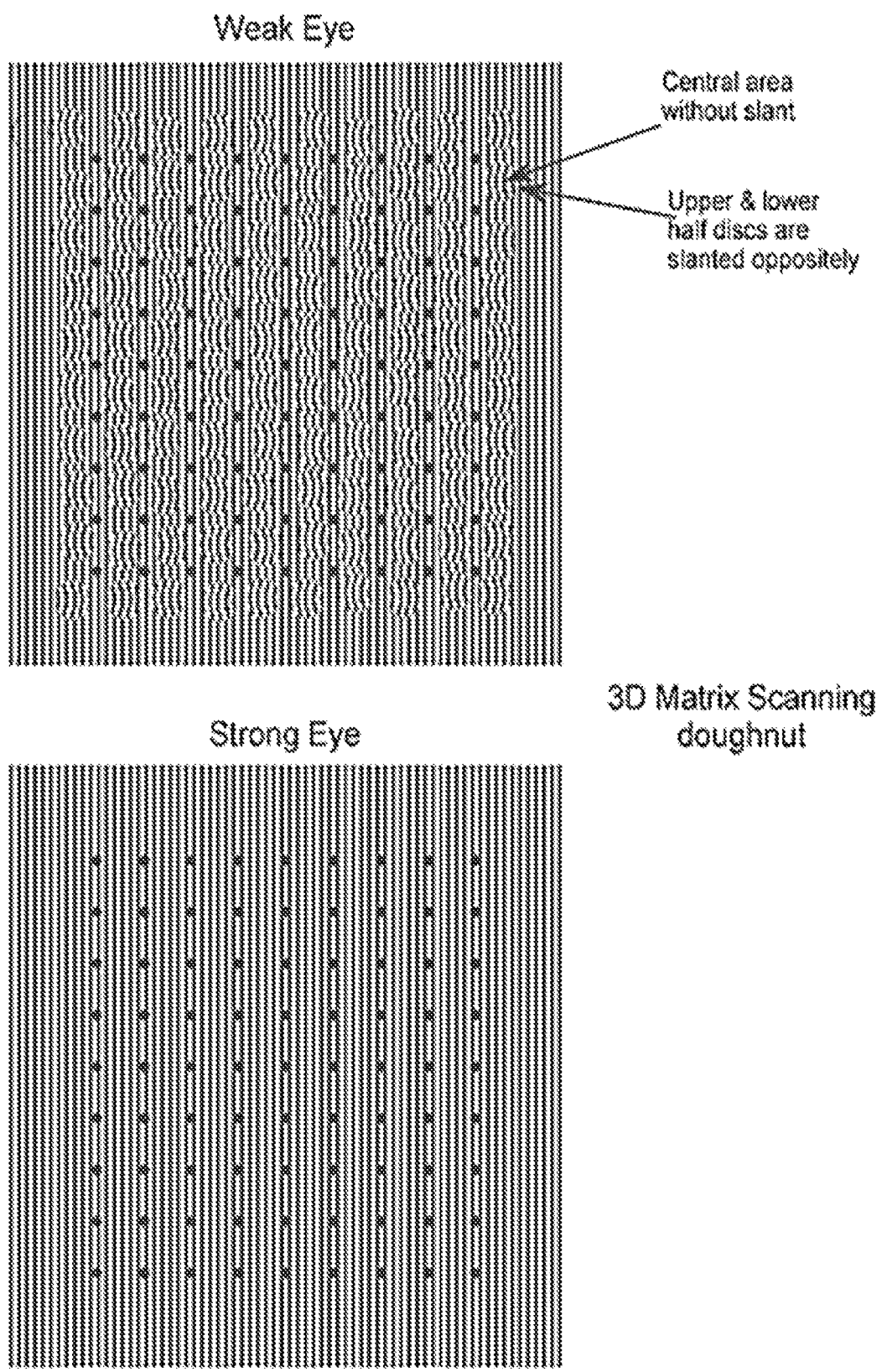
FIG. 15 provides an even further embodiment of a matrix of visual stimuli in accordance with the present invention. This embodiment is similar in construction to that in FIG. 14, except that the central circular area of the disc was removed. Doing so increased the difficulty of perceiving the 3D surface. Rather than seeing a convex or concave surface, the subject sees a doughnut-shaped 3D surface.

3-D matrix scanning doughnut (FIG. 15). The design was similar in construction to the 3D Matrix scanning convex-concave design, except that the central circular area of the disc was removed. Doing so increased the difficulty of perceiving the 3D surface. Rather than seeing a convex or concave surface, the subject saw a doughnut-shaped 3D surface.

In each of the above embodiments, the experimenter determined the number of disc targets to be presented to the subject. Typically an array of 10×10 matrix, i.e., 100 discs arranged in ten columns and rows, was used to train the subject. The subject's task was to scrutinize the entire array in a predetermined order (e.g., right-left or up-down) to search for the target. Depending on the specific embodiment, the target could be defined by a whole-disc in front, a half-disc with the lower half in front, a concave surface, or a convex doughnut. Once the target was found while scanning, a selector ring was placed over the target and an answer recorded by the computer. Each trial (game) lasted 2 minutes. Performance was scored as the total rows/columns finished, number of mistakes and time taken to finish.

The difficulty of the trial was controlled by various enhancement, or detraction, factors. These included array size, stimulus contrast, stimulus size, jitter misalignment, jitter speed, and combinations thereof. The benefit of increasing the array size, besides increasing the difficulty, was the stimulation of a larger retinal area in addition to the foveal region. This increased the efficiency of the training to reduce SED and improve stereopsis.

Similar to the cat and mouse embodiment, the three-dimension matrix scanning game series also have secondary visual benefits since the act of playing the games required the subject to acquire the skills of depth discrimination, attention scanning, saccadic eye movement, eye-hand coordination, quick visual and motor responses, and ability to overcome visual crowding.

During each training session, multiple trials of the game were played totaling up to 1.5 hour. The game was scored in terms of the number of targets identified and time to complete the matrix. The images were provided on a computer screen where the images for the dominant eye and the non-dominant eye were overlaid and were each provided in either a red or green color. The subject viewed the computer screen using 3D glasses (green filter in RE and red in LE) such that the appropriate image was provided to the appropriate eye. The subject was trained over 19 sessions.

Figure 16A:
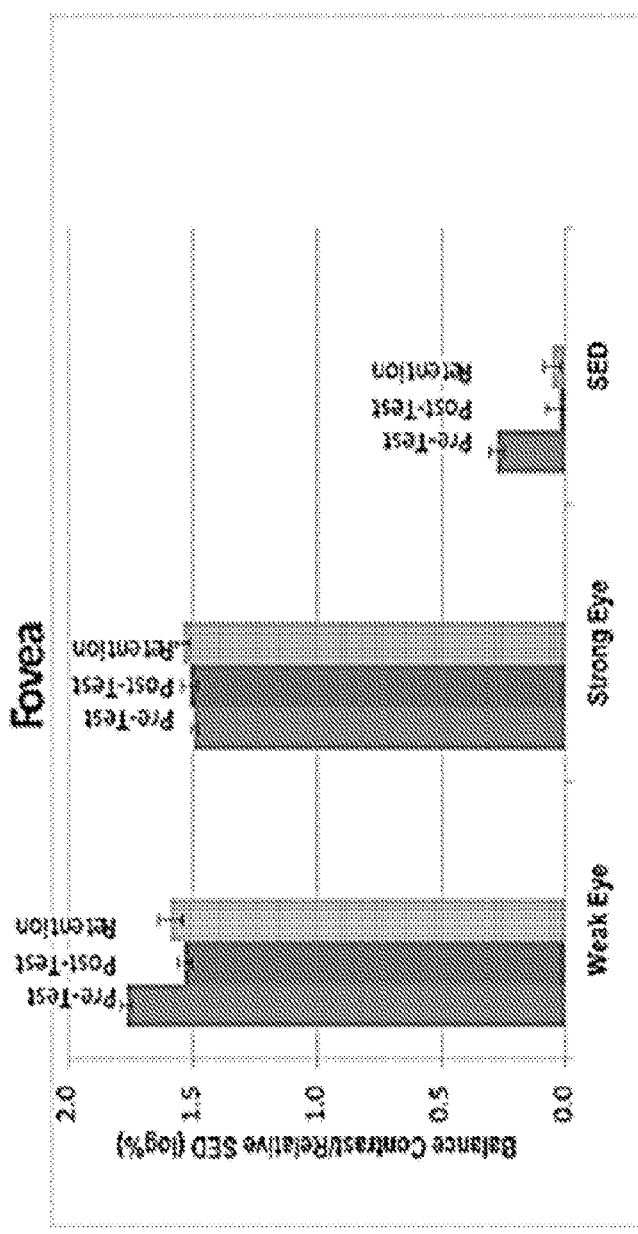
FIG. 16 demonstrates reduction of SED where (a) shows that the foveal SED and balance contrast of the weak eye is significantly reduced after the training; and (b) shows the overall averaged SED from the fovea and four parafoveal locations tested is significantly reduced after the training. The learning effect of SED is retained four months after the training ended.
Figure 16B:
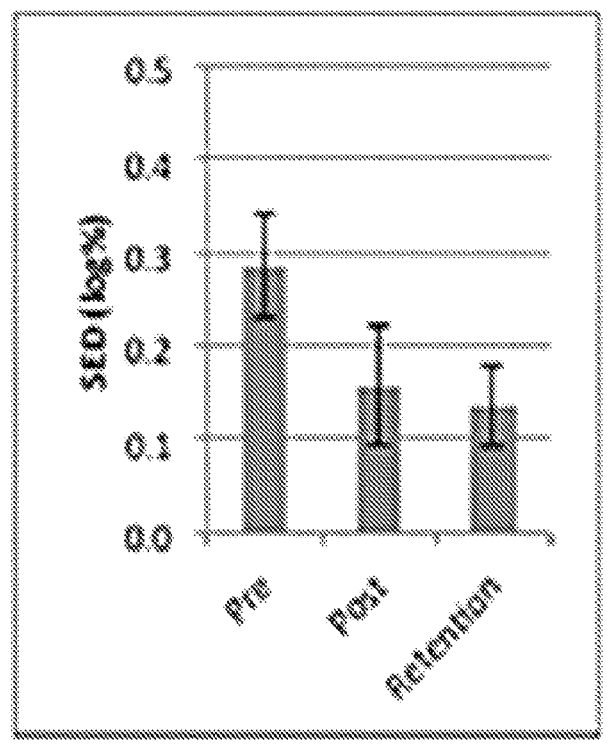
Figure 17A:
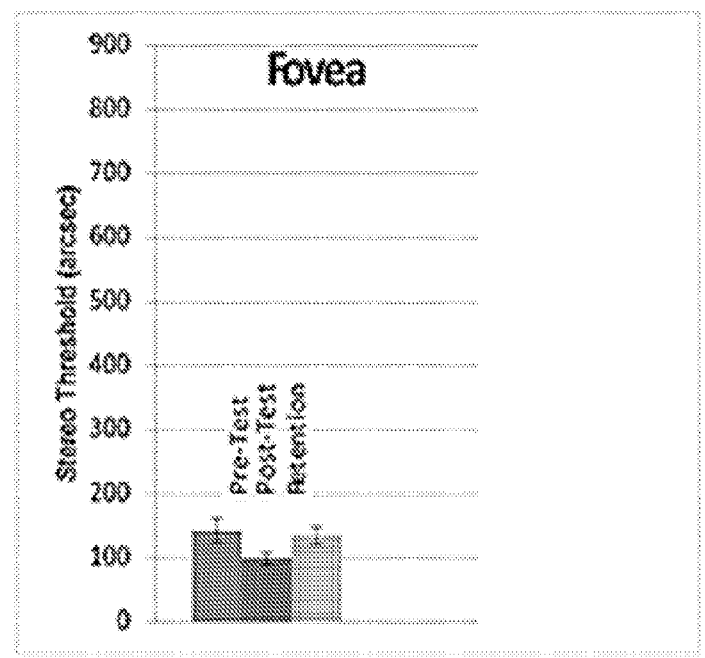
FIG. 17 demonstrates reduction of stereopsis threshold where (a) shows a marginally significant reduction in stereo threshold in the fovea after the training; and (b) shows a marginally significant improvement in averaged stereo threshold from the fovea and four parafoveal locations tested after the training.
Figure 17B:
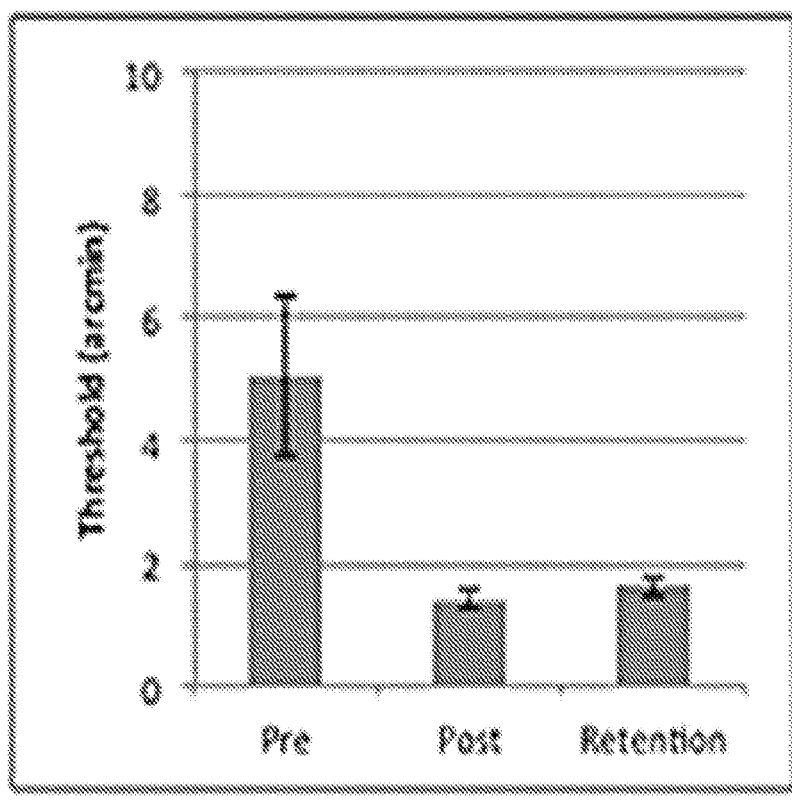
Figure 18:
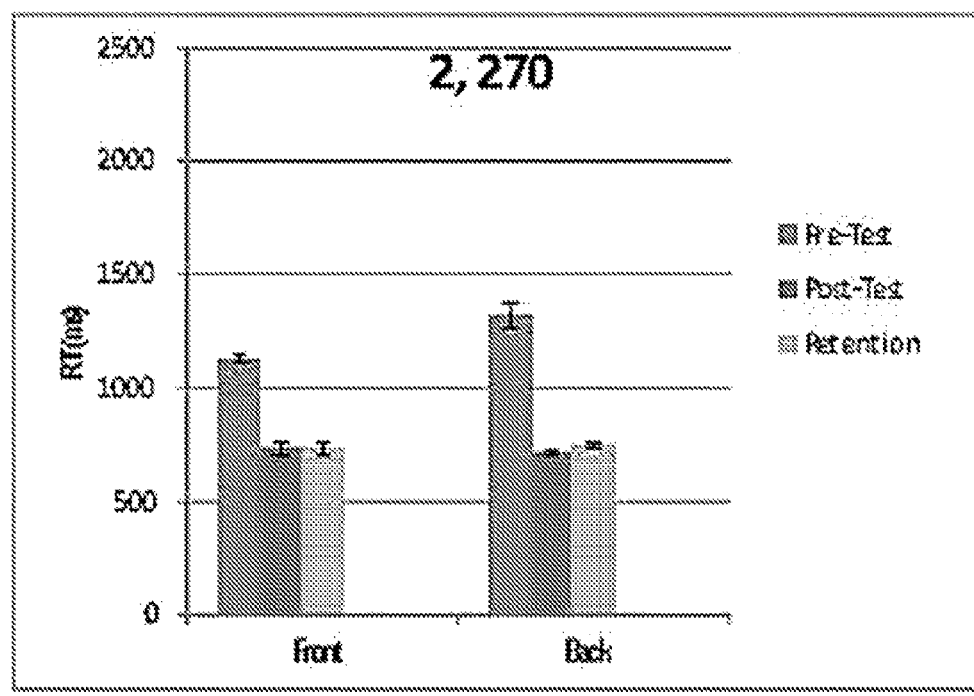
FIG. 18 demonstrates the improvement in response time to detect a stimulus in the front and back depths. Significant reduction in response time is found in all locations tested, in the fovea (center graph) and the four parafoveal locations (surrounding graphs). The improvement is retained four months after the training ended.

Results:

Generally, the subject exhibited improvements in all the three measures tested both centrally in the fovea and in the parafoveal locations. The improvements of visual functions are generally retained (long lasting) after the training ended. Specifically, FIG. 16 shows significantly reduced SED after the training, and the effect is evident four months after the training ended. FIGS. 17 and 18, respectively, show marginally significant reduced stereopsis threshold and significantly reduced response time to detect stereo stimuli in the back and front, which are generally retained four months later. These findings demonstrate that besides treating subjects with amblyopia and strong SED, the invention can be used to enhance vision of subjects with smaller SED (before the treatment). SED is further reduced after treatment with concordant long-lasting improvements in stereo perception.

Example 4: Other Embodiments of the Push-Pull Paradigm

Figure 20:
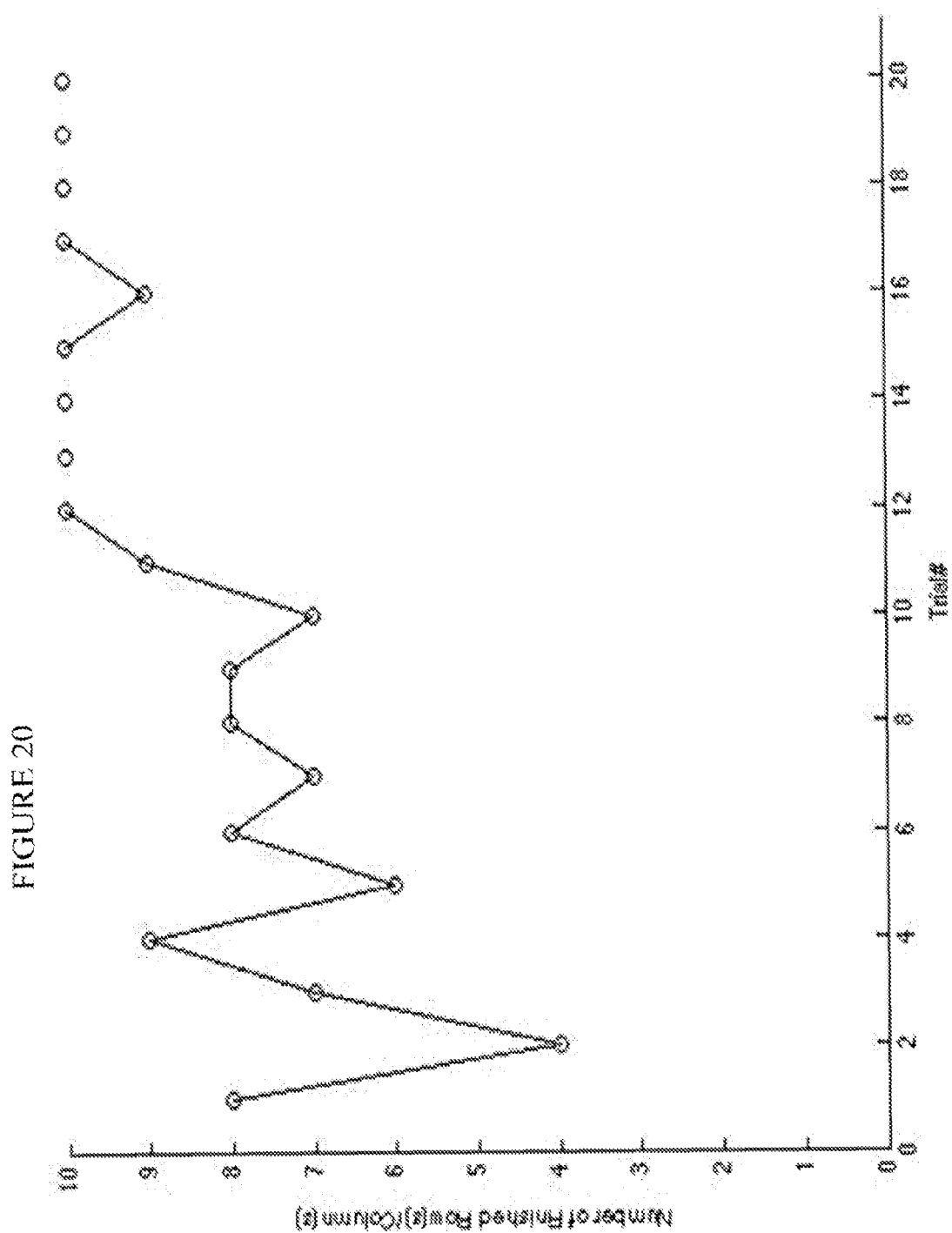
FIG. 20 illustrates representative data showing the performance of a subject trained on the embodiment of FIG. 19. This embodiment had 10×10 matrix and the subject had to scan each row from top to bottom over a 2 minute viewing duration. Graph (a) shows the number of rows finished in each trial over twenty trials, graph (b) the number of errors made in selecting the target, and graph (c) the real or extrapolated time taken to finish the array. Because the duration was 2 minute, only data points below 2 minutes reflect the real time. Extrapolated time is the predicted time it would have taken the subject to finish the entire array. The general trend in all three graphs is that the number of rows finished increases, the errors made decrease, and time taken to finish decreases, as the number of trials (games played) increases. In other words, the subject became more proficient with training.
Figure 20:
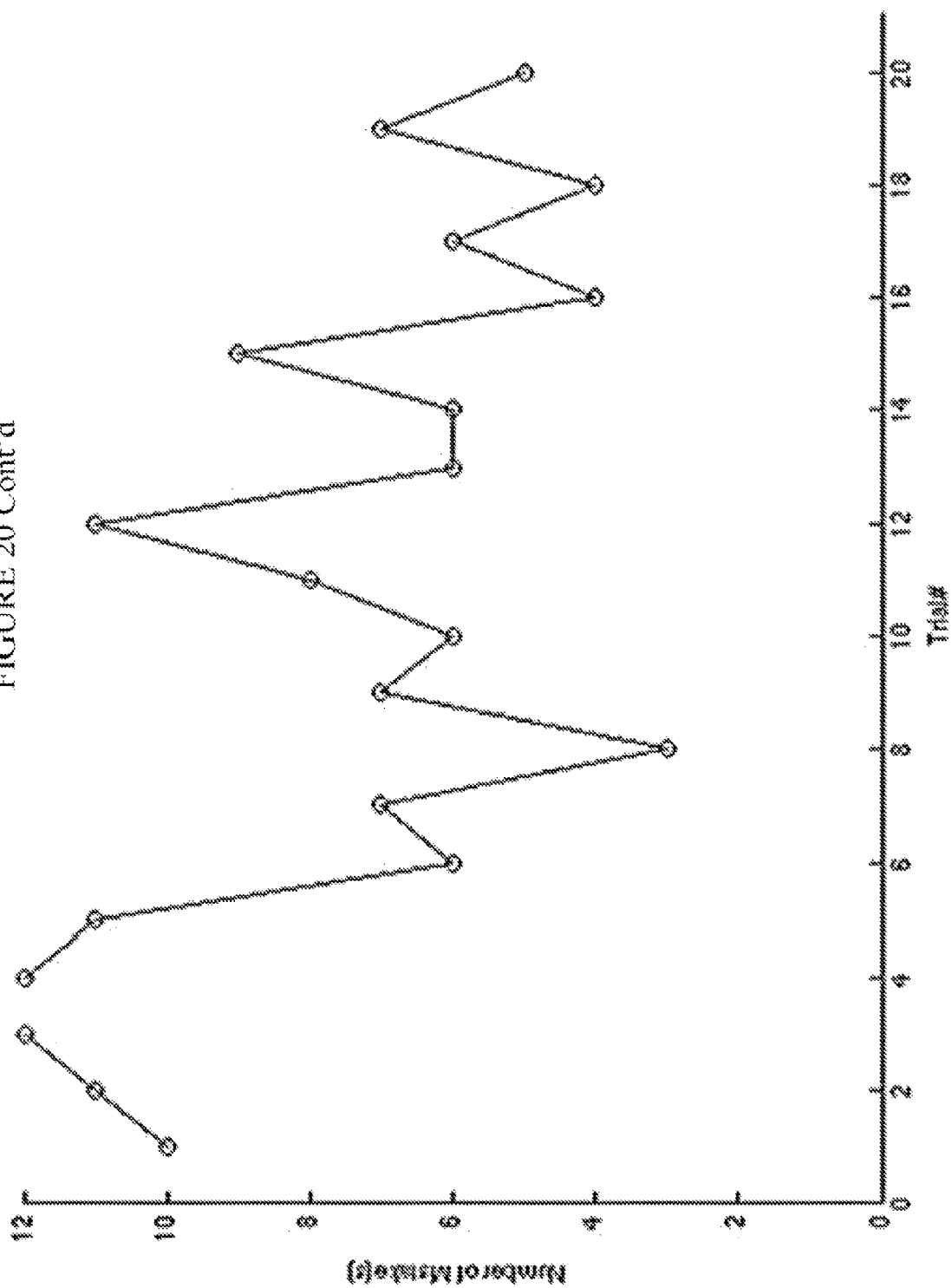
Figure 20:
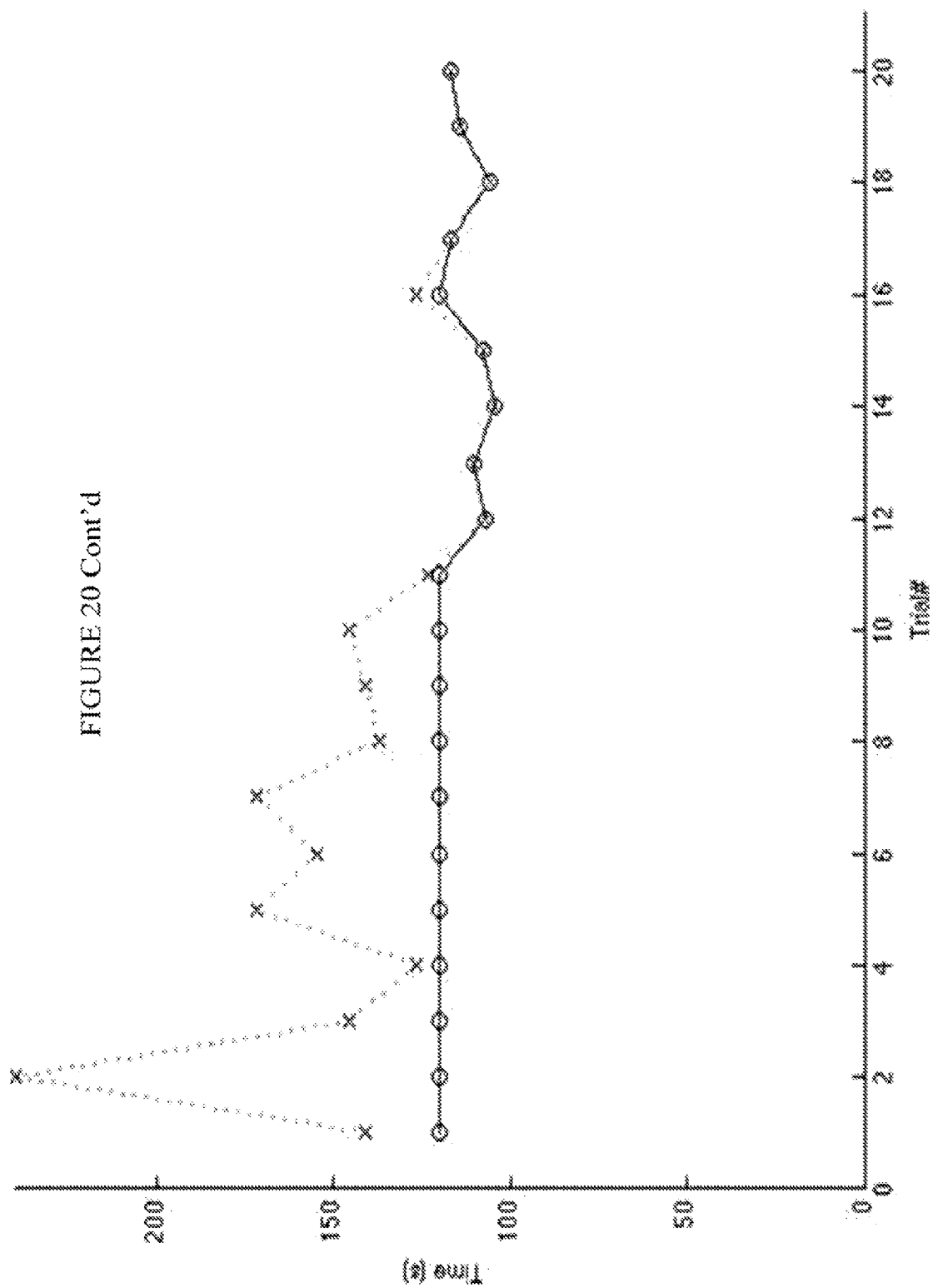

Besides the two-dimension cat and mouse embodiments of Examples 1 and 2 and the matrix scanning of Example 3, the push-pull principle was adapted into three other embodiments, as follows:

2-D matrix scanning (FIG. 19). The embodiment design is similar to the three-dimensional matrix scanning embodiment of Example 3 except that instead of manipulating binocular disparity (phase-shift and slant), the disc orientation is manipulated. The subject's task is to select the target disc with a specific orientation (e.g., 90° from among 85° and 95° discs). Other aspects of the game design are similar to the two-dimensional cat and mouse design, i.e., orthogonal grating orientations, and using similar enhancement factors. FIG. 20 shows a sample performance of a subject trained on this game, with improvements occurring as the game play progresses.

Figure 22:
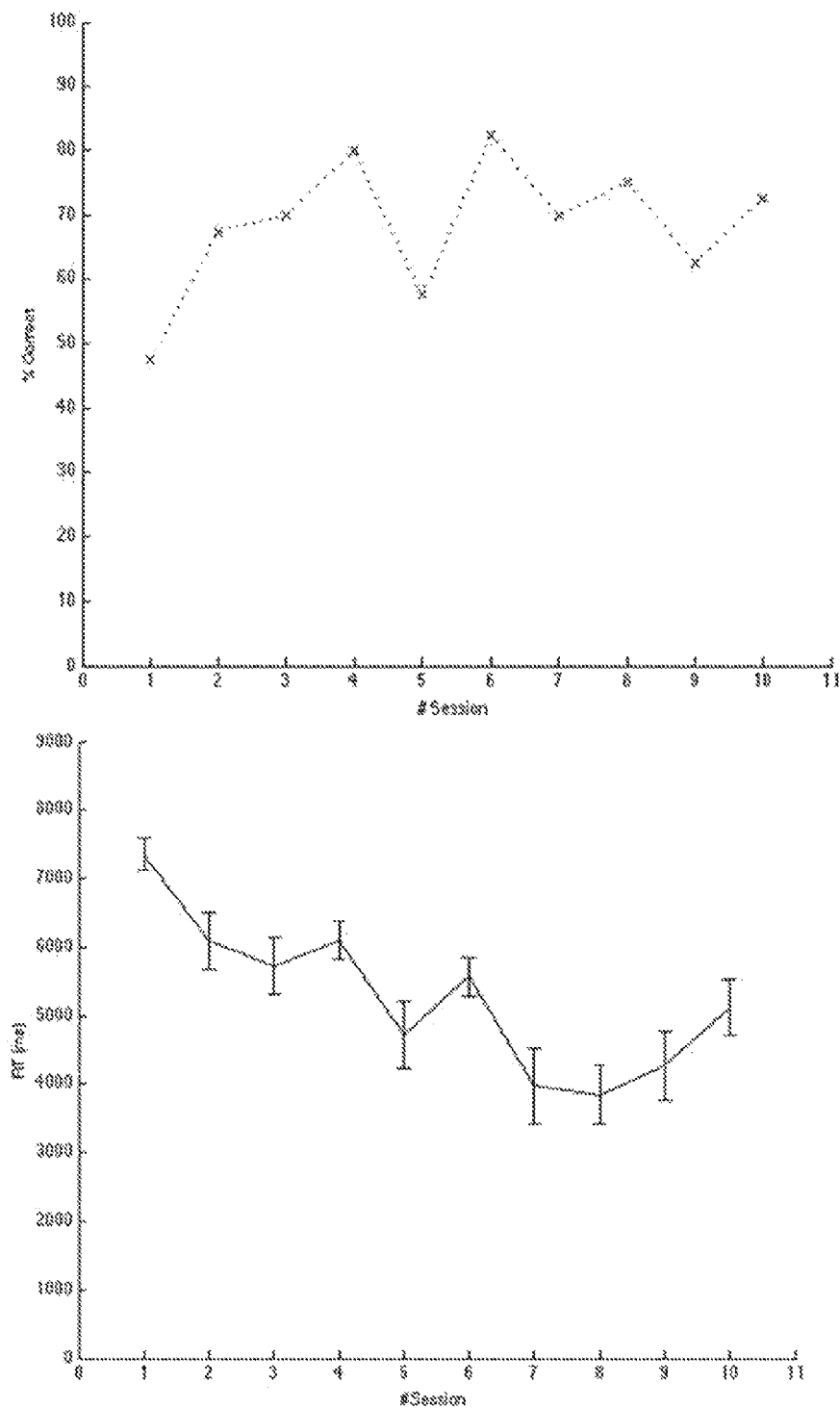
FIG. 22 provides representative data showing the performance of a subject trained on the embodiment of FIG. 21. Graph (a) plots the percentage correct in responding to either target present or absent and graph (b) plots the time taken to respond. The general trend in both graphs shows that as training progressed over multiple sessions, the correct responses increase while the time to response decreases. This indicates the subject became more proficient with training.

2D response time (RT) scanning (FIG. 21). This embodiment is similar to that of the 2D matrix scanning of FIG. 19, with two exceptions. One, the array of targets is smaller, e.g., 5×5 rather than the typical 10×10. Two, an array could have one or more target discs, or no target disc at all. This is because the goal for the subject is to visually search, within a limited window of viewing duration (e.g., 2-10 seconds), whether the target(s) is (are) present or absent. The speed of search is recorded as the response time (RT). In this example, the stimulus seen by the strong eye's half-image has some boundary contours (detraction factor) to further challenge the weak eye to remain dominant. FIG. 22 shows a sample performance of a subject trained on this game, with improvements occurring as the game play progresses.

Figure 24A:
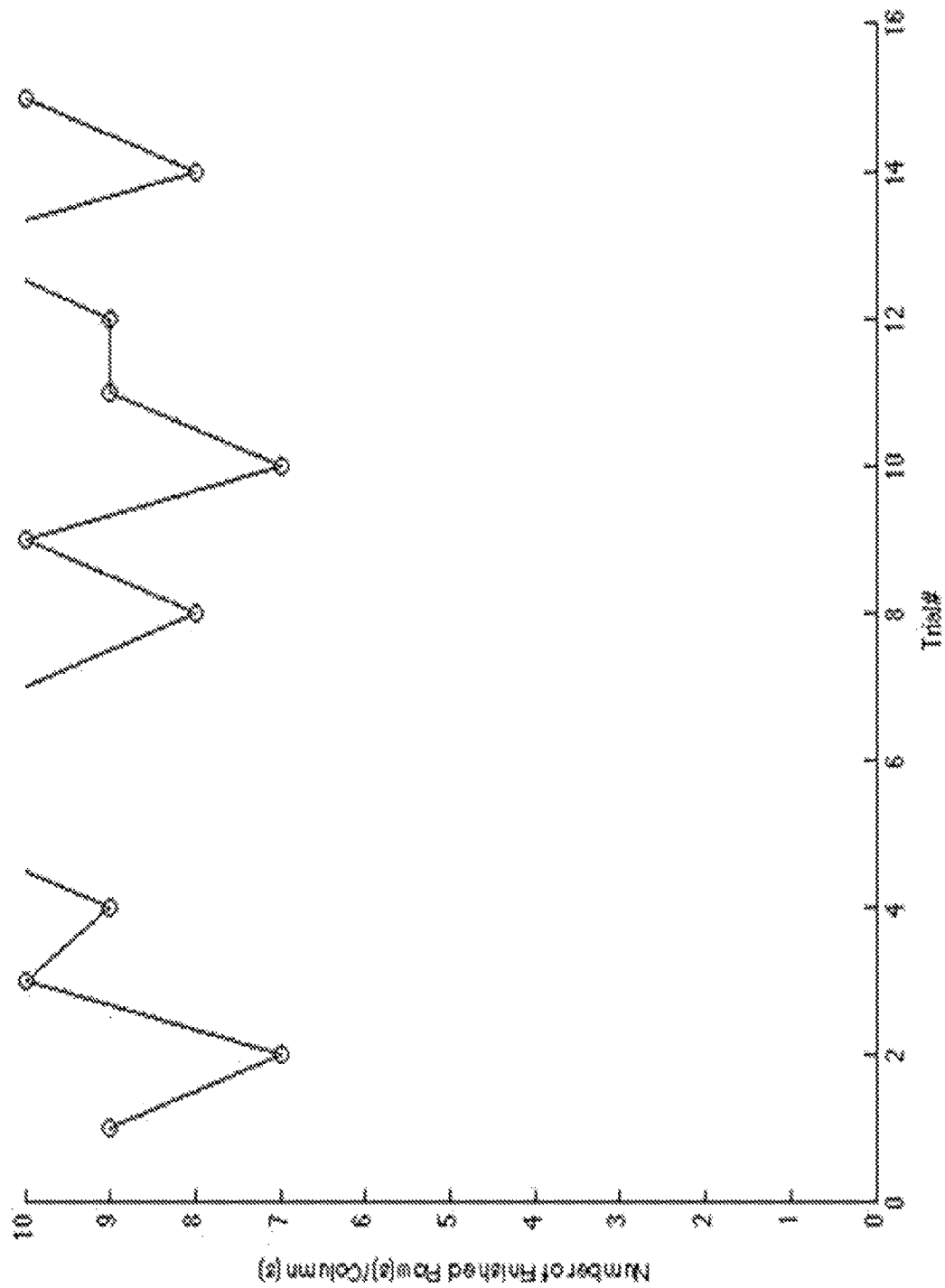
FIG. 24 provides data showing the performance of a subject trained on the embodiment of FIG. 23. Graph (a) shows the number of rows finished per 2-minute trial, graph (b) the number of mistakes and misses in selecting the target, and graph (c) the real or extrapolated time taken to finish the array. The general trend in all three graphs was cyclical and did not vary by much over the 15 trials performed, indicating a plateau performance over the fifteen trials.
Figure 24C:
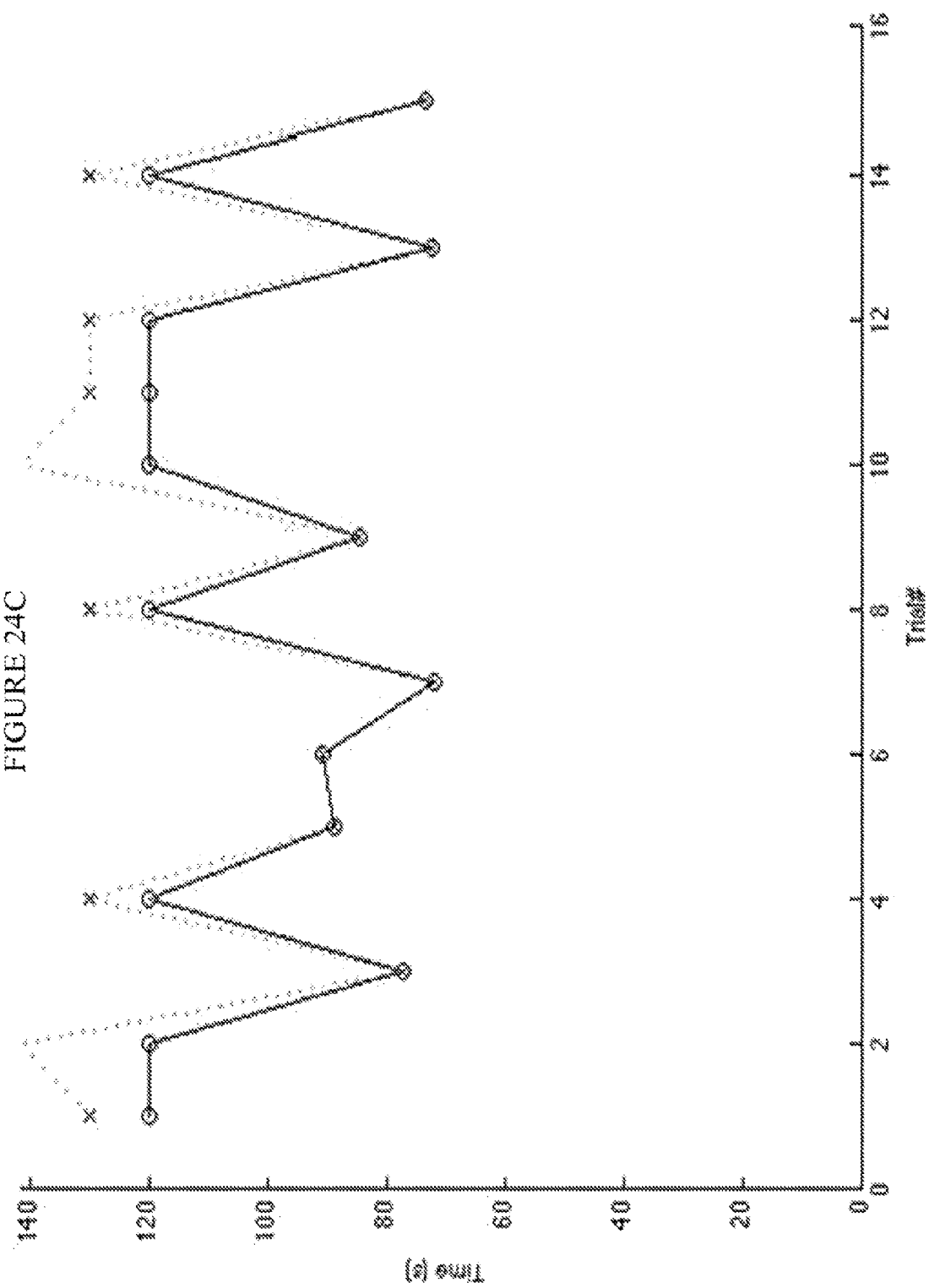

2D matrix scanning from memory (FIG. 23). This embodiments is similar to the two-dimensional matrix scanning game of FIG. 19, except that each game (trial) is preceded by a specific sequence of targets to memorize. During the game, the subject has to select the targets based on the memorized sequence. FIG. 24 shows a sample performance of a subject trained on this game, with improvements occurring as the game play progresses.

The difficulty of the games above can be controlled by various enhancement, or detraction, factors. These include array size, stimulus contrast, stimulus size, boundary contour (ring), ring thickness, flashing ring, jitter misalignment and jitter speed. In addition, "bites" (small breaks) can be added to the discs and require the subject to search for discs with particular orientation in conjunction with a specific bite location.

Results:

The samples in FIGS. 20, 22 and 24 allowed the experimenter to monitor the progress of the subject during the training. Typically, the stimulus parameters of the game are selected to be challenging for the subject at the beginning of each game. It is expected, as shown in the general trends of the graphs in FIGS. 20 and 22, that the subject improves over the course of the training. If the subject no longer improves, as shown by the rather plateaued graphs in FIG. 24, new stimulus parameters will be selected to again challenge the subject.

Example 5: Further Embodiments of the Push-Pull-Plus-Stereo Paradigm

Besides the three-dimensional matrix scanning embodiments in Example 3, the Push-Pull-Plus-Stereo principle is adapted into other embodiments using a combination of the embodiments above. Three such major embodiments include:

- 3-D cat and mouse (FIG. 25). The cat and target mouse are phase-shifted relative to the vertical grating background so that they are perceived in a certain depth (front or back). The distracting mice are phase-shifted to be in the opposite depth (back or front). In certain alternative embodiments, instead of phase-shifting, the cat and mice disc gratings can also be slanted to create convex and concave surface appearance.
- 3-D matrix scanning from memory. Similar to the two-dimensional matrix scanning from Memory embodiment above, the matrix can be rendered in three-dimensions and the subject is required to select the targets according to the memorized sequence. The embodiment can be conducted using the whole discs illustrated in FIG. 26. Alternatively, other types of three-dimensional targets can be used, such as half-discs, convex-concave, and doughnut-shaped targets.
- 3-D response time (RT) scanning. This embodiment is similar to the two-dimensional response time (RT) scanning counterpart above, except that the matrix is rendered in stereo depth using three-dimensional targets, such as half-discs, convex-concave, and doughnut-shaped targets (figures not shown). The 3D targets can be variously designed, such as using half-discs, convex-concave, and doughnut-shaped targets.

Results:

The expected results are similar to those shown in FIGS. 20, 22, and 24 (for other embodiments of the training game design). The stimulus parameters used for the games are varied as soon as the subject's data plateau in order to increase the challenge of the game.

Example 6: Training with the 2D Matrix Video Game Series for Subjects with Fusion Ability Observers:

Three subjects in their twenties trained on the Matrix games. Subject A had strabismus with visual acuities of RE=20/25 and LE=20/20. Subject B had mixed anisometropia and strabismus with visual acuities of RE=20/63 and LE=20/16. Subject C was a non-amblyope with significant SED and 20/16 visual acuity in each eye.

Procedures:

Before and after the training, SED was measured using the binocular rivalry tracking method for subjects A and B (stimulus similar to FIG. 1) and the balance contrast method (stimulus similar to FIGS. 4 and 5) for subject C. Stereopsis threshold and stereopsis response time (RT) were also measured for all subjects using stimuli similar to those in FIGS. 6 and 7. Visual acuity in each eye was measured with a logMAR eye chart. Subject A was trained for 30 sessions, Subject B for 25 sessions and Subject C for 10 sessions. The lengthened training durations for Subjects A and B were due to their larger SED due to amblyopia. All three subjects were trained on the 2-D matrix scanning (FIG. 19), 2D response time (RT) scanning (FIG. 21) and the 2D matrix scanning from memory video game stimuli (FIG. 23) (see Example 4 for detailed descriptions).

Figure 29:
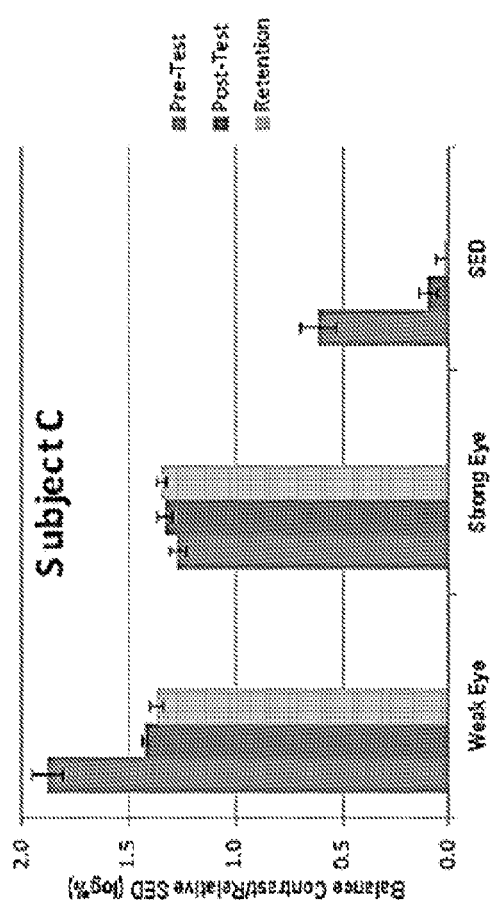
FIG. 29 demonstrates reduction of SED and balance contrast of the weak eye in subject C after the training.
Figure 30A:
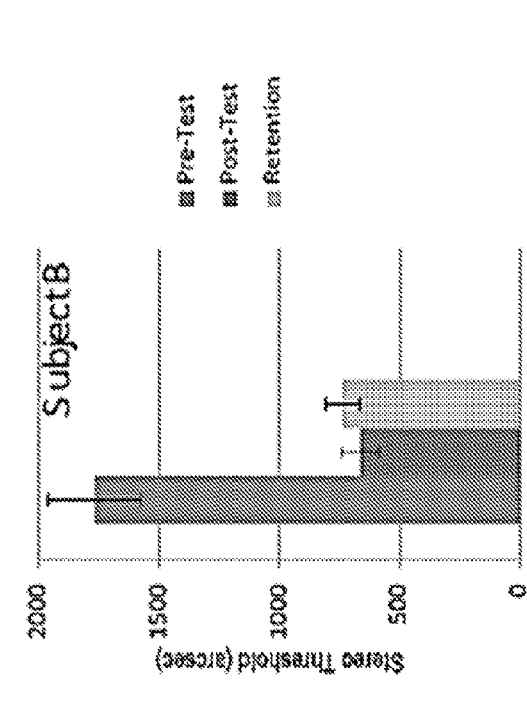
FIGS. 30 A-C demonstrate reduction and retention of stereopsis thresholds after the training, respectively, for subjects A, B and C.
Figure 30B:
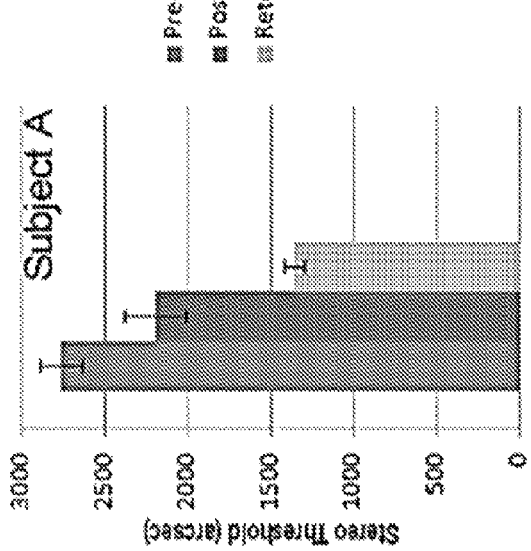
Figure 30C:
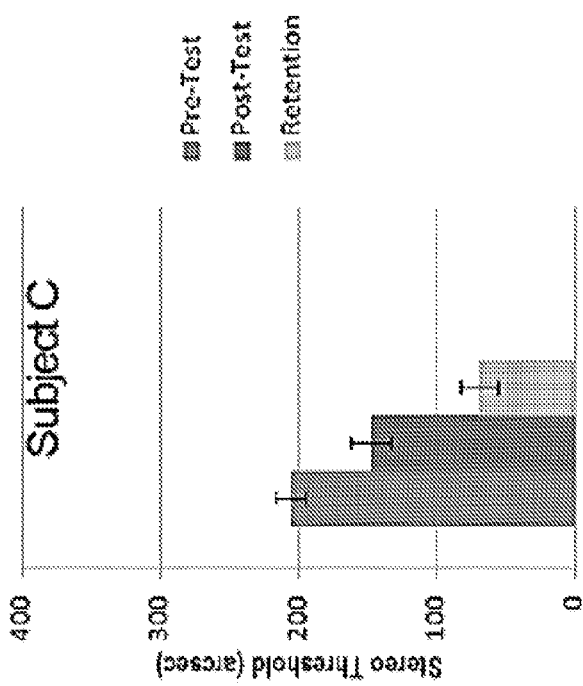
Figure 31A:
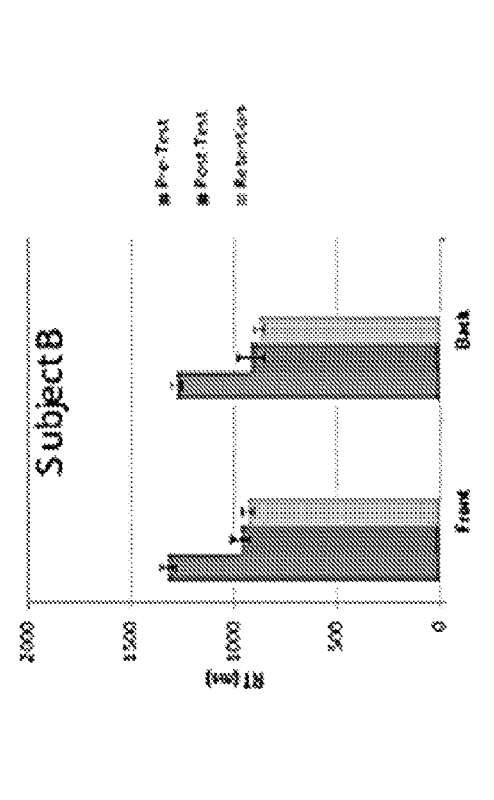
FIGS. 31 A-C demonstrate reduction and retention of stereopsis response times after the training, respectively, for subjects A, B and C.
Figure 31B:
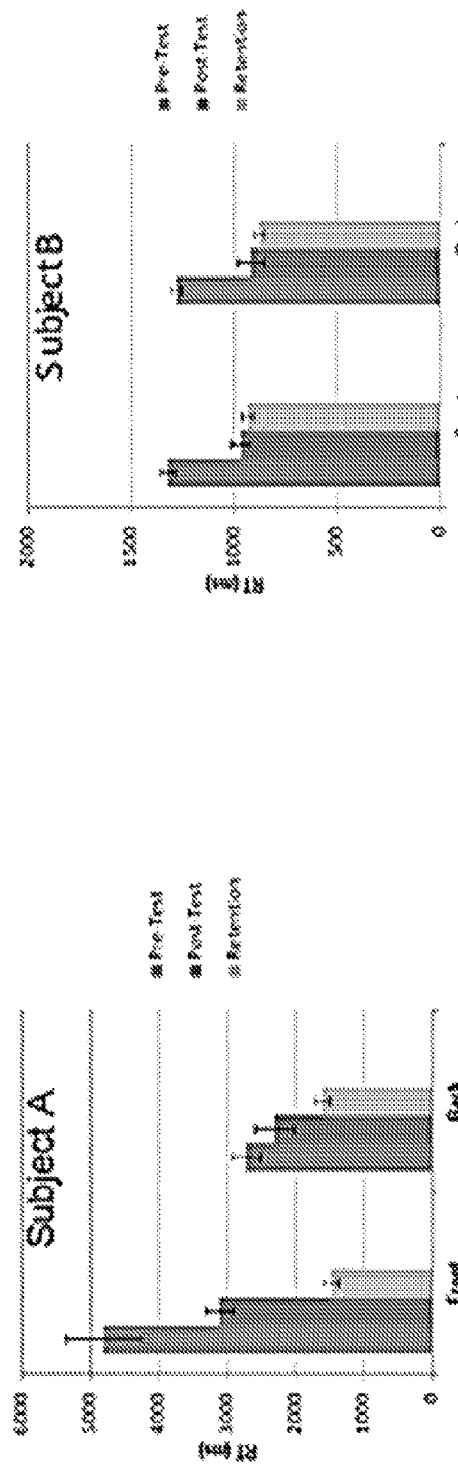
Figure 31C:
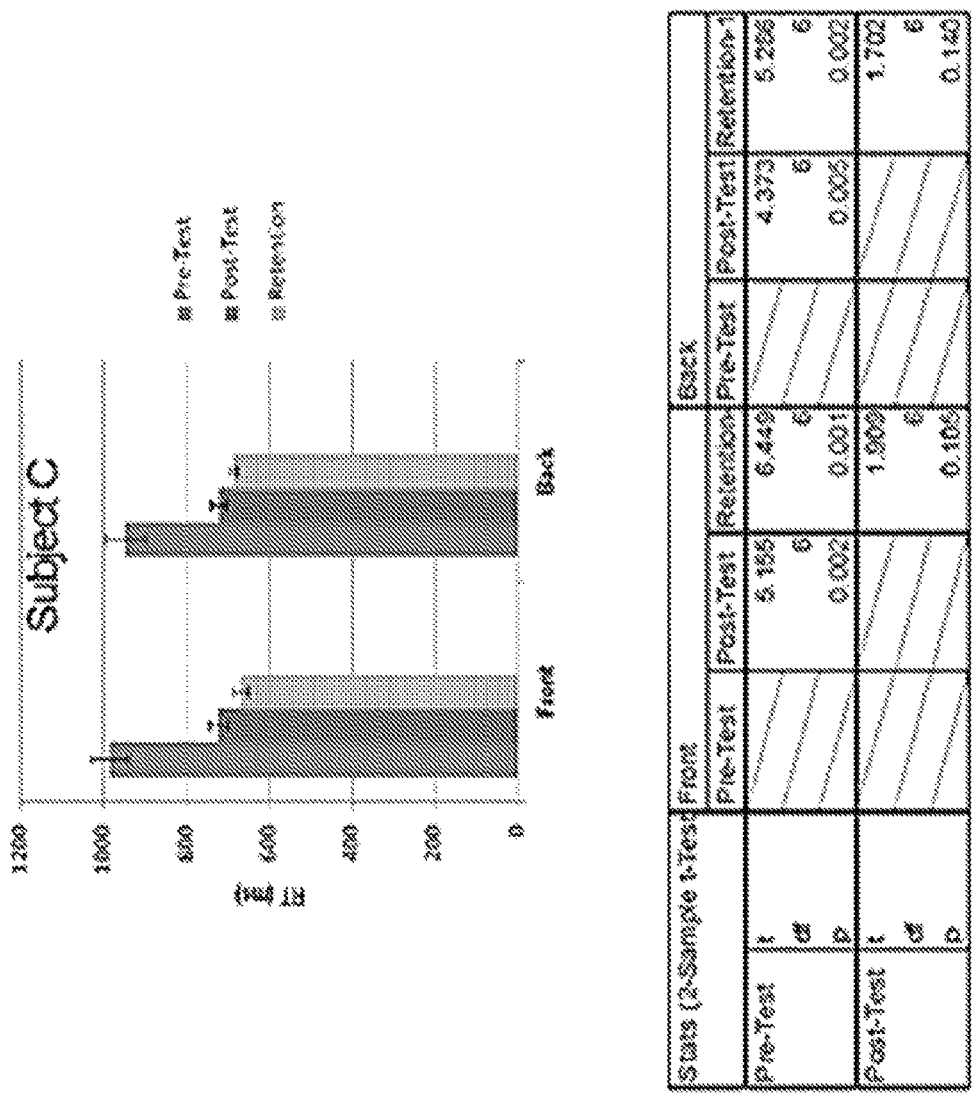

Results:

Post-training testing reveals improved strength of the weak eye. This is evidenced by an increased predominance ratio of the weak eye to strong eye for subjects A and B (FIG. 27) and lengthened dominance duration of the weak eye (FIG. 28). For subject C, this is evidenced by a reduced balance contrast of the weak eye and reduced SED (FIG. 29). All three subjects exhibited reduced stereo thresholds (FIG. 30) and shortened stereo response time (FIG. 31) after training. Furthermore, these improvements in eye balance and stereopsis were retained when the subjects were re-tested again several months after formal training ended (6 months for subject A, 5 months for subject B and 5 months for subject C.)

In addition, we found the amblyopic eye's visual acuity for subjects A and B improved to 20/20 and 20/50, respectively, i.e., a 1 line improvement of visual acuity. This finding indicates that the training protocol not only rebalances the interocular inhibition to reduce SED, but also improves monocular vision of the amblyopic eye. There was no change in visual acuities in subject C, as expected since she was not amblyopic.

What is claimed is:

1. A system for reducing sensory eye dominance or amblyopia, comprising:
   a processor;
   a display screen;
   a controller configured to receive a user action; and
   a non-transitory storage medium configured to store a computer program comprising instructions that, when executed, cause the processor to:
      cause the display screen to render, for a dominant eye of a subject, a first grating background oriented at a first angle with respect to the display screen,
      cause the display screen to render, for a non-dominant eye of the subject, a second grating background oriented at a second angle with respect to the display screen and one or more moving visual stimuli overlaid on the second grating background, wherein each of the one or more moving visual stimuli overlaid on the second grating background comprises a contour line having a thickness, a grating having a contrast, a phase and a grating orientation, and defines a speed of movement, instruct the subject to identify the one or more moving visual stimuli overlaid on the second grating background, cause the controller to receive one or more user actions responsive to identifying the one or more moving visual stimuli overlaid on the second grating background, measure a reaction time based on when a visual stimulus is rendered on the display screen and when a user action responsive to identifying the visual stimulus is received by the controller, calculate a score based on the one or more user actions and the reaction time, and adjust a level of difficulties for the subject based on the calculated score by causing the display screen to flash on/off the contour line or change the thickness of the contour line of the one or more moving visual stimuli overlaid on the second grating background.

2. The system of claim 1, wherein the computer program further comprises instructions that, when executed, cause the display screen to render one or more visual stimuli overlaid on the first grating background.

3. The system of claim 1, wherein the first and second grating backgrounds are the same.

4. The system of claim 1, wherein the orientation of the grating of the one or more moving visual stimuli overlaid on the second grating background is substantially orthogonal to the second angle.

5. The system of claim 1, wherein the computer program further comprises instructions that, when executed, cause the display screen to render the one or more moving visual stimuli in a cat-and-mouse game.

6. The system of claim 1, wherein the instructions for adjusting the level of difficulties will cause the display screen to change the contrast or the grating orientation of the grating of the one or more moving visual stimuli overlaid on the second grating background, or to change the speed of movement of the one or more moving visual stimuli overlaid on the second grating background.

7. The system of claim 5, wherein the computer program further comprises instructions that, when executed, cause the processor to test reliability of the subject by causing the display screen to momentarily overlay an additional grating onto the grating of the one or more moving visual stimuli overlaid on the second grating background, and wherein the additional grating is oriented orthogonal to the grating of the one or more moving visual stimuli overlaid on the second grating background.

8. The system of claim 1, wherein the display screen is configured to render the first grating background at a first portion of the display screen, and render the second grating background and the one or more moving visual stimuli overlaid thereon at a second portion of the display screen so that the dominant eye of the subject sees only the first grating background and the non-dominant eye of the subject sees only the second grating background and the one or more moving visual stimuli overlaid thereon.

9. The system of claim 1, further comprising a pair of 3D glasses configured to filter a first color in a first lens and filter a second color in a second lens, wherein the display screen is configured to render the first grating background in the first color, and render the second grating background and the one or more moving visual stimuli overlaid thereon in the second color so that when the subject wears the 3D glasses the dominant eye of the subject sees only the first grating background and the non-dominant eye of the subject sees only the second grating background and the one or more moving visual stimuli overlaid thereon.

10. The system of claim 9, wherein the orientation of the grating of the one or more moving visual stimuli overlaid on the second grating background is substantially the same as the second angle, and the phase of the grating of the one or more moving visual stimuli overlaid on the second grating background is a phase shift relative to the second grating background.

11. A method for reducing sensory eye dominance or amblyopia, comprising:
rendering, by a display screen, for a dominant eye of a subject, a first grating background, wherein the first grating background is oriented at a first angle with respect to the display screen;
rendering, by the display screen, for a non-dominant eye of the subject, a second grating background and one or more moving visual stimuli overlaid on the second grating background, wherein the second grating background is oriented at a second angle with respect to the display screen, and wherein each of the one or more moving visual stimuli overlaid on the second grating background comprises a contour line having a thickness, a grating having a contrast, a phase and a grating orientation, and defines a speed of movement;
instructing, by a processor, the subject to identify the one or more moving visual stimuli overlaid on the second grating background;
receiving, by a controller, one or more user actions responsive to identifying the one or more moving visual stimuli overlaid on the second grating background;
measuring, by the processor, a reaction time based on when a visual stimulus is rendered on the display screen and when a user action responsive to identifying the visual stimulus is received;
calculating, by the processor, a score based on the one or more user actions and the reaction time; and
adjusting, by the processor, a level of difficulties for the subject based on the calculated score by flashing on/off the contour line or changing the thickness of the contour line of the one or more moving visual stimuli overlaid on the second grating background.

12. The method of claim 11, further comprising rendering, by the display screen, one or more visual stimuli overlaid on the first grating background.

13. The method of claim 11, wherein the first and second grating backgrounds are substantially same.

14. The method of claim 11, wherein the grating orientation of the grating of the one or more moving visual stimuli overlaid on the second grating background is substantially orthogonal to the second angle.

15. The method of claim 11, further comprising rendering, by the display screen, the one or more moving visual stimuli in a cat-and-mouse game.

16. The method of claim 11, wherein adjusting the level of difficulties for the subject comprises changing the contrast or grating orientation of the one or more moving visual stimuli overlaid on the second grating background, or changing the speed of movement of the one or more moving visual stimuli overlaid on the second grating background.

17. The method of claim 15, further comprising, by the processor, testing reliability of the subject by causing the display screen to momentarily overlay, on the display screen, an additional grating onto the grating of the one or more moving visual stimuli overlaid on the second grating background, wherein the additional grating is oriented orthogonal to the grating of the one or more moving visual stimuli overlaid on the second grating background.

18. The method of claim 11, further comprising rendering, by the display screen, the first grating background at a first portion of the display screen, and rendering the second grating background and the one or more moving visual stimuli overlaid thereon at a second portion of the display screen so that the dominant eye of the subject sees only the first grating and the non-dominant eye of the subject sees only the second grating background and the one or more moving visual stimuli overlaid thereon.

19. The method of claim 11, further comprising:
providing a pair of 3D glasses having a first lens that filters a first color and a second lens that filters a second color; and
rendering the first grating background in the first color, and rendering the second grating background and the one or more moving visual stimuli overlaid thereon in the second color so that when the subject wears the 3D glasses the dominant eye of the subject sees only the first grating background and the non-dominant eye of the subject sees only the second grating background and the one or more moving visual stimuli overlaid thereon.

20. The method of claim 19, wherein the orientation of the grating of the one or more moving visual stimuli overlaid on the second grating background is substantially the same as the second angle, and the phase of the grating of the one or more moving visual stimuli overlaid on the second grating background is a phase shift relative to the second grating background.

21. A system for reducing sensory eye dominance or amblyopia, comprising:
a processor;
a display screen;
a controller configured to receive a user action; and
a non-transitory storage medium configured to store a computer program comprising instructions that, when executed, cause the processor to:
cause the display screen to render, for a dominant eye of a subject, a first grating background oriented at a first angle with respect to the display screen,
cause the display screen to render, for a non-dominant eye of the subject, a second grating background oriented at a second angle with respect to the display screen and one or more moving visual stimuli in a cat-and-mouse game, each of the one or more moving visual stimuli is overlaid on the second grating background and comprises a grating having a contrast, a phase and a grating orientation, and defines a speed of movement,
instruct the subject to identify the one or more moving visual stimuli overlaid on the second grating background,
cause the controller to receive one or more user actions responsive to identifying the one or more moving visual stimuli overlaid on the second grating background,
measure a reaction time based on when a visual stimulus is rendered on the display screen and when a user action responsive to identifying the visual stimulus is received by the controller,
calculate a score based on the one or more user actions and the reaction time, and
test reliability of the subject by causing the display screen to momentarily overlay an additional grating onto the grating of the one or more moving visual stimuli overlaid on the second grating background, and wherein the additional grating is oriented orthogonal to the grating of the one or more moving visual stimuli overlaid on the second grating background.

22. The system of claim 21, wherein the computer program further comprises instructions that, when executed, cause the display screen to render one or more visual stimuli overlaid on the first grating background.

23. The system of claim 21, wherein the first and second grating backgrounds are the same.

24. The system of claim 21, wherein the orientation of the grating of the one or more moving visual stimuli overlaid on the second grating background is substantially orthogonal to the second angle.

25. The system of claim 21, wherein the computer program further comprises instructions that, when executed, cause the processor to adjust a level of difficulties for the subject based on the calculated score.

26. The system of claim 25, wherein the instructions for adjusting the level of difficulties will cause the display screen to change the contrast, the grating orientation, or the speed of movement of the one or more moving visual stimuli overlaid on the second grating background.

27. The system of claim 25, wherein the one or more moving visual stimuli overlaid on the second grating background comprise a contour line having a thickness, and wherein the instructions for adjusting the level of difficulties will cause the display screen to flash on/off the contour line or change the thickness of the contour line of the one or more moving visual stimuli overlaid on the second grating background.

28. The system of claim 21, wherein the display screen is configured to render the first grating background at a first portion of the display screen, and render the second grating background and the one or more moving visual stimuli overlaid thereon at a second portion of the display screen so that the dominant eye of the subject sees only the first grating background and the non-dominant eye of the subject sees only the second grating background and the one or more moving visual stimuli overlaid thereon.

29. The system of claim 21, further comprising a pair of 3D glasses configured to filter a first color in a first lens and filter a second color in a second lens, wherein the display screen is configured to render the first grating background in the first color, and render the second grating background and the one or more moving visual stimuli overlaid thereon in the second color so that when the subject wears the 3D glasses the dominant eye of the subject sees only the first grating background and the non-dominant eye of the subject sees only the second grating background and the one or more moving visual stimuli overlaid thereon.

30. The system of claim 29, wherein the orientation of the grating of the one or more moving visual stimuli overlaid on the second grating background is substantially the same as the second angle, and the phase of the grating of the one or more moving visual stimuli overlaid on the second grating background is a phase shift relative to the second grating background.

31. A method for reducing sensory eye dominance or amblyopia, comprising:
  rendering, by a display screen, for a dominant eye of a subject, a first grating background, wherein the first grating background is oriented at a first angle with respect to the display screen;
  rendering, by the display screen, for a non-dominant eye of the subject:
    a second grating background oriented at a second angle with respect to the display screen, and
    one or more moving visual stimuli in a cat-and-mouse game, wherein each of the one or more moving visual stimuli is overlaid on the second grating background, and comprises a grating having a contrast, a phase and a grating orientation, and defines a speed of movement;
  instructing, by a processor, the subject to identify the one or more moving visual stimuli overlaid on the second grating background;
  receiving, by a controller, one or more user actions responsive to identifying the one or more moving visual stimuli overlaid on the second grating background;
  measuring, by the processor, a reaction time based on when a visual stimulus is rendered on the display screen and when a user action responsive to identifying the visual stimulus is received;
  calculating, by the processor, a score based on the one or more user actions and the reaction time; and
  testing reliability of the subject by causing the display screen to momentarily overlay, on the display screen, an additional grating onto the grating of the one or more moving visual stimuli overlaid on the second grating background, wherein the additional grating is oriented orthogonal to the grating of the one or more moving visual stimuli overlaid on the second grating background.

32. The method of claim 31, further comprising rendering, by the display screen, one or more visual stimuli overlaid on the first grating background.

33. The method of claim 31, wherein the first and second grating backgrounds are substantially same.

34. The method of claim 31, wherein the grating orientation of the grating of the one or more moving visual stimuli overlaid on the second grating background is substantially orthogonal to the second angle.

35. The method of claim 31, further comprising adjusting, by the processor, a level of difficulties for the subject based on the calculated score.

36. The method of claim 35, wherein adjusting the level of difficulties for the subject comprises changing the contrast, the grating orientation, or the speed of movement of the one or more moving visual stimuli overlaid on the second grating background.

37. The method of claim 35, wherein the one or more moving visual stimuli overlaid on the second grating background comprise a contour line having a thickness, and wherein adjusting the level of difficulties for the subject comprises flashing on/off the contour line or changing the thickness of the contour line of the one or more moving visual stimuli overlaid on the second grating background.

38. The method of claim 31, further comprising rendering, by the display screen, the first grating background at a first portion of the display screen, and rendering the second grating background and the one or more moving visual stimuli overlaid thereon at a second portion of the display screen so that the dominant eye of the subject sees only the first grating and the non-dominant eye of the subject sees only the second grating background and the one or more moving visual stimuli overlaid thereon.

39. The method of claim 31, further comprising:
  providing a pair of 3D glasses having a first lens that filters a first color and a second lens that filters a second color; and
  rendering the first grating background in the first color, and rendering the second grating background and the one or more moving visual stimuli overlaid thereon in the second color so that when the subject wears the 3D glasses the dominant eye of the subject sees only the first grating background and the non-dominant eye of the subject sees only the second grating background and the one or more moving visual stimuli overlaid thereon.

40. The method of claim 39, wherein the orientation of the grating of the one or more moving visual stimuli overlaid on the second grating background is substantially the same as the second angle, and the phase of the grating of the one or more moving visual stimuli overlaid on the second grating background is a phase shift relative to the second grating background.

* * * * *